(12) United States Patent
Loria

(10) Patent No.: US 11,045,320 B2
(45) Date of Patent: Jun. 29, 2021

(54) PENILE SLEEVE DEVICES AND PENILE STOCKING INSERT AND METHODS OF MAKING THE SAME

(71) Applicant: Loria Products LLC, Miami, FL (US)

(72) Inventor: Victor Loria, Miami, FL (US)

(73) Assignee: LORIA PRODUCTS LLC, Miami, FL (US)

( * ) Notice: Subject to any disclaimer, the term of this patent is extended or adjusted under 35 U.S.C. 154(b) by 0 days.

(21) Appl. No.: 16/655,586

(22) Filed: Oct. 17, 2019

(65) Prior Publication Data

US 2020/0368025 A1 Nov. 26, 2020

Related U.S. Application Data

(63) Continuation of application No. 16/416,760, filed on May 20, 2019, now Pat. No. 10,517,730.

(51) Int. Cl.
*A61F 2/26* (2006.01)
(52) U.S. Cl.
CPC ........ *A61F 2/26* (2013.01); *A61F 2230/0006* (2013.01); *A61F 2230/0069* (2013.01)
(58) Field of Classification Search
CPC ............... A61F 2/26; A61F 2230/0006; A61F 2230/0069
USPC ...................................... 600/38–41
See application file for complete search history.

(56) References Cited

U.S. PATENT DOCUMENTS

| | | |
|---|---|---|
| 3,987,789 A | 10/1976 | Timm et al. |
| 4,204,530 A | 5/1980 | Finney |
| 4,335,714 A | 6/1982 | Edgerton et al. |
| 4,392,562 A | 7/1983 | Burton et al. |
| 4,523,584 A | 6/1985 | Yachia et al. |

(Continued)

FOREIGN PATENT DOCUMENTS

WO   WO 2005/065598   7/2005

OTHER PUBLICATIONS

Elist, J., "A Single-Surgeon Retrospective and Preliminary Evaluation of the Safety and Effectiveness of the Penuma Silicone Sleeve Implant for Elective Cosmetic Correction of the Flaccid Penis", Journal of Sexual Medicine, 2018;15:1216-1223.

(Continued)

*Primary Examiner* — Samuel G Gilbert
(74) *Attorney, Agent, or Firm* — Caesar Rivise, PC

(57) ABSTRACT

A penile sleeve device (PSD) that is an implantable subcutaneous penile shaft silicone rubber apparatus which has several functions such as to elongate, thicken, harden, straighten and custom shape a penis. The PSD has an elongated main component of stretchable elastic silicone elastomer into which an inner component of a much higher durometer silicone rubber material is positioned to provide the PSD with some rigidity. The main component is the only portion in contact with the penile shaft since the inner component resides within a pocket of the main component that is formed by two layers therein. The outside surface of these layers may include folds to assist in enhancing penile girth and lengthening. A penile stocking insert is also provided for increasing the length of the penis it is flaccid or erect state using an elongated tubular body constructed from an elastic material which applies a compressive force around the penile shaft, thus elongating the length of the penis.

10 Claims, 54 Drawing Sheets

(56) References Cited

U.S. PATENT DOCUMENTS

| | | | |
|---|---|---|---|
| 4,602,625 A * | 7/1986 | Yachia | A61F 2/26 600/40 |
| 5,167,611 A | 12/1992 | Cowan | |
| 5,445,594 A * | 8/1995 | Elist | A61F 2/26 600/38 |
| 5,669,870 A | 9/1997 | Elist | |
| 5,899,849 A | 5/1999 | Elist | |
| D462,770 S | 9/2002 | Elist | |
| 6,475,137 B1 | 11/2002 | Elist | |
| 6,537,204 B1 | 3/2003 | Elist | |
| 7,572,221 B2 | 8/2009 | Atala et al. | |
| 8,622,889 B1 | 1/2014 | Loria | |
| 8,986,193 B1 | 3/2015 | Elist | |
| 9,504,573 B1 | 11/2016 | Elist | |
| 9,662,241 B1 | 5/2017 | Loria | |
| 9,877,835 B1 | 1/2018 | Loria | |
| 9,993,578 B1 | 6/2018 | Loria | |
| 10,105,253 B1 | 10/2018 | Loria | |
| 10,350,070 B2 | 7/2019 | Elist | |
| 10,413,413 B1 * | 9/2019 | Cornell | A61F 2/26 |
| 2008/0269643 A1 * | 10/2008 | Morriss | A61B 5/1076 600/587 |
| 2011/0054250 A1 | 3/2011 | Morningstar | |

OTHER PUBLICATIONS

International Search Report for related PCT Application No. PCT/US2020/032846 dated Aug. 13, 2020.

Penuma, "Penuma Implant for Men—About Us". Retrieved May 30, 2019 from https://www.penuma.com/.

* cited by examiner

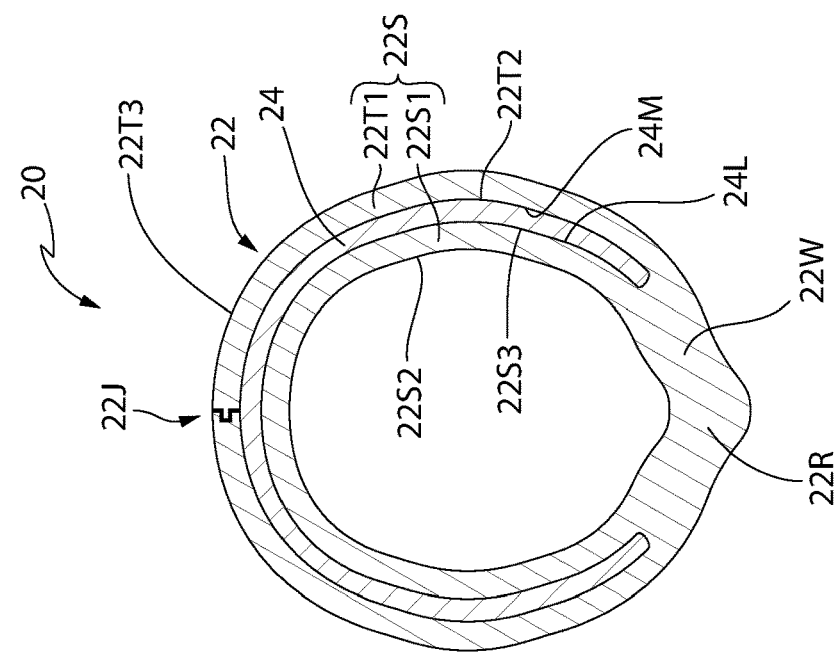
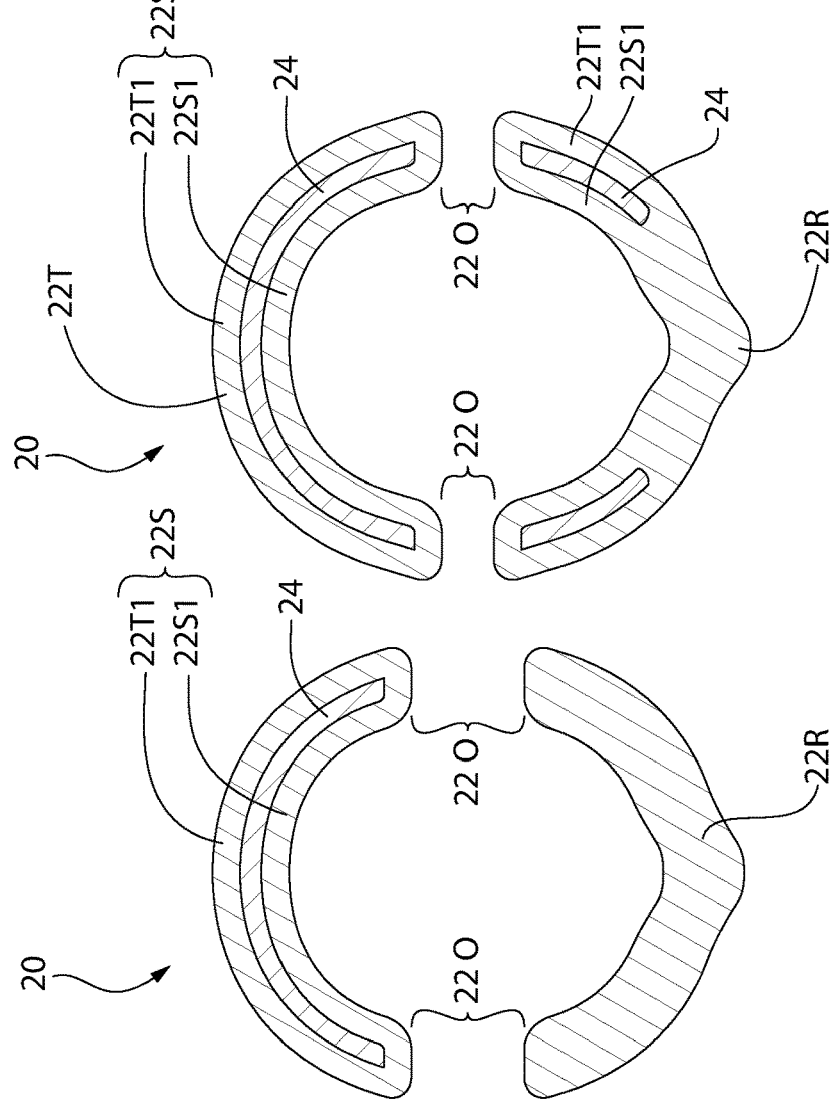
FIG. 1H  FIG. 1G  FIG. 1F

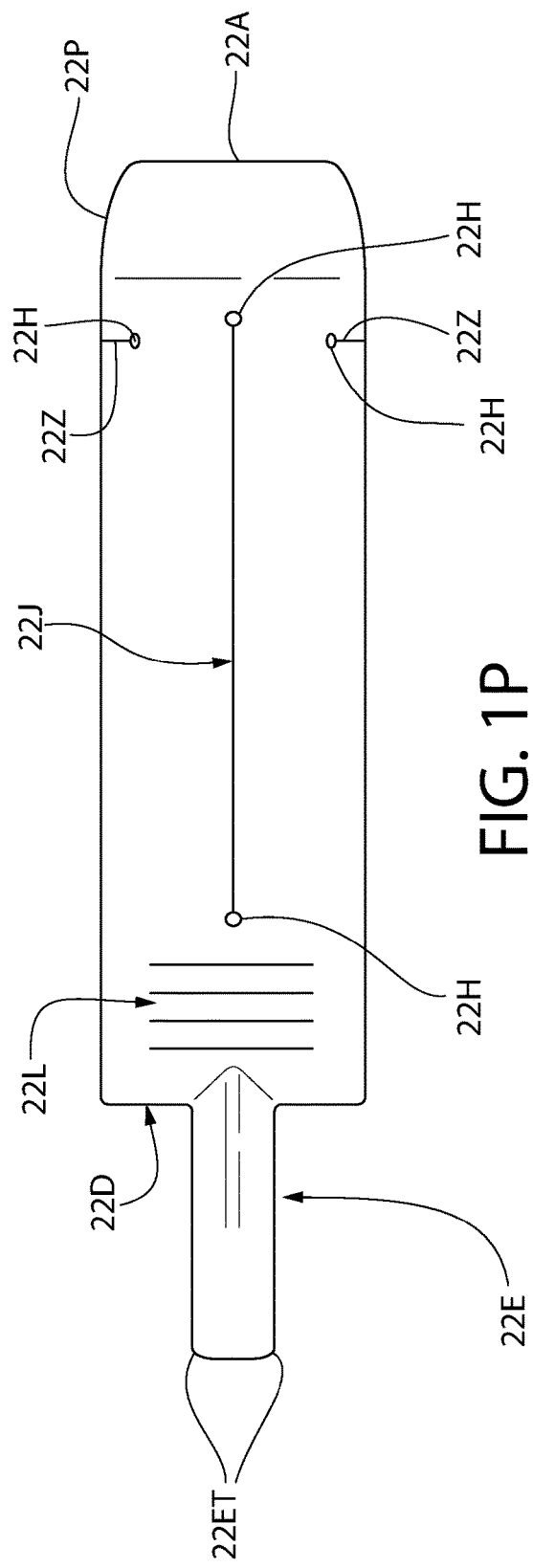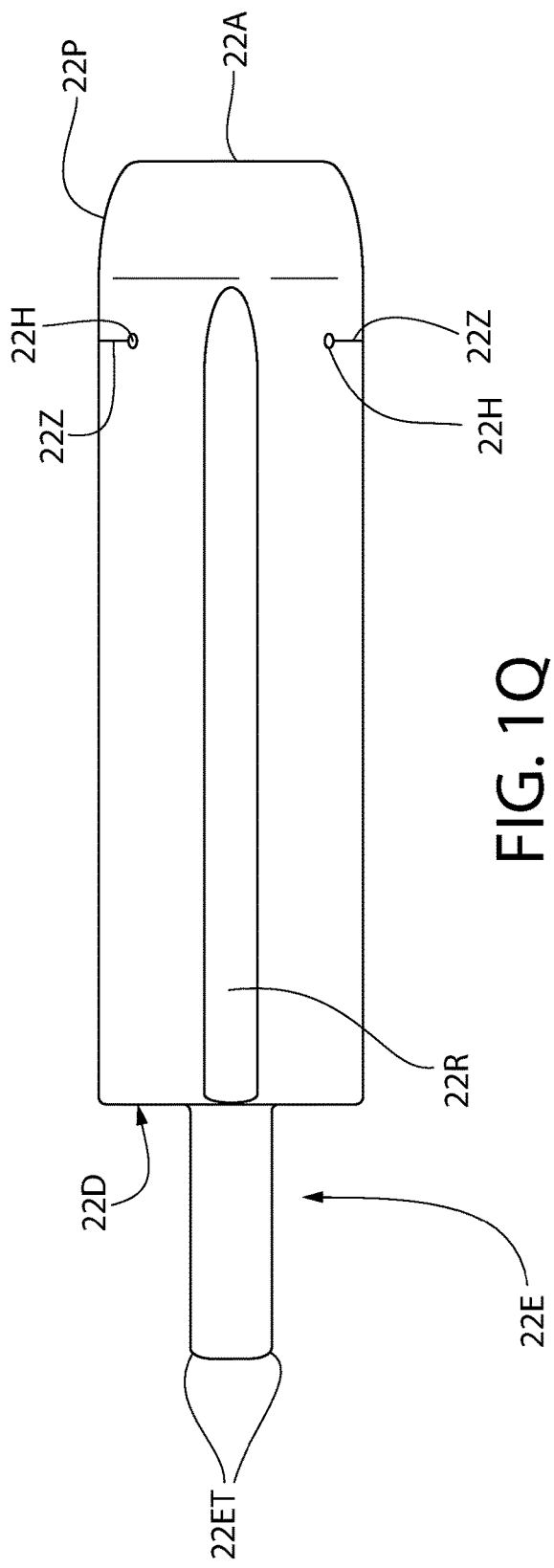

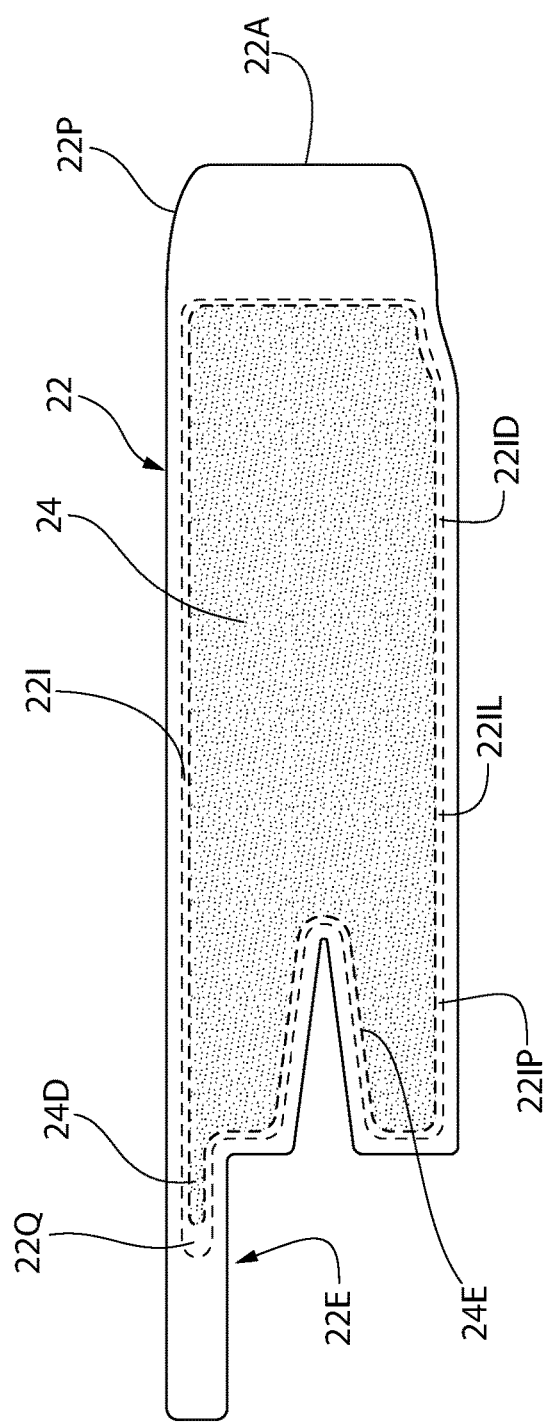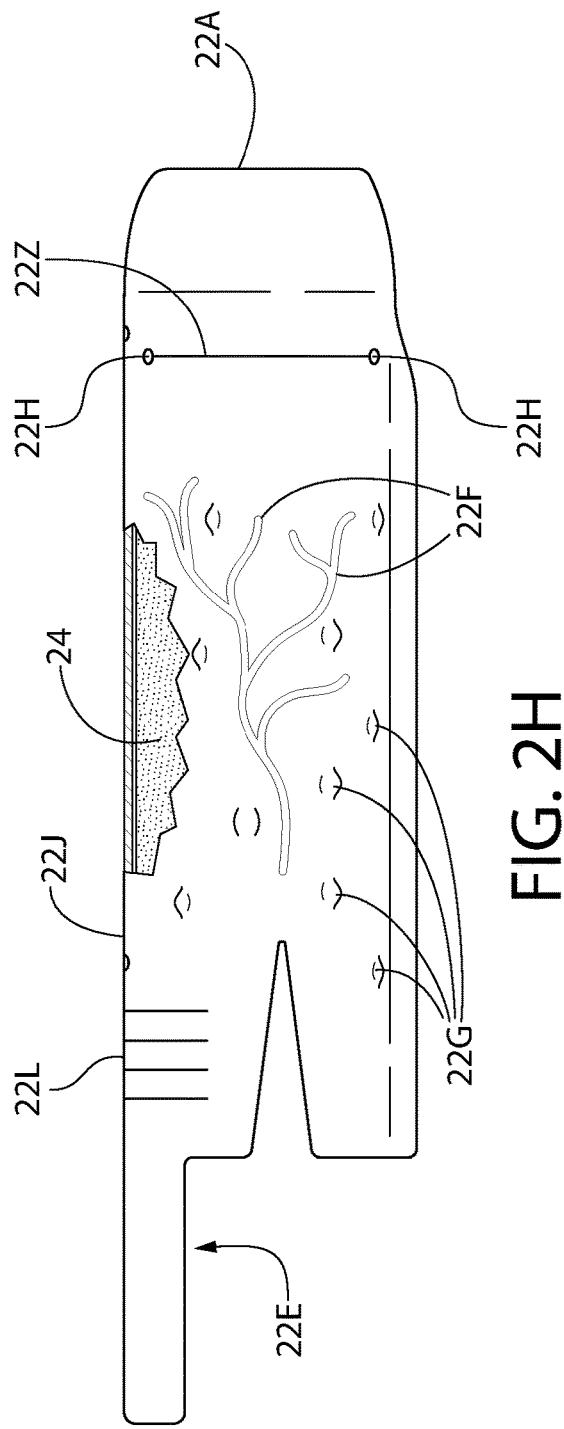

Erect Measurements

Hyperextended Measurements

Flaccid Measurements

Flaccid Degloved Measurements

Erect Degloved Measurements

Hyperextended Degloved Measurements

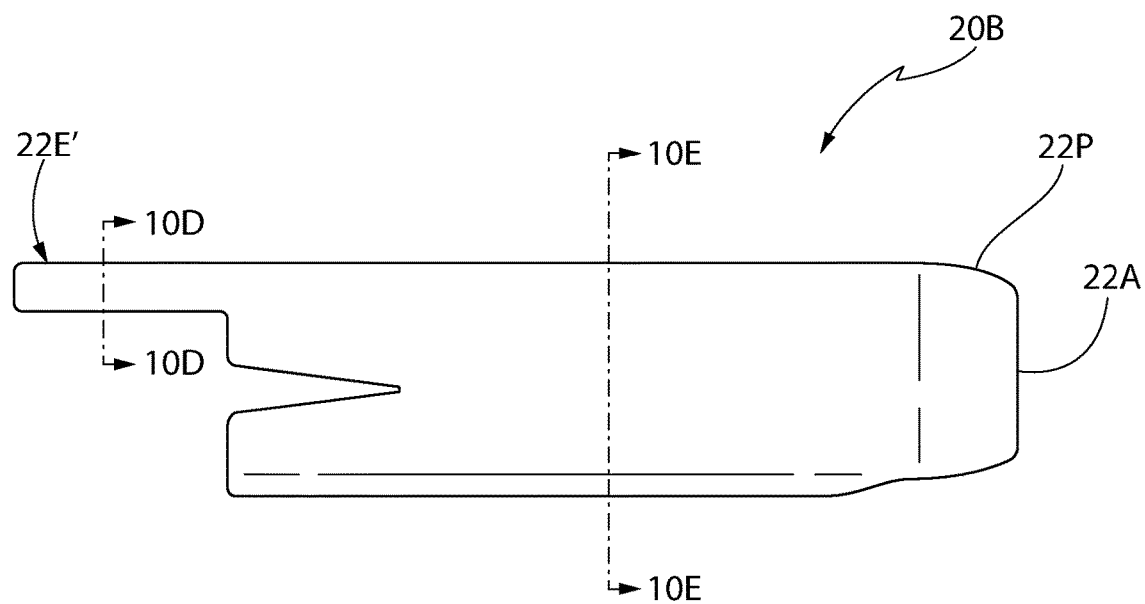
FIG. 10C
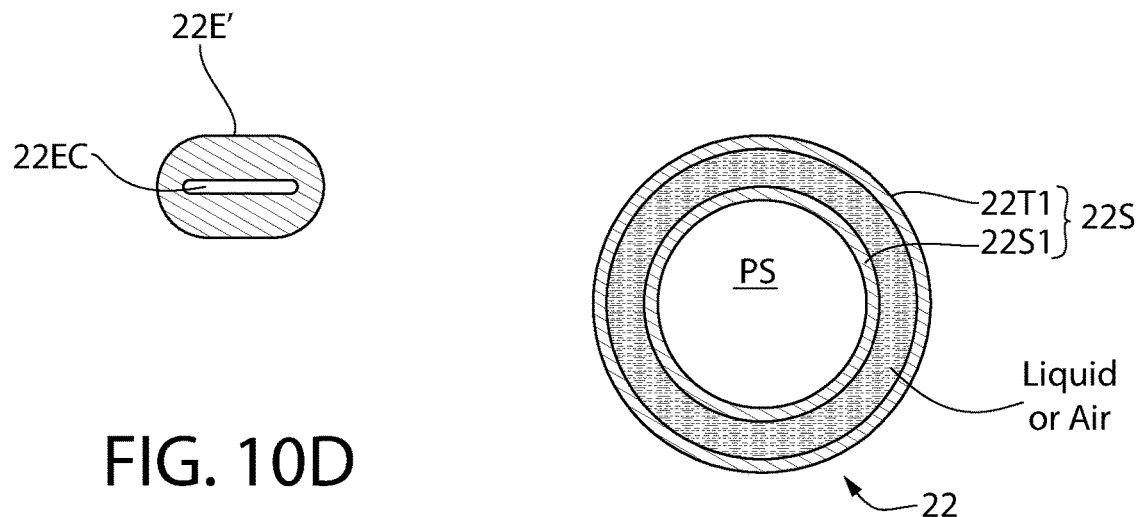
FIG. 10D
FIG. 10E

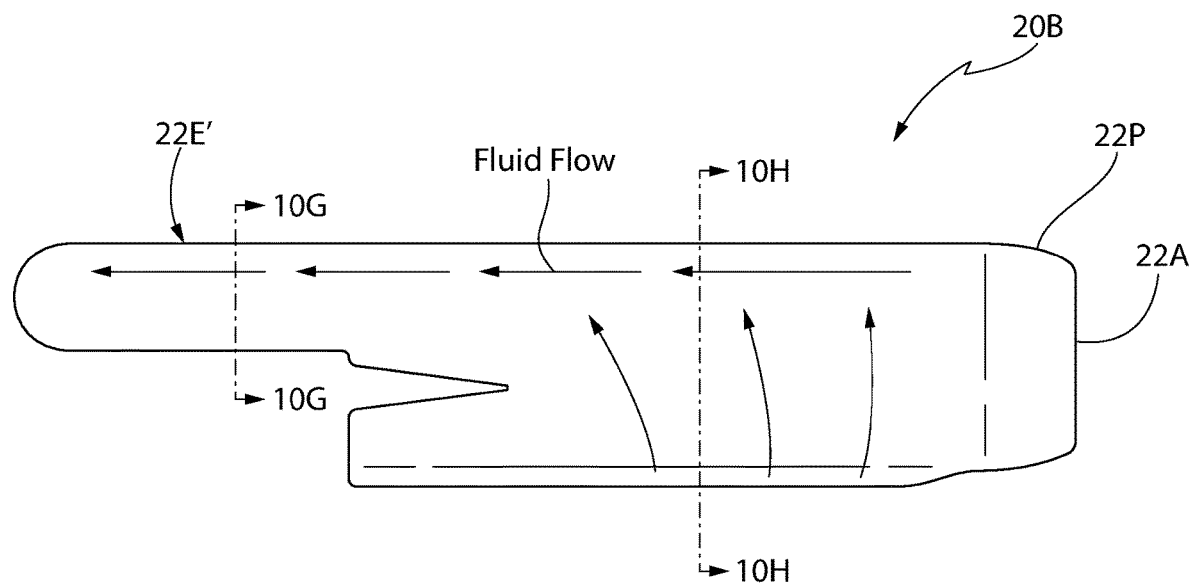
FIG. 10F
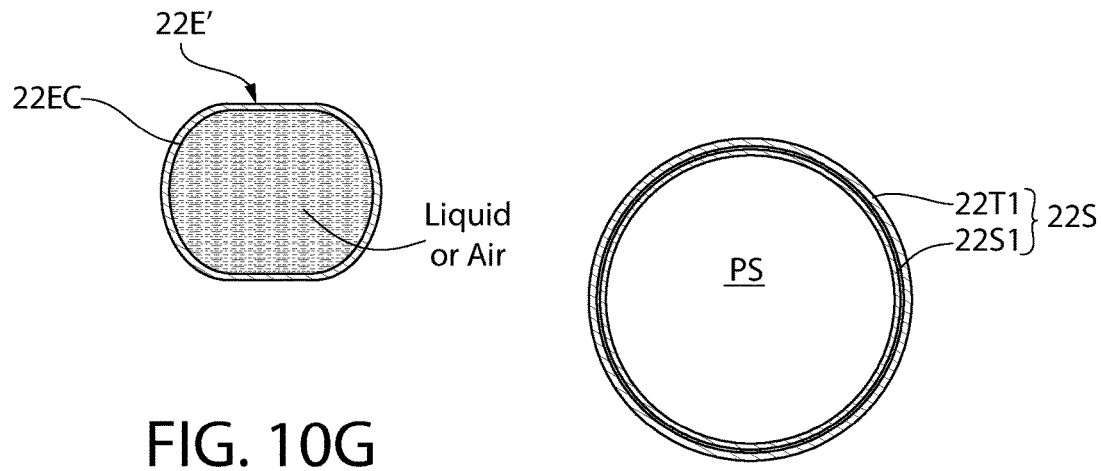
FIG. 10G
FIG. 10H

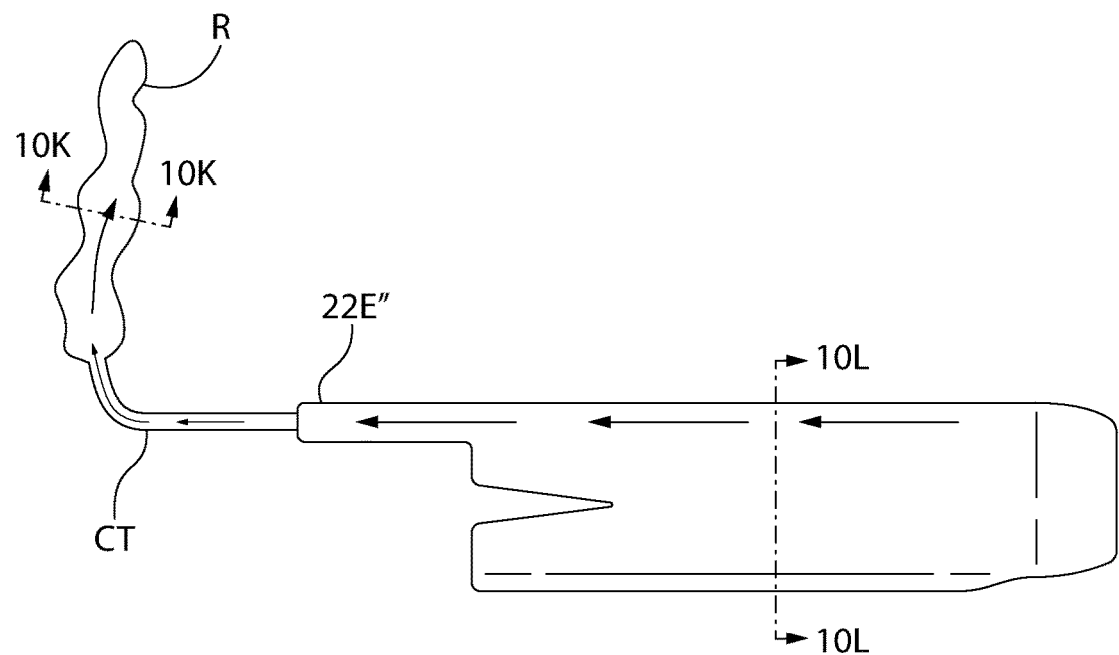
FIG. 10J
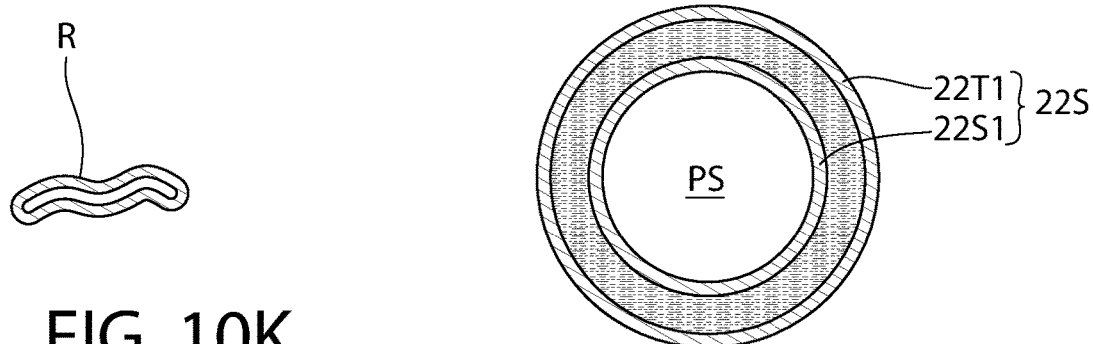
FIG. 10K
FIG. 10L

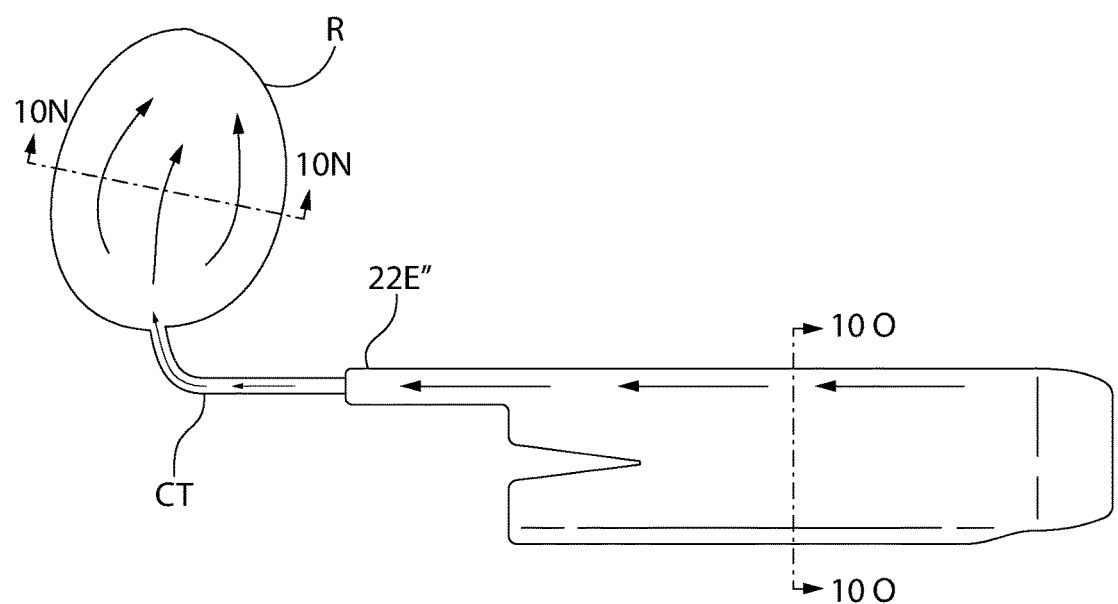
FIG. 10M
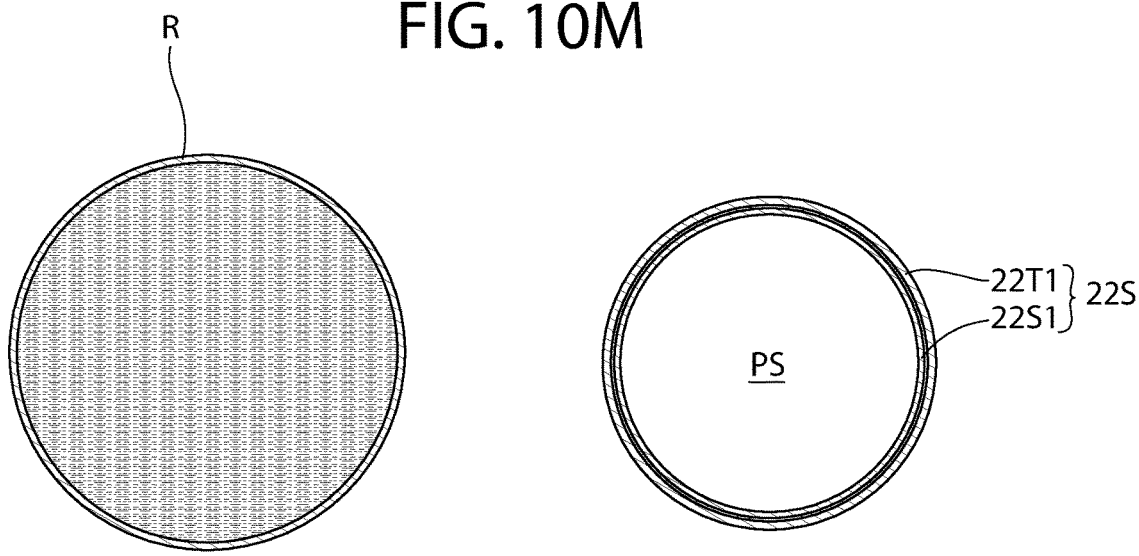
FIG. 10N
FIG. 10 O

PENILE SLEEVE DEVICES AND PENILE STOCKING INSERT AND METHODS OF MAKING THE SAME

CROSS-REFERENCE TO RELATED APPLICATIONS

This Continuation application claims the benefit under 35 U.S.C. § 120 of application Ser. No. 16/416,760 filed on May 20, 2019 entitled PENILE SLEEVE DEVICES AND PENILE STOCKING INSERT AND METHODS OF MAKING THE SAME and whose entire disclosure is incorporated by reference herein.

BACKGROUND OF THE INVENTION

The present invention relates to penile implants and more particularly to an implantable sub-cutaneous penile sleeve device (PSD) that serves a plurality of functions such as elongating the penile shaft in the flaccid and/or erect states, increasing penile girth in both states, hardening/increasing penile firmness, straightening a curved penis, and custom-shaping a penis. A penile stocking insert is also disclosed for elongating the length of the penis in the flaccid and/or erect states.

The flaccid penis retracts under certain circumstances, perhaps most notably in cold environments, upon vigorous exercise, and upon elicitation of the "fight or flight" response. Penile retraction is due to the emptying of blood resulting in volume reduction, the contraction of the dartos muscle, and the retraction or recoiling of the collagen, elastic, and muscle fibers in the penile tissue during the erect to flaccid state transition. Retraction of the penis results in a significant volume decrease in the apparent size of the penis, which can be a source of embarrassment to one undergoing penile retraction, especially in gym locker rooms, public showers, in the presence of their sexual partner, and the like. Therefore, it is desirable to prevent penile retraction in order to not only avoid potential embarrassment, but to also improve confidence and self-esteem.

Currently there are medical and surgical treatments for erectile dysfunction (ED). When medical treatments fail to provide added firmness, such as VIAGRA® or similar oral medications, or injectable ED medications, etc., then there are surgical options such as having an implant placed deep into the penis.

Implant devices are typically considered when patients have moderate erectile dysfunction. There are two types of implant devices, the metal rod type, and the balloon pump type, as shown in U.S. Pat. No. 3,987,789 (Timm, et al.) and U.S. Pat. No. 5,167,611 (Cowan, et al.), respectively. Both of these devices are placed directly into the corpora cavernosa CC (see FIGS. 8C and 8E; under general anesthesia and with deep cutting into the penile tissues) resulting in extensive tissue damage to the fine sinusoidal architecture of the cavernosa CC. This sinusoidal architecture is designed to receive and hold blood in the normal corpora cavernosum, thereby maintaining a natural erection. After placement of these implant devices, there is no turning back because the tissue damage caused by the insertion of these implant devices is permanent, and now the patient will be totally reliant on this internal device for erections. These surgical implant options, in perspective, are reasonable remedies, even with the tissue damage, since there is total or near total erectile malfunction of the penis with all medical options exhausted. In addition to the tissue damage sustained by the insertion of the implant device, the balloon implants can malfunction. These balloon implant types are composed of many parts, valves, fluid reservoirs, etc., and may not only malfunction but simply "break". If the implant device were to malfunction, and they inevitably will, they would then need to be replaced, thereby requiring another operation and exposing the patient, again, to the same risks of infection, anesthesia, etc. Lastly, the balloon and metal rod type implants are limiting, only providing erection support to the penile shaft. These devices do not take into consideration certain medical safety issues with high tension situations and potential tissue trauma, such as high direct pressure on the glans causing the balloons or rods to press up (an under) the glans tissue causing possible trauma and tearing of tissues. The current PSD 20 design will allow to treat low to moderate level ED, eliminating the risks of major tissue trauma from rod or balloon placement, delay indefinitely this major surgical step in treatment, and can, if needed or desired, easily reverse and remove this PSD 20 without permanent damage.

U.S. Pat. No. 9,877,835 (Loria) discloses a penile insert device that can increase the length of a penis in its flaccid or erect state and which uses a plurality of alternating lateral plateaus and lateral valleys to effect the change of penis length.

Other examples of penile implant structures are set forth in U.S. Pat. Nos. 5,445,594; 5,669,870; 5,899,849; 6,475,137; 6,537,204; and 8,986,193 by Elist. However, in some cases, the structures disclosed therein are of a very high durometer, or hardness, and with minimal to no flexibility. This device is in direct contact with penile tissues which can result in creating pressure points. These structures can transmit stress directly to the penis glans and sub-glans tissues which may result in irritation, inflammation, skin erosion, tenderness and pain and possibly may even rupture the device through the skin.

Thus, there remains a need for a penile insert device that serves a plurality of functions in effecting enhancements to penile length, girth, appearance, feel, and providing safer low to moderate level erectile dysfunction remedies, while avoiding the creation of pressure points that can result in patient pain and discomfort.

All references cited herein are incorporated herein by reference in their entireties.

BRIEF SUMMARY OF THE INVENTION

A penile sleeve device configured for implantation in the subcutaneous space of a patient's penis for enhancing or correcting penis shape and size, treating low to moderate level erectile dysfunction, or correcting penis curvature or malformation is disclosed. The penile sleeve device comprises: an elongated tubular section comprising a flexible elastomer for maintaining the penis outstretched in a flaccid or erect state, wherein the elongated tubular section has a proximal end flange, configured for positioning near the pubic bone, and has a tapered distal end, configured for positioning adjacent the glans of the penis, and wherein the elongated tubular section is configured to be positioned around the penile shaft in the subcutaneous space of the patient's penis.

A method for forming a penile sleeve device configured for implantation in the subcutaneous space of a patient's penis for enhancing or correcting penis shape and size, treating low to moderate level erectile dysfunction, or correcting penis curvature or malformation is disclosed. The method comprises: forming an elongated tubular section from a flexible elastomer for maintaining the penis outstretched in a flaccid or erect state, and wherein the forming further comprises forming an flange, configured for positioning near the pubic bone, on a proximal end of the elongated tubular section while forming a tapered portion, configured for positioning adjacent the glans of the penis, on a distal end of the elongated tubular section.

A method for enhancing penis shape or to correct penis shape dysfunction by implanting a penile sleeve device in the subcutaneous space of a patient's penis is disclosed. The method comprises: (a) degloving the penis by surgically exposing the subcutaneous space of the patient's penis by cutting the penile shaft skin at the circumcision line, revealing the penile shaft; (b) obtaining measurements of the penile shaft during an induced erect penile state as well as during a flaccid state to form "penile measurements"; (c) forming a first elongated tubular section comprising a flexible elastomer based on the penile measurements for maintaining the penis outstretched in a flaccid or erect state, wherein the first elongated tubular section comprises a longitudinal pocket formed between an inner layer and an outer layer of the elongated tubular member and wherein the first elongated tubular section also comprises a first plurality of suture slits; (d) forming an elongated open-tubular section, based on the penile measurements, comprising a high durometer silicone rubber material or a metal malleable alloy for providing hardness feature to the penile sleeve device, wherein the elongated open-tubular section has a second plurality of suture holes that are configured to align with the first plurality of suture holes when the elongated open-tubular section is inserted within the longitudinal pocket to form the penile sleeve device; (e) inserting a working end of a delivery device into an aperture within a dorsal side of the elongated open-tubular device, and wherein the aperture is accessible via a dorsal mid-line slit in the outer layer; (f) positioning a glans gripper device through a tubular tunnel in the penile sleeve device; (g) orienting a first end of the penile sleeve device to be aligned with the penis glans and manipulating the glans gripper device to grasp the penis glans; (h) sliding the penile sleeve device onto and over the penis glans using the delivery device which is driven towards the pubic area while the glans gripper device pulls the penis glans in the opposite direction, until a proximal end flange of the penile sleeve device is positioned in the pubic pocket space near the pubic bone/ligament area and a tapered distal end of the penile sleeve device is positioned adjacent the coronal rim of the penis glans, at which time the delivery device is disengaged and removed and the glans gripper device releases the penis glans; (i) inserting a marking instrument through the aligned plurality of suture slits to mark on the penile tissue the location of suture points; (j) rolling back the tapered end of the penile sleeve device and then inserting sutures through the plurality of suture slits in the penile sleeve device and into the Tunica Albuginea and up through the plurality of slits; (k) unrolling the tapered end of the penile sleeve device and tying the sutures to secure the penile sleeve device to the penis; (l) regloving the penis by restoring the penile shaft skin along the penis shaft and connecting the skin at the circumcision line using sutures.

BRIEF DESCRIPTION OF SEVERAL VIEWS OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1F is a cross-sectional view of the PSD taken along line 1F-1F of FIG. 1A;

FIG. 1G is a cross-sectional view of the PSD taken along line 1G-1G of FIG. 1A;

FIG. 1H is a cross-sectional view of the PSD taken along line 1H-1H of FIG. 1A;

FIG. 1P is a top view of the dorsal side of the PSD of FIG. 1A;

FIG. 1Q is a bottom view of the ventral side of the PSD of FIG. 1A;

FIG. 2G is cross-sectional view of the PSD showing the internal component positioned inside the pocket of the main component;

FIG. 2H is a partial break-away side view of the PSD showing a portion of the internal component within the main component;

FIG. 10C depicts an alternative PSD embodiment referred to as the "PSD Collapsible" whereby fluid is initially stored between the main component's inner and outer layer when the penis is in a flaccid state;

FIG. 10D is a cross-sectional view of the proximal end flange taken along line 10D-10D of FIG. 10C;

FIG. 10E is a cross-sectional view of the middle portion of the PSD Collapsible taken along line 10D-10D of FIG. 10C;

FIG. 10F depicts the PSD embodiment when the penis becomes erect, thereby pushing the stored fluid into the proximal end flange, causing the proximal end flange to expand;

FIG. 10G is a cross-sectional view of the proximal end flange taken along line 10G-10G of FIG. 10F;

FIG. 10H is a cross-sectional view of the middle portion of the PSD Collapsible taken along line 10H-10H of FIG. 10F;

FIG. 10J is a functional diagram of the PSD Volume Shift embodiment showing how fluid moves from the PSD through the proximal end flange and into the reservoir;

FIG. 10K is a cross-sectional view of the reservoir taken along line 10K-10K of FIG. 10J;

FIG. 10L is a cross-sectional view of the middle portion of the PSD Volume Shift taken along line 10L-10L of FIG. 10J;

FIG. 10M is a functional diagram of the PSD Volume Shift embodiment showing the condition of the PSD Volume Shift when the penis is fully erect;

FIG. 10N is a cross-sectional view of the reservoir taken along line 10N-10N of FIG. 10M;

FIG. 10O is a cross-sectional view of the middle portion of the PSD Volume Shift taken along line 10O-10O of FIG. 10M;

DETAILED DESCRIPTION OF THE PREFERRED EMBODIMENTS

Figure 1:
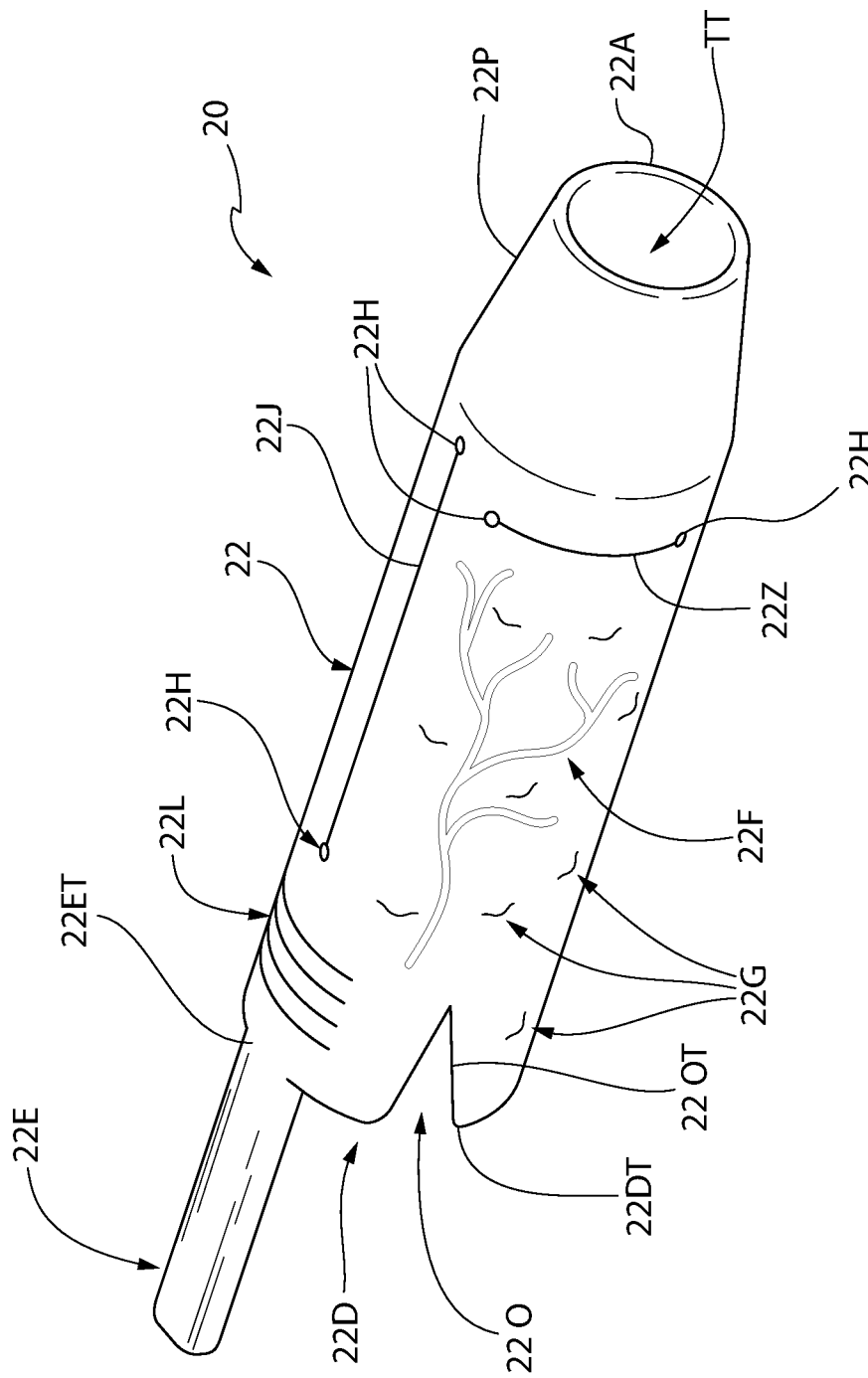
FIG. 1 is an isometric view of the penile sleeve device (PSD)

Referring now to the figures, wherein like reference numerals represent like parts throughout the several views, exemplary embodiments of the present disclosure will be described in detail. Throughout this description, various components may be identified having specific values, these values are provided as exemplary embodiments and should not be limiting of various concepts of the present invention as many comparable sizes and/or values may be implemented.

Any feature or combination of features described herein are included within the scope of the present invention provided that the features included in any such combination are not mutually inconsistent as will be apparent from the context, this Specification, and the knowledge of one of ordinary skill in the art. Additional advantages and aspects of the present invention are apparent in the following detailed description and claims.

As used herein, the term "proximal" refers to being situated near or towards the pubic area. The term "distal" refers to being situated away from the pubic area. The term "ventral" refers to the underside of the penile shaft. The term "dorsal" refers to the top side of the penile shaft. The term "medial" refers to the midline longitudinal area of the penile shaft. The term "lateral" refers to the right or left side of the penile shaft. The term "glans" refers to the 'head' of the penis. The term "glans corona" or "glans rim" or "coronal rim" refers to the base of the glans at its widest location. The term "penile shaft" refers to the tubular portion of the penis excluding the glans. The term "urethra" refers to the urinary tubular structure found on the ventral side of the penile shaft. The term "scrotum" refers to the skin that covers the testicles. The terms "epidermis" and "dermis" refer to the two primary layers of skin which is common to all skin, including the penile skin; the epidermis being the very top layer, and the dermis being the immediate layer below the epidermis. The term "glans meatus" is the 'hole' in the glans from which urine exits from. The term "fascia" refers to circular or tubular shaped tissue that forms the penile shaft structure, and this fascia is found immediately under the penile skin. There are three layers of this fascia; the first and most superficial is the "dartos fascia" which lies immediately under the penile skin; then the next layer of fascia is called "Buck's Fascia" which lies below the dartos fascia; and the final and deepest fascial layer is called the "tunica albuginea". All of these fascial layers form a tubular shape which forms the main structure of the penis itself. Where there is an erection, blood flows within the tunica albuginea, specifically into the space within this fascial layer called the corpora cavernosa and corpora spongiosum, and 'fills it up' and expands it like filling a tubular balloon with air. The term "buckle" refers to the ability to collapse or compress. The term "suture" refers to the string like material used for stitching up skin, etc. The term "gradually" or "tapering" is defined as rising or descending at an even, moderate inclination. The term "smoothly" is defined as having an even surface or edge free from irregularities, sharpness (i.e., hard-angled corners), or roughness.

Figures 2, 2A:
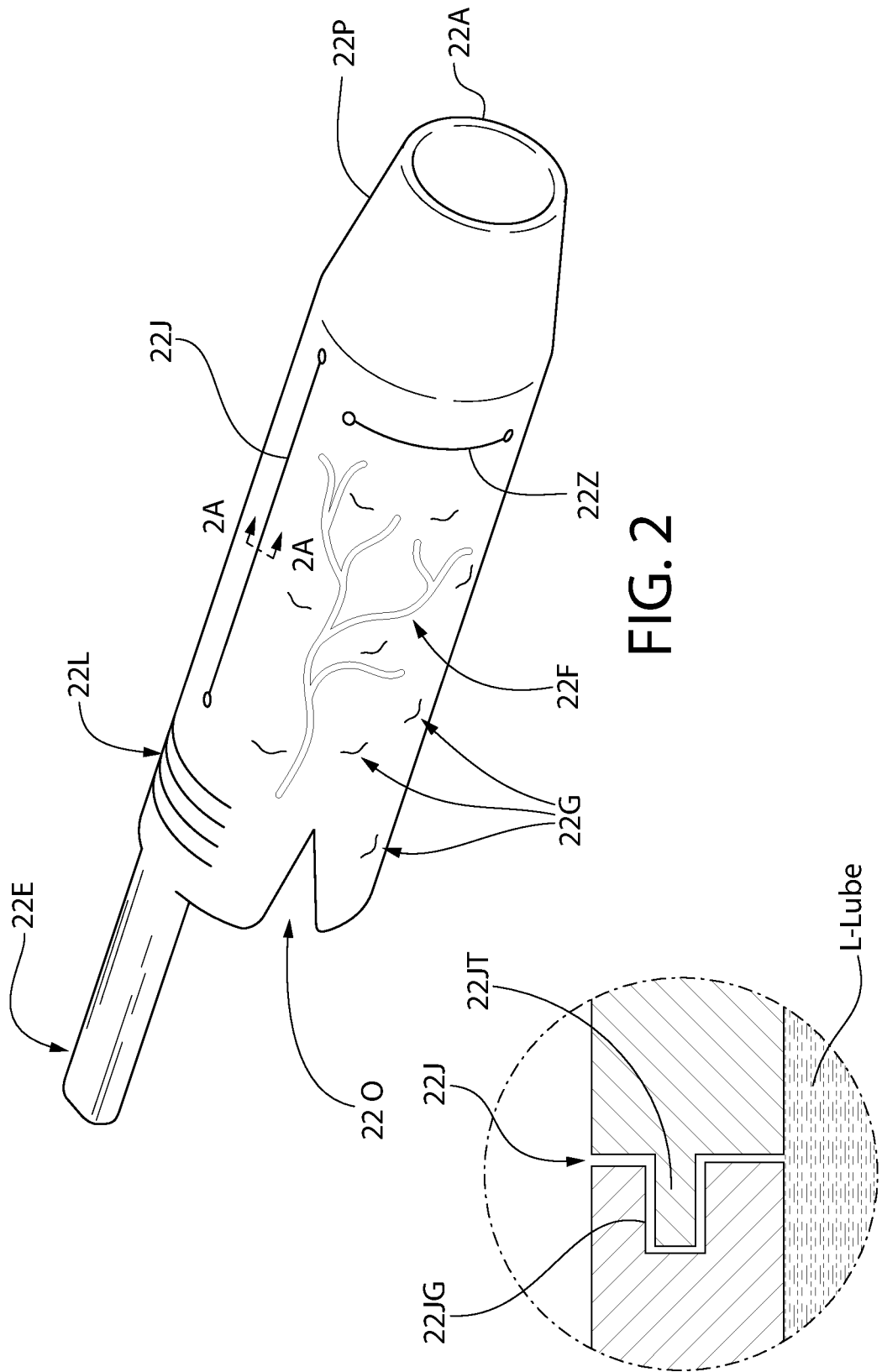
FIG. 2 is another isometric view of the PSD of FIG. 1A.
FIG. 2A is a cross-sectional view of the dorsal slit depicting how the slit forms a tongue-groove closure to maintain any liquids within the PSD.
Figure 2B:
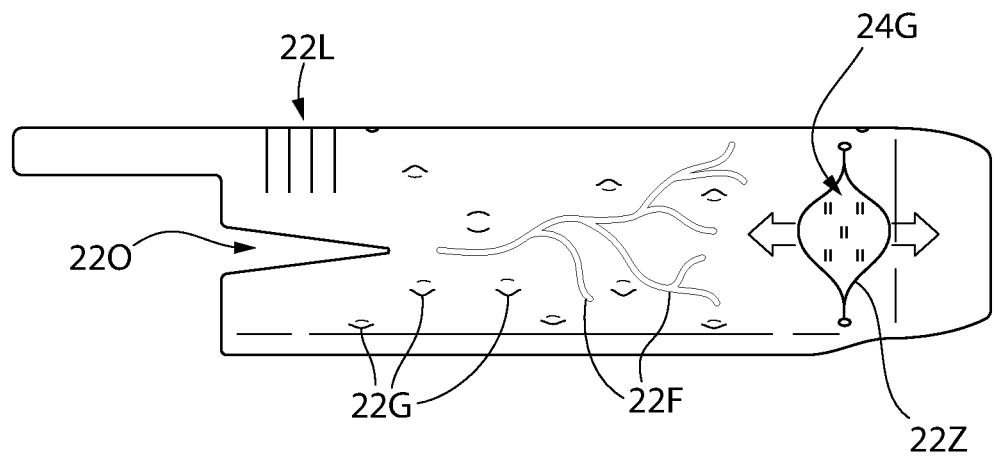
FIG. 2B is side view of the PSD showing a lateral slit is opened to expose the suture slits.
Figure 2C:
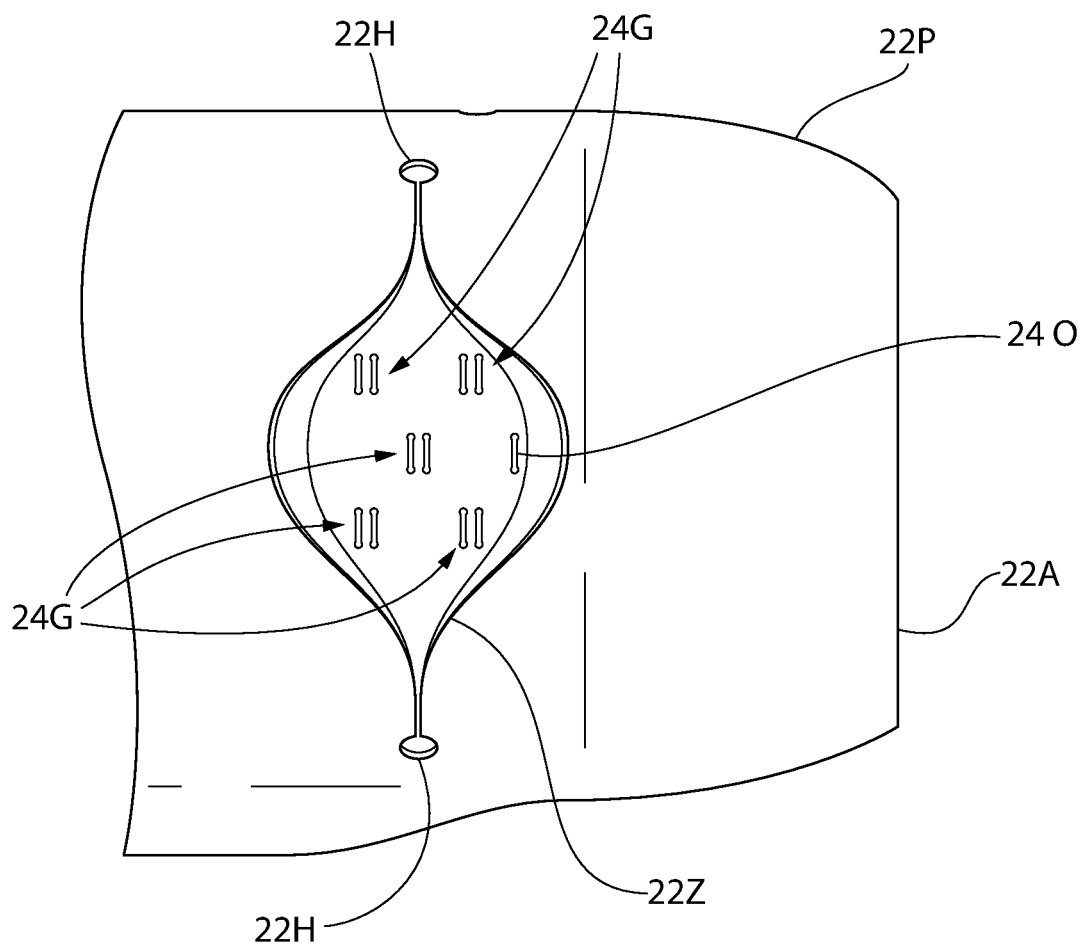
FIG. 2C is an enlarged view of the opened lateral slit of FIG. 2B exposing the suture slits.
Figure 2D:
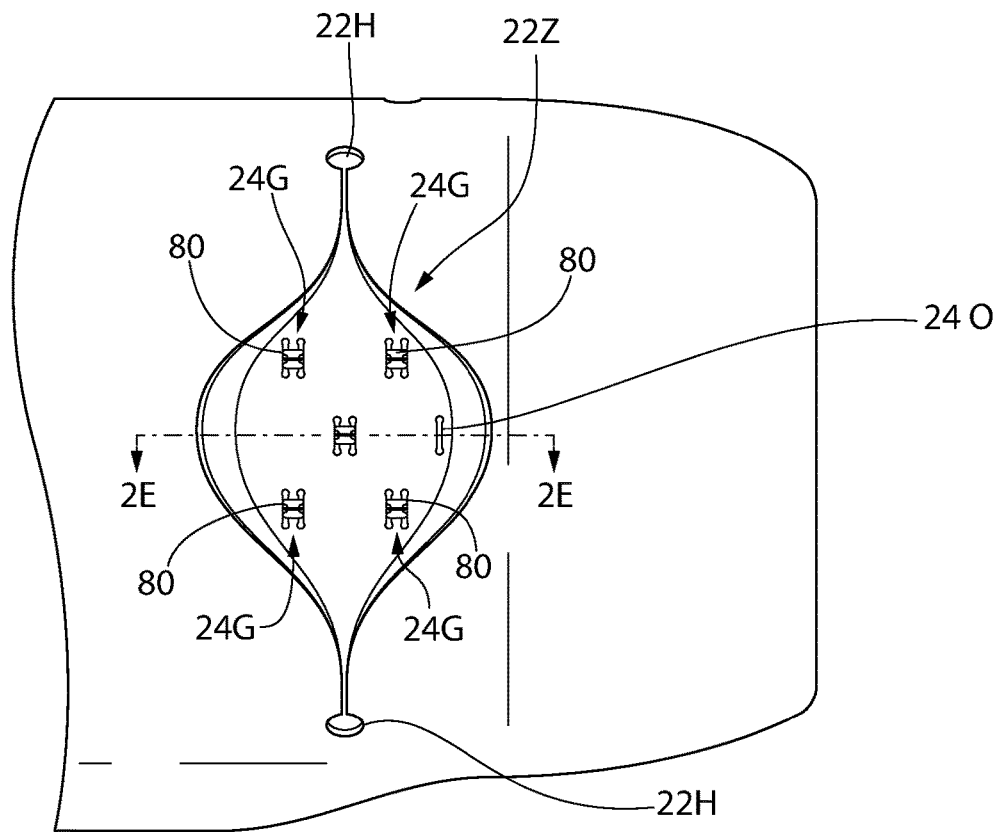
FIG. 2D is a view similar to the view of FIG. 2C but including the suture clips installed in the suture slits.
Figure 2E:
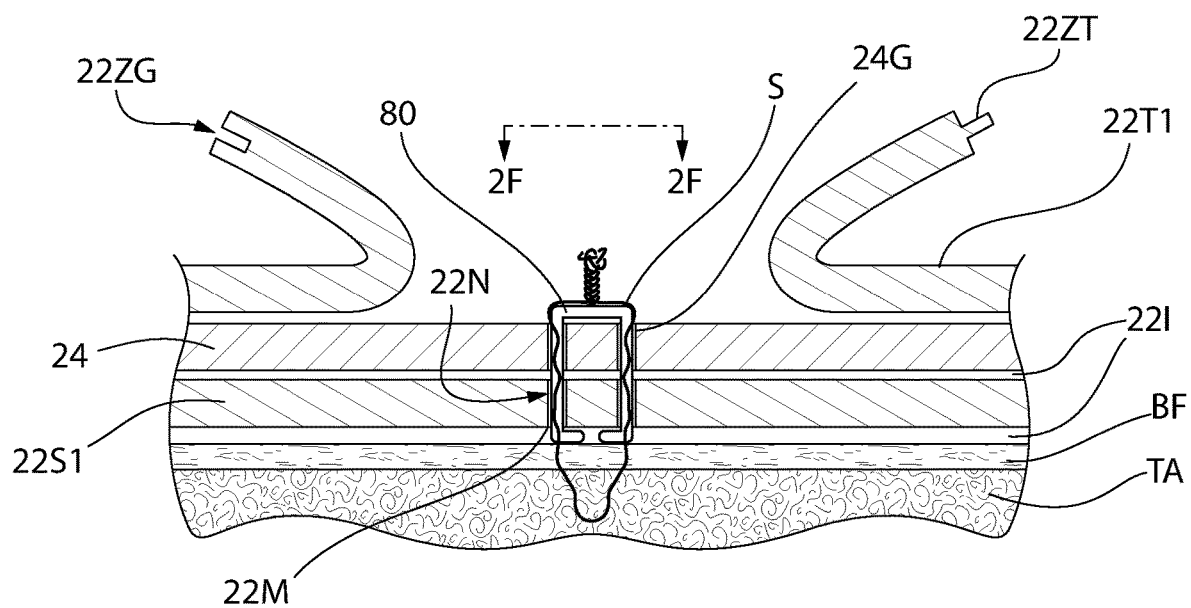
FIG. 2E is a cross-sectional view of one of the installed suture clip, taken along line 2E-2E, showing a suture secured to the penile shaft and around the suture clip.
Figure 2F:
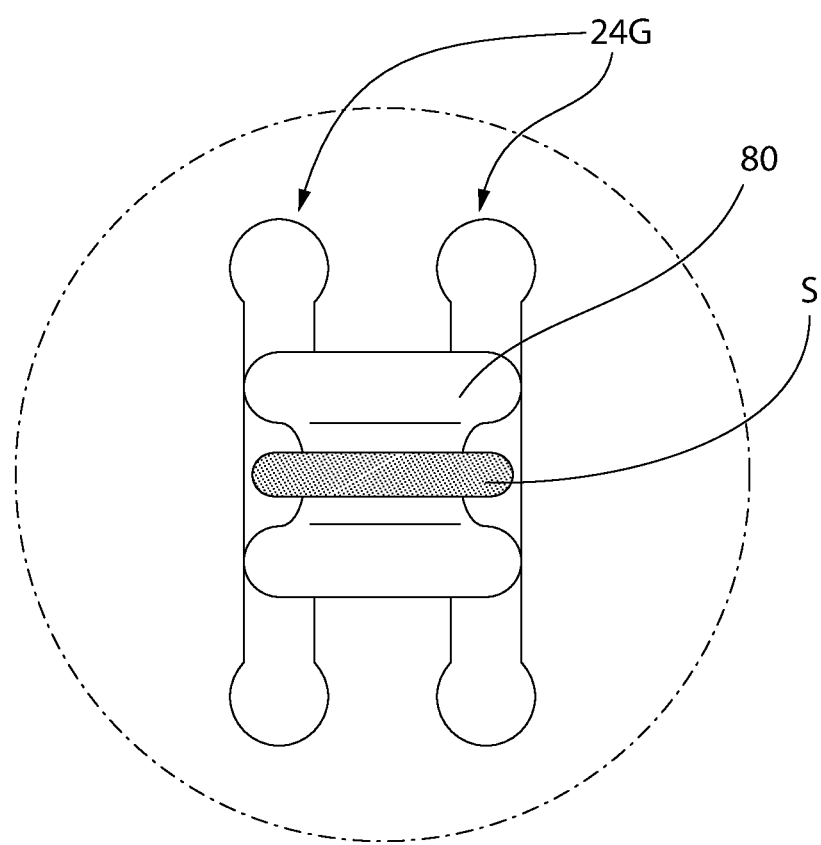
FIG. 2F is a plan view of one of the installed suture clips shown in FIGS. 2D-2E.
Figure 2I:
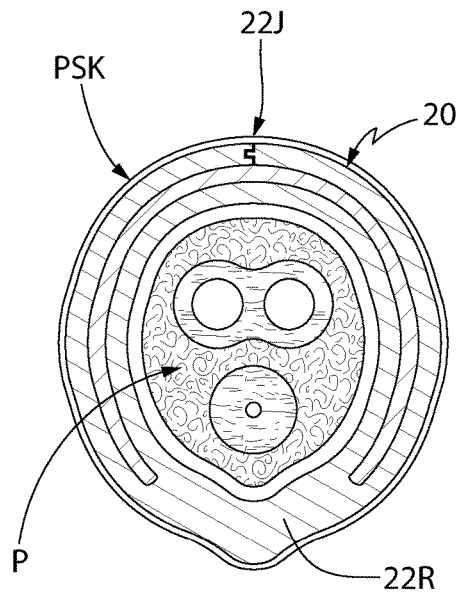
FIG. 2I is a cross-sectional view of the PSD implanted over the penile shaft and taken along a line similar to 1H-1H of FIG. 1A.
Figure 2J:
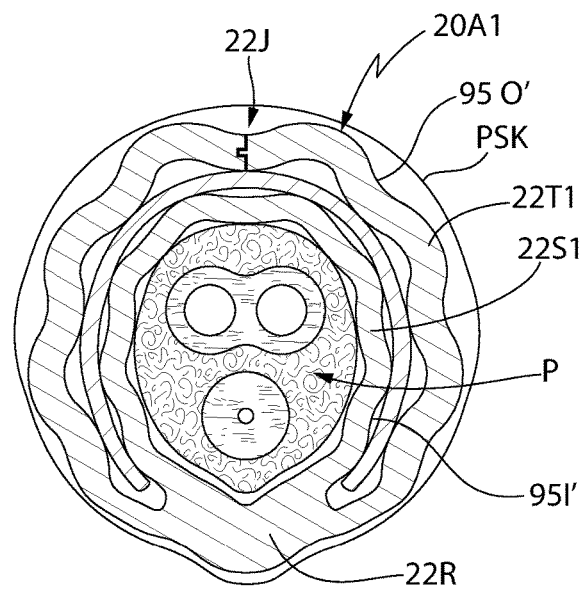
FIG. 2J is a cross-sectional view of another PSD embodiment, referred to as "PSD-wavy fold", implanted over the penile shaft and taken along a line similar to 1H-1H of FIG. 1A.
Figure 2K:
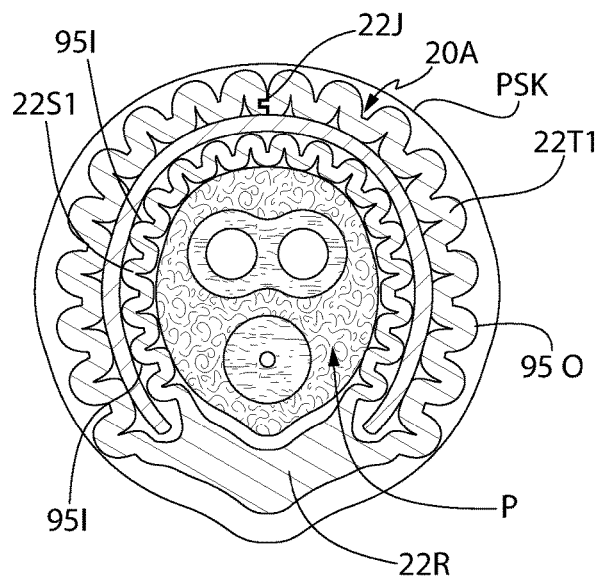
FIG. 2K is a cross-sectional view of another PSD embodiment, referred to as "PSD-S fold", implanted over the penile shaft and taken along a line similar to 1H-1H of FIG. 1A.
Figure 2L:
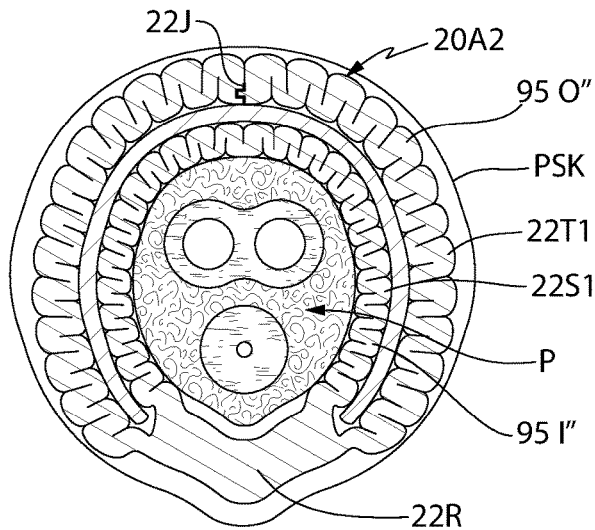
FIG. 2L is a cross-sectional view of another PSD embodiment, referred to as "PSD-Tight-S" fold, implanted over the penile shaft and taken along a line similar to 1H-1H of FIG. 1A.
Figure 10:
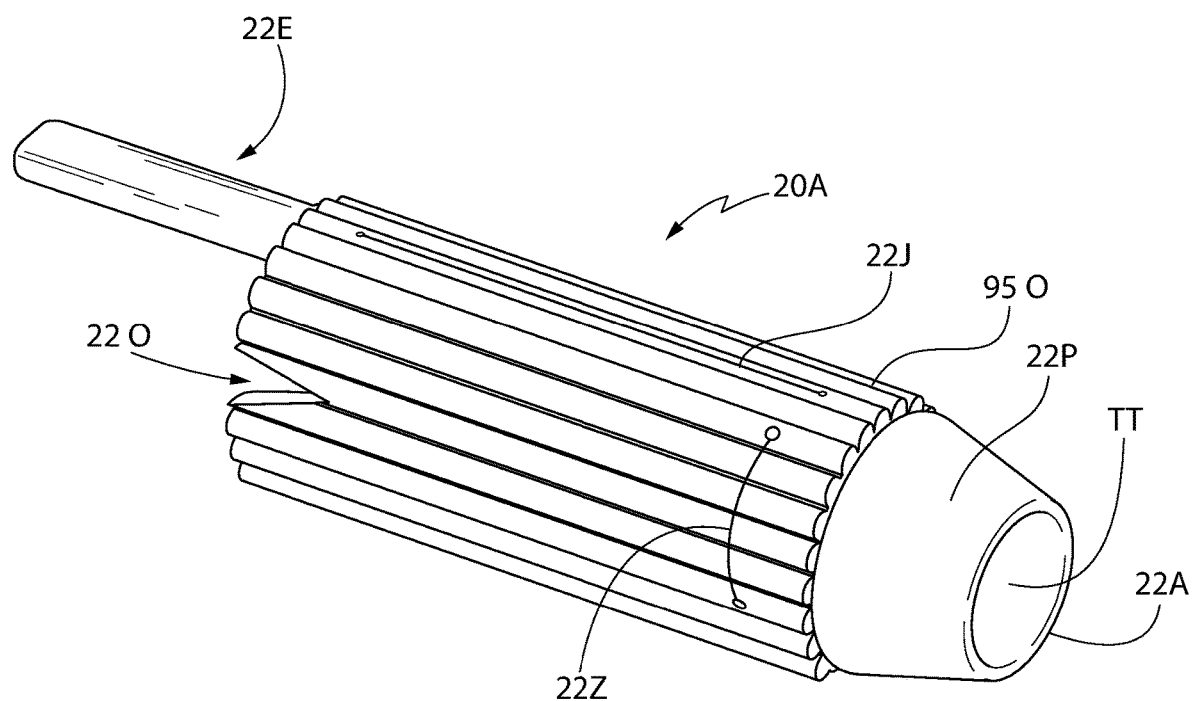
FIG. 10 is an isometric view of the PSD-S fold embodiment of the present invention.
Figure 10A:
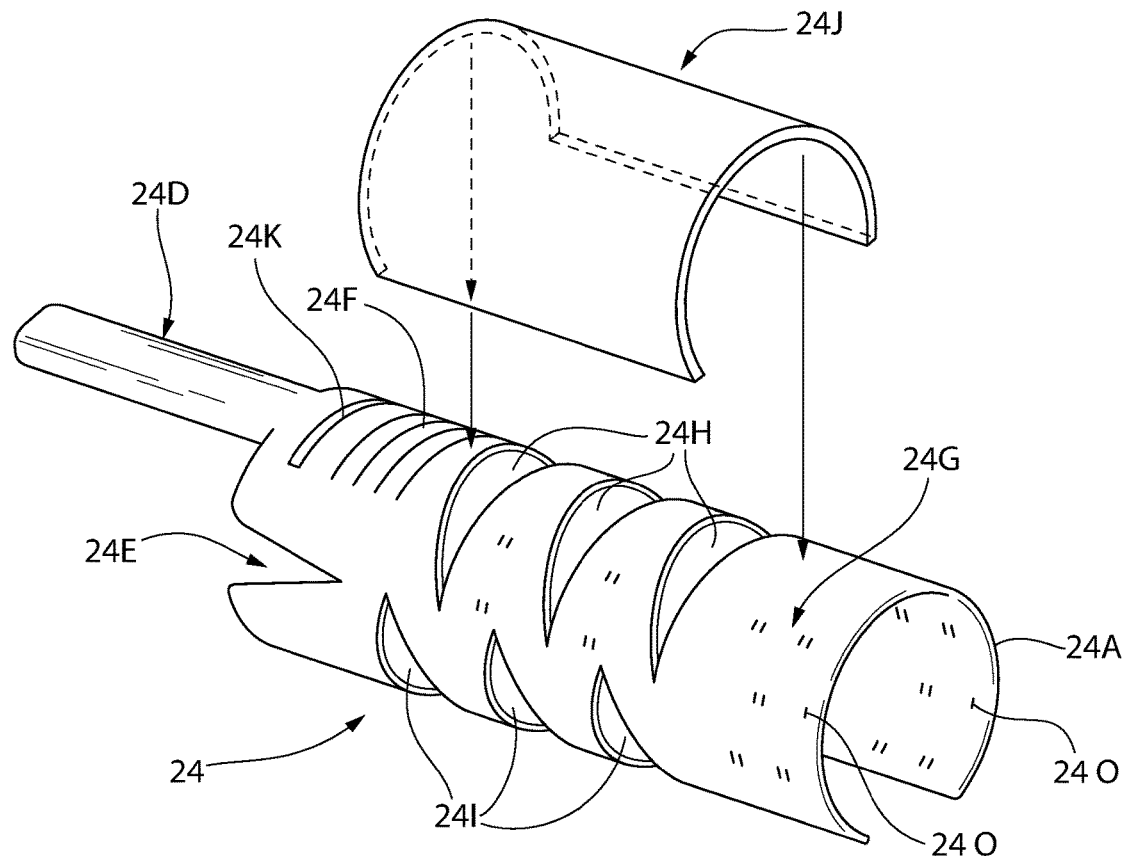
FIG. 10A is an exploded isometric of the inner component that utilizes a second semi-cylindrical second inner component thereon.
Figure 10B:
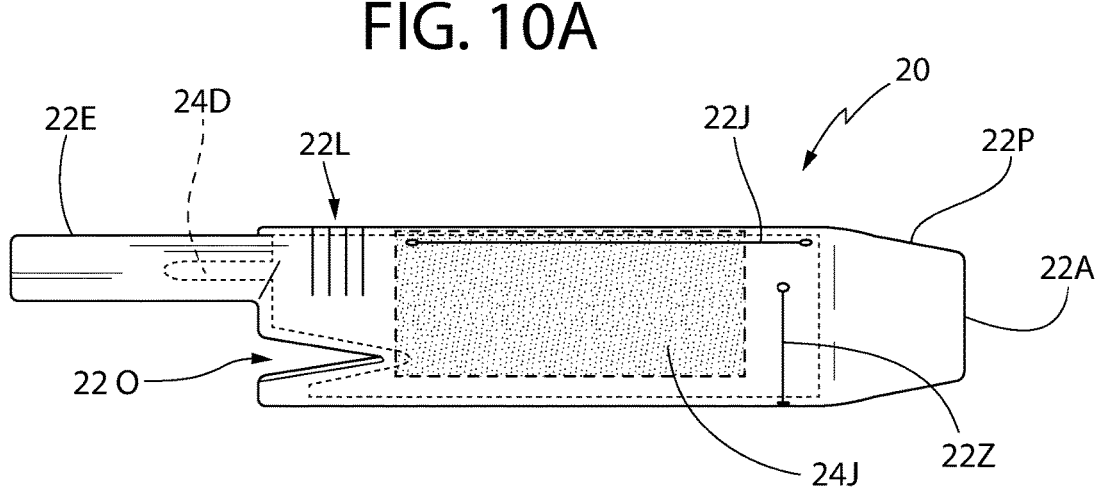
FIG. 10B is a partial longitudinal cross section showing how the internal component and the second internal component are positioned in the pocket of the main component.
Figure 10I:
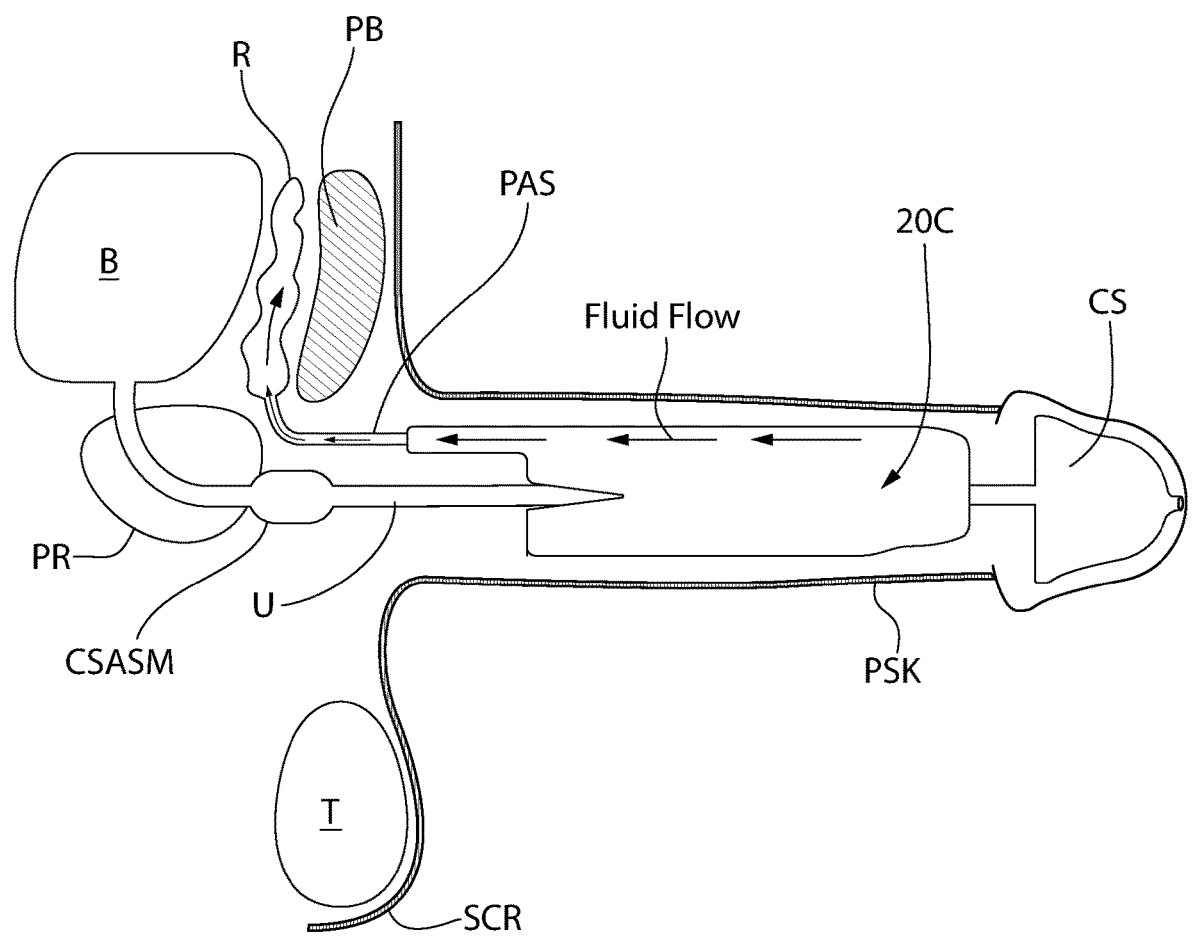
FIG. 10I depicts a further alternative PSD embodiment referred to as the "PSD Volume Shift" whereby an expandable reservoir is coupled to the PSD via the proximal end flange and which depicts the penis moving from a flaccid state to an erect state, thereby displacing stored fluid from the PSD, through the proximal end flange and into the reservoir.
Figure 10P:
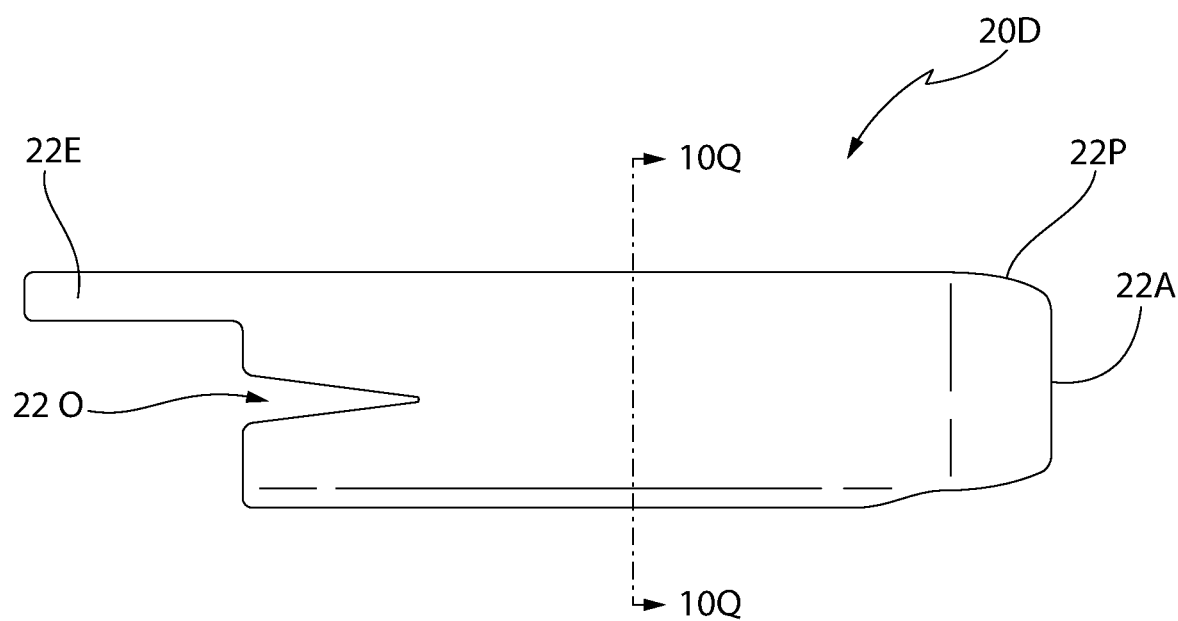
FIG. 10P is a side view of an even further alternative PSD embodiment referred to as the "PSD Spoke" whereby collapsible spokes between the inner layer and the outer layer of the main component are present to accommodate the change of penis state from flaccid to erect or vice versa.
Figure 10Q:
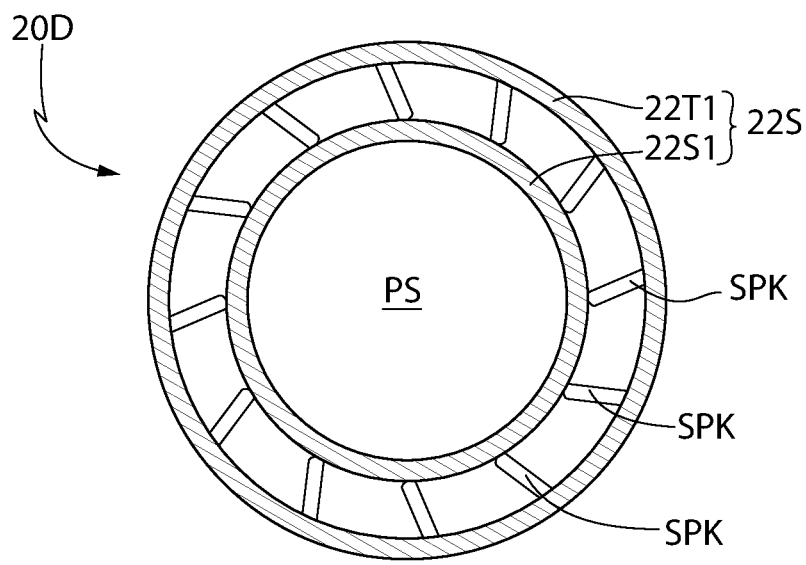
FIG. 10Q is a cross-sectional view of the PSD Spoke of FIG. 10P taken along line 10Q-10Q of FIG. 10P when the penis is in the flaccid state.
Figure 10R:
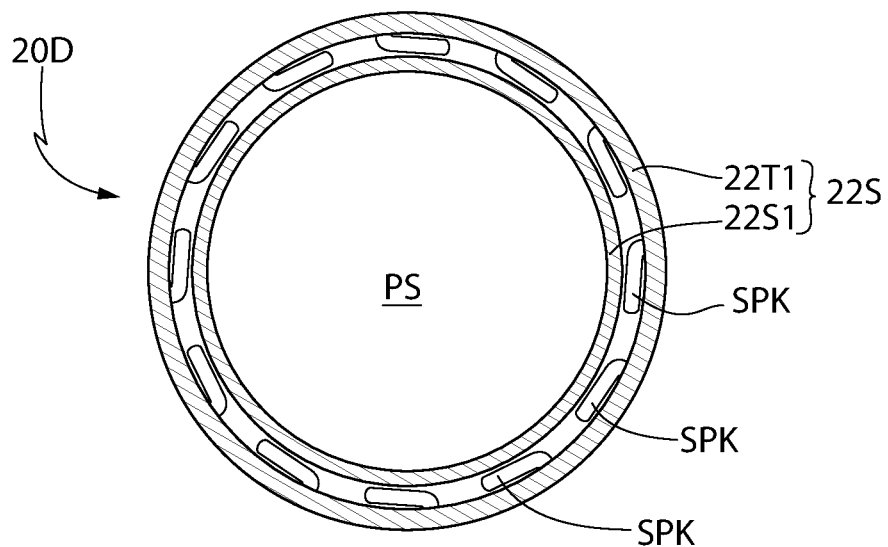
FIG. 10R is a cross-sectional view of the PSD Spoke of FIG. 10P taken along line 10Q-10Q of FIG. 10P when the penis is in the erect state, showing the spokes in a collapsed state.
Figure 10S:
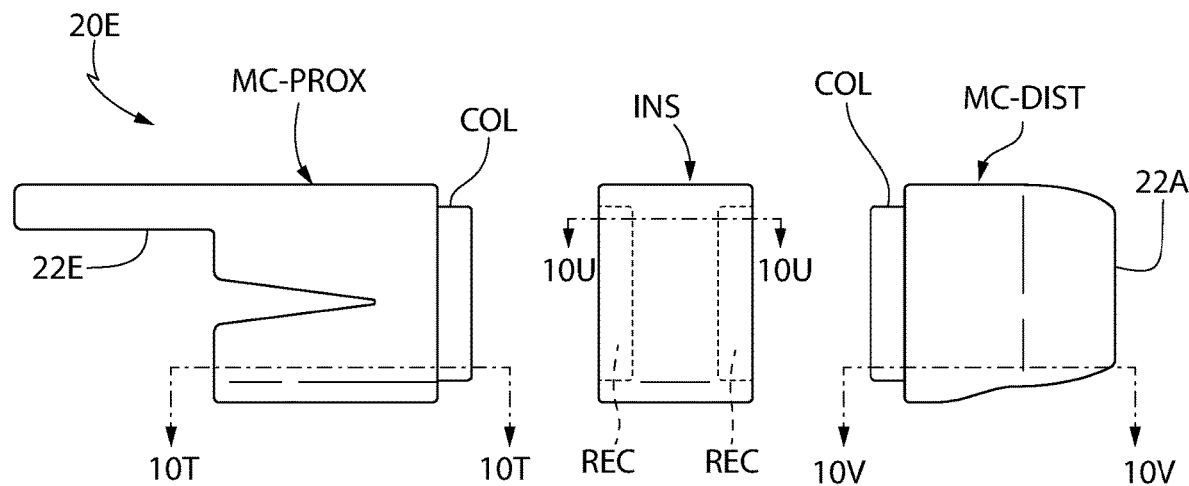
FIG. 10S is a side exploded view of another alternative PSD embodiment referred to as the "PSD Insert" whereby the main component of the PSD has discrete members that are coupled together using tongue and groove connections.
Figure 10T:
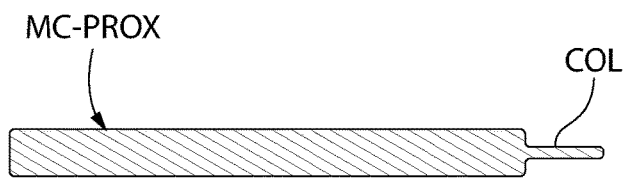
FIG. 10T is a cross-sectional view of the PSD Insert taken along line 10T-10T of FIG. 10S.
Figure 10U:
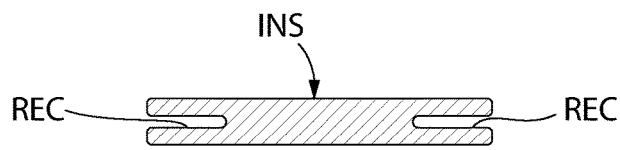
FIG. 10U is a cross-sectional view of the PSD Insert taken along line 10U-10U of FIG. 10S.
Figure 10V:
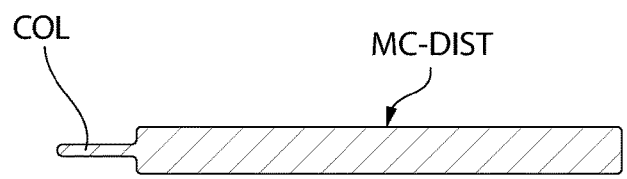
FIG. 10V is a cross-sectional view of the PSD Insert taken along line 10V-10V of FIG. 10S.
Figure 10W:
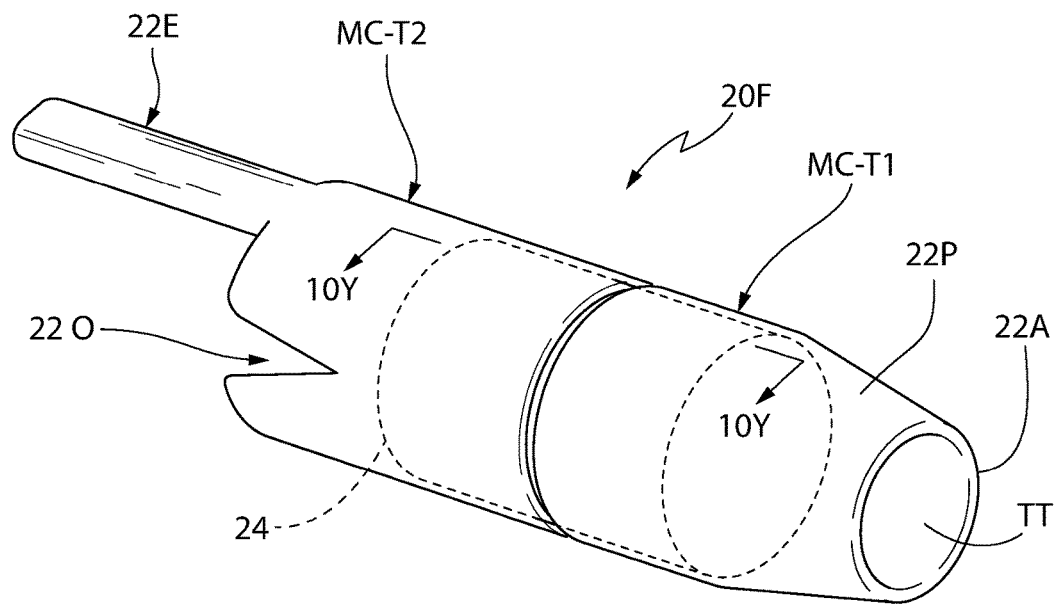
FIG. 10W is an isometric view of another PSD embodiment referred to as the "PSD Telescope" wherein the main component comprises two distinct portions that can slide over the internal component.
Figure 10X:
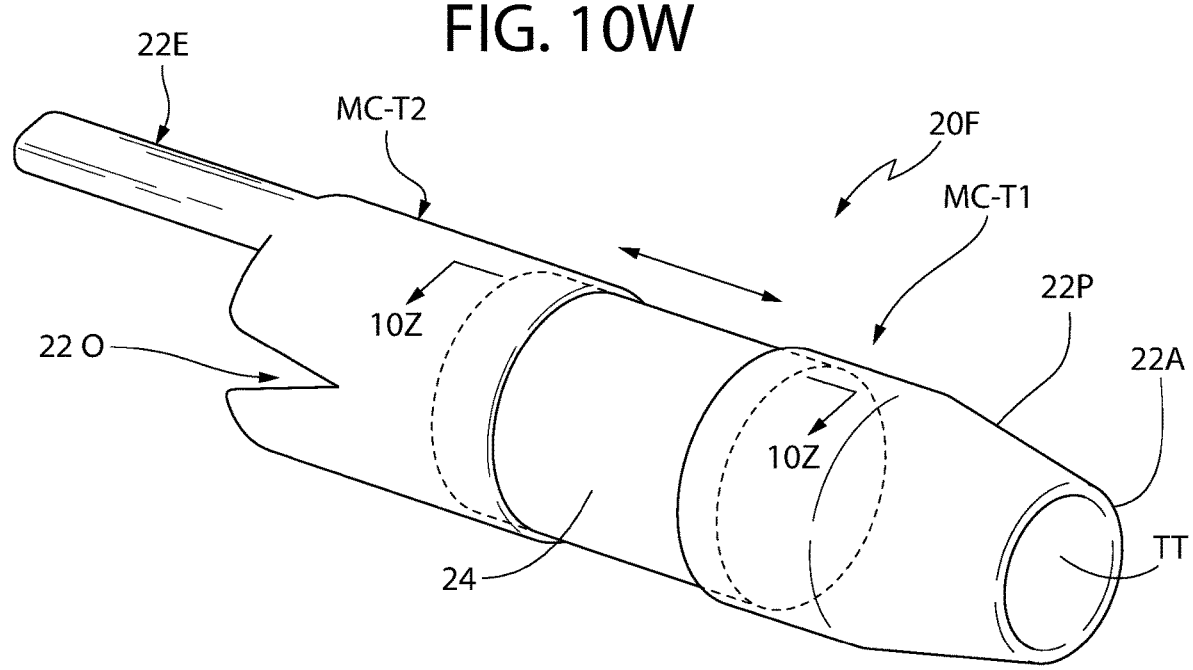
FIG. 10X is an isometric view of the PSD Telescope shown with the two distinct portions displaced away from each other, exposing the internal component.

As will be discussed in detail below, a penile sleeve device (PSD) is configured for implantation in the subcutaneous space of a patient's penis and is designed to enhance and/or correct penis shape and size, treat low to moderate level erectile dysfunction, and correct penis curvature and malformation. Several different embodiments of the penile sleeve device are disclosed herein:

| Penile Sleeve Device | Sample FIG. | Reference Number |
|---|---|---|
| PSD-smooth | FIG. 2I | 20 |
| PSD-S-fold | FIG. 2K | 20A |
| PSD-wavy-fold | FIG. 2J | 20A1 |
| PSD-Tight-S | FIG. 2L | 20A2 |
| PSD-Collapsible | FIG. 10F | 20B |
| PSD-Volume Shift | FIG. 10I | 20C |
| PSD-Spoke | FIG. 10Q | 20D |
| PSD-Insert | FIG. 10S | 20E |
| PSD-Telescoping Design | FIG. 10X | 20F |
| PSD-Fused | FIG. 2G | 20 |
| PSD-12 Inch | FIG. 10 | 20A |

The PSD-smooth 20 referred to simply as "PSD 20" will be discussed initially to explain the overall penile sleeve device construction and use. The designator "PSD-smooth" 20 refers to the outer and inner layers of the main component 22 (to be discussed in detail later) which comprise "smooth layers." However, it should be understood that the preferred embodiment of the penile sleeve device is the PSD-S-fold 20A and its variations, PSD-wavy-fold 20A1, and PSD-Tight-S 20A2.

PSD 20: General Structure and Shape

The penile sleeve device (PSD) 20 is an implantable sub-cutaneous penile shaft silicone rubber device. The PSD 20 comprises a plurality of parts. The PSD 20 has multiple potential functions. The first, or primary function, is to elongate the penile shaft PS in the flaccid or/and erect states whereby depict a normal penis P in a flaccid state (FIG. 8H) as compared to a penis having the PSD 20 implanted therein (FIG. 8I). A secondary function is to increase the girth of the penile shaft in the flaccid and erect states whereby (FIG. 8F) depicts a normal penis girth as compared to a penis having a PSD 20 implanted in a penis and formed to enhance penile girth EPG (FIG. 8G). A third function is to harden or increase firmness of the penis, allowing for a harder or firmer erection, which assists in patients with mild or moderate forms of erectile dysfunction. A fourth function is to straighten a curved penis. For example, a penis may have a natural curvature or may have a curvature due to a pathological state, such as is seen in Peyronie's Disease, which is shown in FIG. 8J. In particular, internal plaque (PLQ) causes the penis with Peyronie's Disease PPD to misshape as shown in FIG. 8J. By implanting the PSD 20 of the present invention, the curved penile profile can be partially or fully corrected (FIG. 8M), while also increasing penile girth (FIGS. 8K-8L). The fifth function is to custom shape the penis. A patient may want a much thicker proximal base area, or some built in "bumps" 22G, or a large veiny look 22F, etc.

As mentioned above, the PSD 20 has multiple functions, such as to elongate, thicken, harden, straighten, and custom shape the penis. Any one of, or a combination of, these functions can be achieved with the PSD according to the patient's desires. These functions may be achieved using multiple PSD structural forms, with only minor alterations. To achieve these variations a two-part PSD design, is used in most, if not all, applications. There will be additional minor parts to the PSD, however, there will be two major parts, the main component and the internal component, to be discussed later. The other design variations include: the PSD-Smooth 20, PSD Wavy-Fold 20A1, PSD Tight-S 20A2, PSD: Collapsible 20B, PSD Volume Shift 20C, PSD: Spoke 20D, PSD: Insert 20E, PSD: Telescoping Designs 20F, PSD: Fused, and PSD: 12-inch. These alternate design variations will fulfill the same objectives as the PSD. As will be discussed below, the PSD comprises a two-part design. Variations in size, shape, length, and thickness of each part assists in accommodating for most if not every flaccid and erect clinical scenario encountered.

PSD: General Structure

The PSD comprises two main parts (FIG. 2G), an outer tubular section or Main Component (MC) 22 and an inner partial tubular section or Internal Component (IC) 24 such that when they are coupled together, they effectively form a 'tri-layer tube' on the dorsal lateral sides, and a 'bi-layer' tube on its ventral side. This can be seen most clearly in FIG. 1H. The Main Component (MC) 22 (FIGS. 1L-1Q) is an elongated member comprising a distal end 22A, a medial ventral area 22B, a medial dorsal area 22C, and a proximal end flange 22E. The Internal Component 24 (FIGS. 3-3B) is an elongated member comprising a distal end 24A, a body portion 24B, proximal end of the Internal Component proper 24C, and a proximal end flange 24D. The proximal end flange 24D of the Internal Component 24 and the proximal end flange 22E of the Main Component 22, when both flanges are put together to make the completed PSD 20. This combined "flange" areas of the Internal Component 24 and Main Component 22 is called the Proximal Double Flange End (FIG. 2A). The Internal Component 24 has a C-shape (e.g., FIGS. 3A-3E), being open along a "ventral" (under) side, as opposed to its closed dorsal (top) side. The Main Component 22 is the component that is in direct contract with penile tissues. The Internal Component 24 is not in direct contact with any penile tissues but is located within the Main Component 22, as will be described in detail later. Both components 22/24 are used in most applications of the PSD 20 to meet the patient's needs and desires.

PSD: Main Component 22

The Main Component 22 comprises a moderate to high flexible and stretchy silicone rubber elastomer. One of the main functions of the Main Component 22, which is in direct contact with the penile tissues, is to work in combination with the Internal Component 24 (which is not in direct contact with the penile tissues) and provide a soft, safe, and non-irritating interface between the PSD 20 and the penile tissues. Other functions of the Main Component 22 aid in keeping the penis outstretched in the flaccid or erect states and provides additional girth, if desired, as well. The Main Component 22 provides low to moderate firmness, and plays a moderate role in structural support, curvature corrections, and adding additional "hardness" for erectile dysfunction issues. The Main Component 22 provides that critical non-irritating interface between the PSD 20, as a whole, and the penile tissues (shielding the harder Internal Component 24 from the penile tissues and thereby eliminating potential penile tissue irritation). The Main Component 22 is simply too flexible in nature to fully assist in the structural support functions, and that is why a harder, more firm part, the Internal Component 24, is needed. The Main Component 22 can be molded into a variety of shapes such as adding a veiny look 22F, or adding some "bumps" 22G, etc., as shown in FIG. 1.

The Main Component 22 has several functions. Its primary function it to stabilize the out-stretched penile shaft maintaining an extended flaccid and/or erect length. It helps prevent the penile recoil forces from retracting to a smaller flaccid or erect state. The mechanism by which the Main Component 22 extends the penile shaft is two-fold. The Main Component 22 provides inwardly-directed radial force $F_{RI}$ directly on the penile fascia, gripping and holding it "in place" in an out-stretched position. Secondly, the Main Component 22, which abuts the pubic boney area proximally and is mounted in place distally with sutures, acts to physically hold the out stretched penis in position, like a splint. This mechanism allows the penile fascia and penile shaft to remain out-stretched during the flaccid and erect states.

The Main Component 22 is designed with soft silicone material to interface with the penile tissues. This material aspect of the device is critical in providing the least amount or the total elimination of tissue irritation and thus greater patient comfort for long term use. Using this type of material as an interface, with the additional design features such as soft rounded edges, balanced non-excessive inwardly-directed radial forces $F_{RI}$ exerted, and great flexibility lowering tissue tension upon penile bending and stretching, provides sound medical design safety features for patient comfort and long-term use.

Additional alterations to the Main Component 22 include thickening to provide additional girth, hardening to provide additional firmness and straightening, and custom molding to provide veins 22F, bumps 22G, or asymmetrical penile shaft shapes can be made as needed.

The anatomic location or placement of the Main Component 22 is in the subcutaneous space of the penile shaft, and in direct contact with the penile tissues. The PSD 20, specifically the Main Component portion 22, lies directly on top of Buck's and Tunica Albuginea Fascia and touches the subcutaneous (viz., undersurface of the) skin.

The Main Component 22 is in contact with the tissues, so medical safety considerations are needed such as the device being soft/semi-soft in durometer, very stretchable and elastic (to allow for the erection expansion process and low tension upon penile bending, pulling, etc.), smooth, rounded in all areas to prevent tissue trauma or irritation, and having an acceptable safe long-term biomaterial. The material of choice, medical grade silicone, which can be manufactured as a very stretchable and elastic product, allows for unimpeded blood flow into the penile shaft during the erection process due to its elastic characteristics. This material also elicits the foreign body reaction and results in a collagen envelope which will surround the entire PSD 20 over a short period of time. This is advantageous because it promotes stability, providing a tethering down of the PSD 20, but also provides a protective "cocoon" and prevents the immune system from trying to chemically break down the PSD 20.

The MC 22 will have some assistance in expanding by the outwardly-directed radial force of the Internal Component (IC) 24 (as discussed below).

The MC 22 is formed from a single mold. The IC 24 is formed from a single mold.

The MC 22 thickness varies from 1-20 mm, but is relatively high in most cases, as compared to the IC 24 thickness (ranging from 1-10 mm).

Both the MC 22 and the IC 24 are manufactured in specific lengths. MC 22 sizes range from 3 inches (measuring the length of the erect penis on the ventral side), with 0.5-inch incremental increases up to 12 inches in length. IC 24 sizes range from 2.0 to 11.5 inches with 0.5-inch incremental sizes.

The MC 22, in most cases, is designed to be used with the IC 24. The reason for this combination of components is to assist the more "fragile/soft" MC 22 with structural support provided by the IC 24. This additional structural support by the IC 24 helps prevent the MC 22 from buckling, bending, and bowing, and, in addition, provides firmness ("erection firmness"), and prevents unwanted folding upon itself (e.g. like forming a shirt sleeve cuff) at the proximal or distal ends.

As shown most clearly in FIG. 1H, the MC 22 is a combination bilayer 22S and single layer 22W. The MC 22 on its dorsal (top side) and lateral sides is a bilayer 22S. The MC 22 on its ventral side (bottom side) is a single layer 22W. The MC 22 on its very distal and very proximal areas are a single layer 22W. The bilayer area 22S is composed of an inner layer 22S1 and an outer layer 22T1. This bilayer forms a space or "pocket space" 22I (FIG. 2G) between the inner layer 22S1 and the outer layer 22T1. This pocket space 22I is designed to house the IC 24 as shown in FIGS. 1H and 2G. This pocket space 22I extends within the Main Component to certain points distally, proximally, dorsally, and ventrally.

The MC 22 comprises the pocket space 22I which extends within the MC bilayer 22S a certain distance from dorsal to ventral, and distal to proximal, as shown in FIG. 2G. The IC 24 is placed within this pocket space 22I through a slit like opening of the MC 22 called the dorsal mid-line slit (22J). The pocket space 22I has near identical dimensions as the IC 24, because the union of these two elements, the pocket space 22I and IC 24, are to fit like a 'hand in a glove', the hand representing the IC 24, and the glove, representing the pocket space of the MC 22. These two components, 22/24, once positioned, are held together in place (FIG. 2G); In addition, the pocket space 22I of the MC 22 extends into the MC 22 proximal end flange 22E. This portion of the pocket space 22I that is in the MC proximal end flange 22E accommodates for the Internal Component proximal end flange 24D. When the IC 24 is positioned within the MC pocket space 22I, the two units, now forming the PSD 20 in total, will be stable and act as "one" unit functionally.

The IC 24, once placed within the pocket space 22I of the MC 22, will exert a mild outwardly-directed radial force ($F_{RO}$, see FIG. 1I) on the MC 22. This outwardly-directed radial force $F_{RO}$ will counteract the inwardly-directed radial force ($F_{RI}$, see FIG. 1I) exerted by the MC 22. The MC 22, with its pocket space 22I, resists and stabilizes the IC 24's potential outwardly-directed radial force $F_{RO}$, thereby preventing the IC 24 from expanding unopposed. This feature of the IC 24 exerting an outwardly-directed radial force, $F_{RO}$, (see FIG. 1I), helps the PSD 20, in total, with regard to minimizing the overall inwardly-directed radial force $F_{RI}$ onto the penile tissue and thereby does not impede the blood flow into the penile tissues during the erection process. In other words, the outwardly-directed radial force $F_{RO}$ exerted by the IC 24 reduces on the MC 22's inwardly-directed radial force $F_{RI}$ (see FIG. 1I) and takes the stress off the erection inward blood flow pressure process.

Even though the MC 22 is made of soft, flexible, compressible, and expandable material, a "buckle space" 22L is designed in to allow additional "slack" and "compression", if needed, during penile bending, pulling, etc.

Even though the MC 22 is, in most instances, used in conjunction with the IC 24, there may be certain circumstances where the flaccid retraction force is minimal and use of only the MC 22, without the need for extra structural support from the IC 24, may provide the clinical results desired.

As mentioned previously, the MC 22 outer layer 22T1 may also be textured to provide a desirable look and feel. For example, patients may want a "veiny" look 22F (FIG. 1) to the penile skin surface. This veiny look 22F can be accomplished by adding such a texture profile to the mold design. Alternatively, or in addition, the MC 22 can be supplemented to have "bumps" 22G (see FIG. 1). On the other hand, where a permanent filler is used (viz., around the outside of the implanted PSD 20) to thicken the penile skin (e.g., to increase girth), the veiny texture 22F and/or bumpy texture 22G might be obscured.

Figure 5:
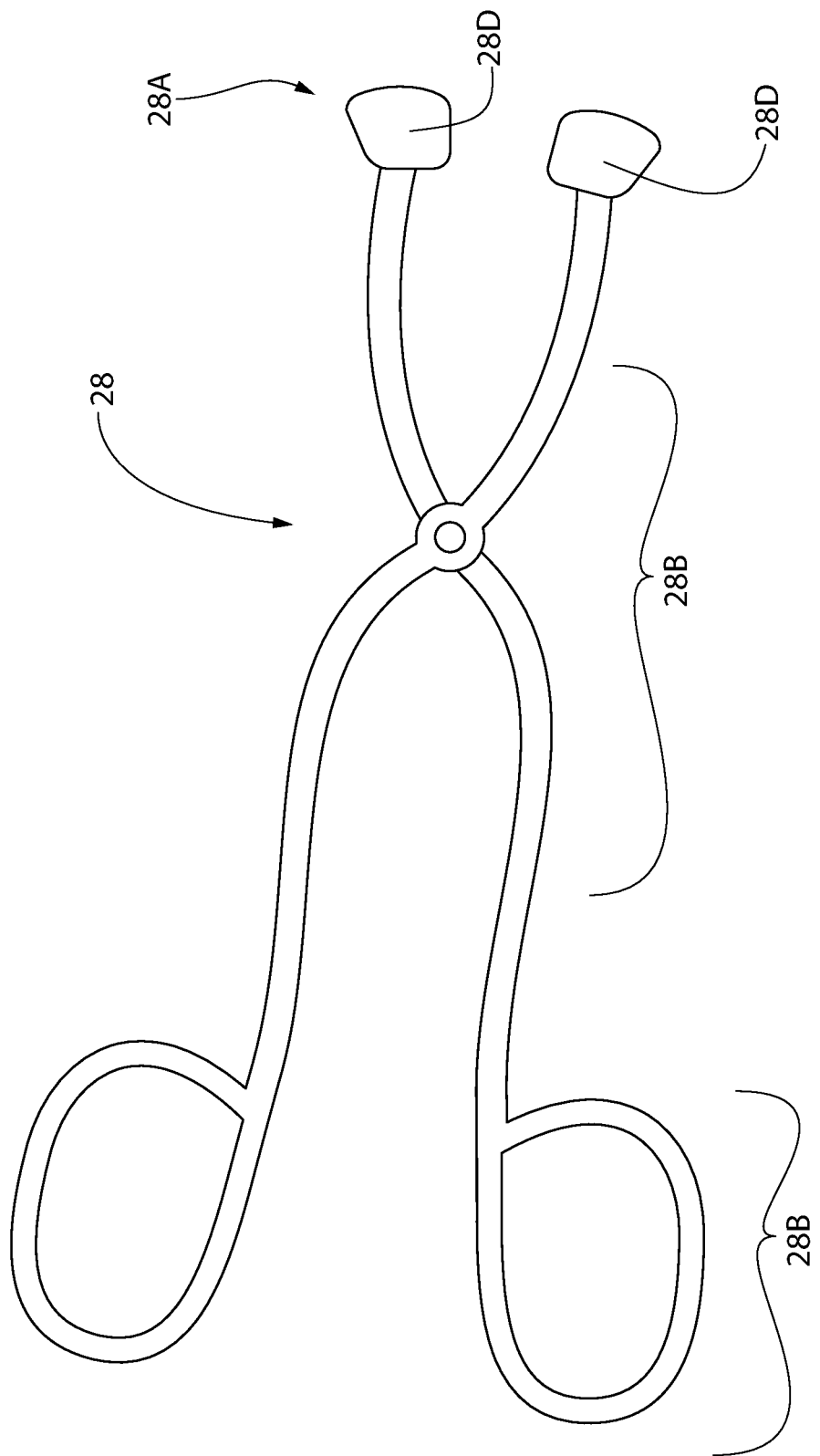
FIG. 5 is a plan view of an exemplary glans gripper device used for grasping the penis glans during PSD implantation.
Figure 5A:
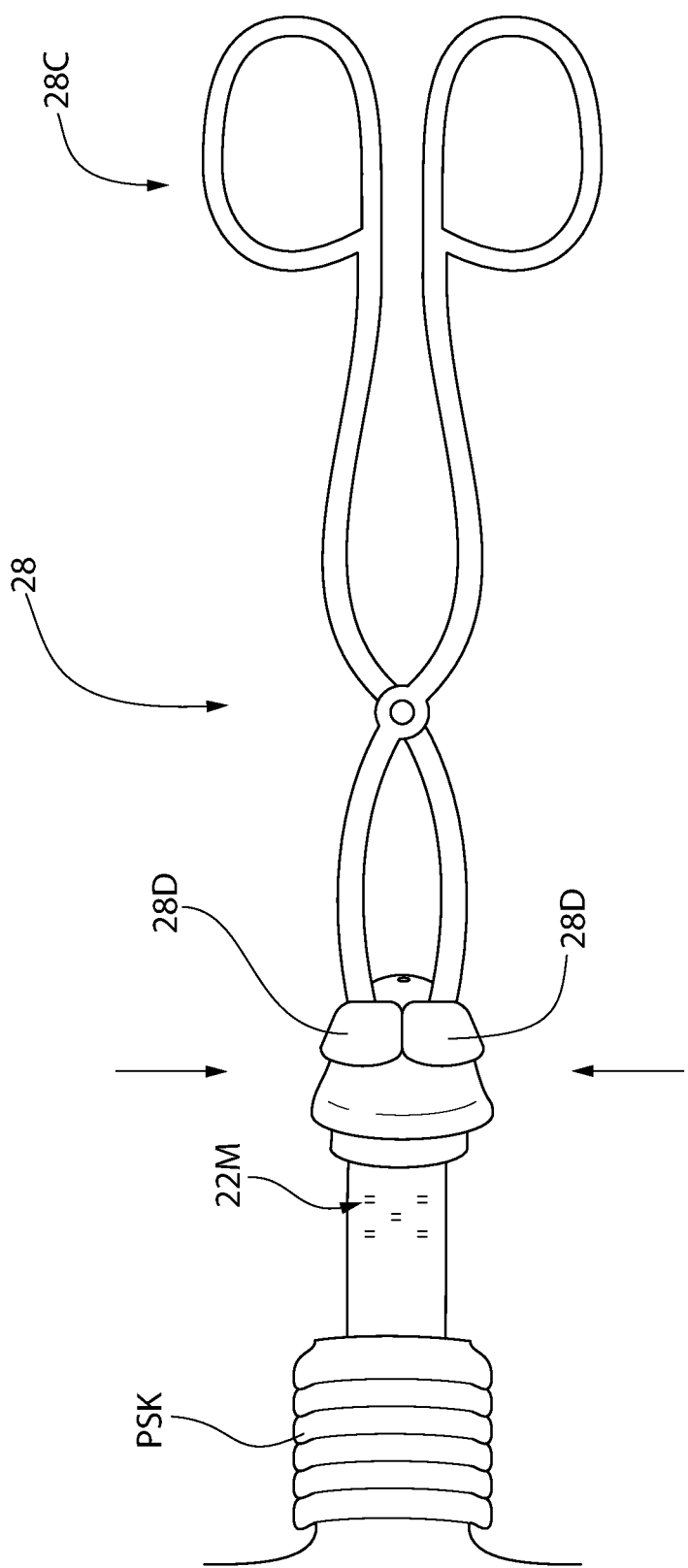
FIG. 5A depicts how the glans gripper device grasps the penis glans following degloving of the penile shaft.

Suture anchor locations 22M (FIG. 5A) on the penile tissue will be determined by using a marker pen. The PSD 20 will be placed into position, the penile shaft will be artificially erected, and the marker pen will be placed through suture anchor slits 22N (in the inner layer 22S1 of the MC 22, FIGS. 2B-2C) and 24G (of the IC 24, FIG. 3) of the PSD 20 to mark the suture anchor locations 22M locations on the penile tissue. On occasion, additional suture anchor areas will be needed to secure the PSD 20, and, in particular, when penile retraction forces are very high, especially in the case of moderate penile length shortening the flaccid state, and PSD 20 placement for lengthening during the non-erect state. Considering this, multiple or additional mounting locations on the proximal and mid-shaft regions of the penile shaft may be necessary to divert excessive force which may be transmitted to the Glans Coronal area from the recoiling of the penile shaft and causing a distal shifting of the PSD 20 onto that area. Optional distal, mid-shaft, and proximal, suture anchor slits 22NA (in the inner layer 22S1 of the MC 22) and 24GA (in the IC 24, FIG. 3) in the PSD 20 will be available, if additional support is needed.

As mentioned previously, the MC 22 comprises a pocket space 22I extending from dorsal to lateral sides, and proximal to distal sides, including into the proximal end flange of the MC 22. This pocket space 22I houses the IC 24. This "hand-in-a-glove" fit between the MC pocket space 22I and the IC 24 prevent or limit movement of the IC 24 within the pocket space 22I of the MC 22.

Figure 9:
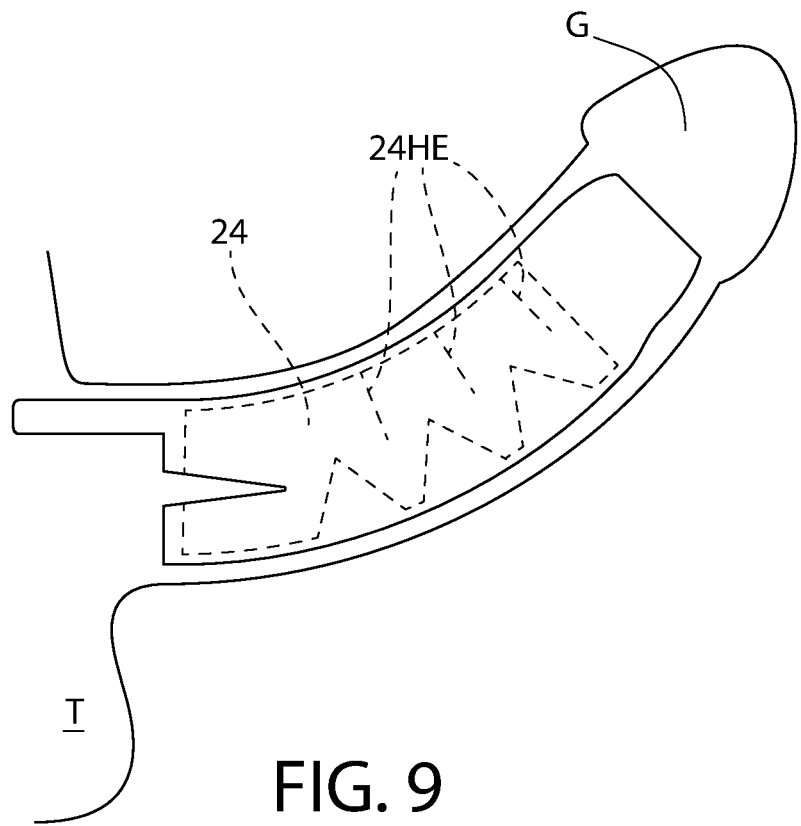
FIG. 9 is a functional diagram showing how the dorsal cuts close while the ventral cuts open in the internal component (shown in phantom) of the PSD when the penis is moved in an upward direction.
Figure 9A:
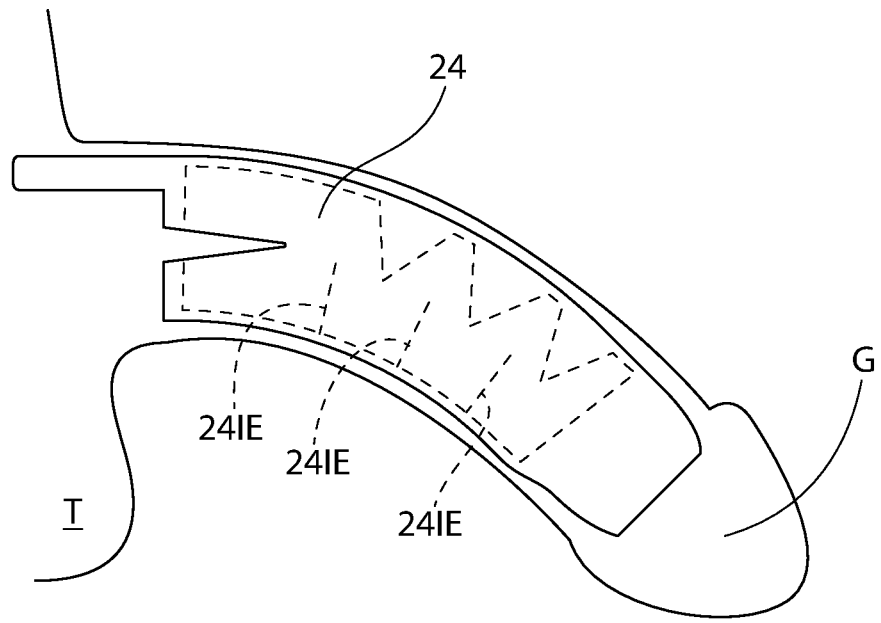
FIG. 9A is a functional diagram showing how the dorsal cuts open while the ventral cuts close in the internal component (shown in phantom) of the PSD when the penis is moved in a downward direction.

During movement of the penile shaft, whether it be from sexual intercourse, or movement within underwear, etc., the PSD 20's two components 22/24 will slide on one another internally. For example, as most clearly in FIGS. 3 and 9, during dorsal or upward bending motions, the IC 24 comprises a plurality of dorsal V-cuts 24H having edges 24HE that will approximate and close the V-cuts 24H. Similarly, as most clearly in FIGS. 3 and 9A, during ventral or downward bending motions, the IC 24 also comprises a plurality of ventral V-cuts 24I having edges 24IE that will approximate and close the V-cuts 24I. For either of approximation to occur, the V-cut edges 24HE need to move closer together and therefore "slide" against the inner surface 22T2 (FIG. 1H) of the MC 22's outer layer 22T1 as well against the outer surface 22S3 of the MC 22's inner layer 22S1 (FIG. 1H). This "'sliding" of the IC 24 within the pocket space 22I may cause friction and thus wear and tear of the surface material. As shown most clearly in FIG. 2A, to eliminate the potential wear and tear of the IC 24 rubbing against the internal surfaces of the inner 22S1 and outer 22T1 layers of the MC 22 during penile bending motions, a layer of lubrication L-Lube (e.g., silicone oil) may be positioned within the pocket space 22I of the MC 22 which will allow for easy sliding and much less friction of the IC 24 within the MC 22.

The proximal lateral areas, bilaterally, of the MC 22, further comprises a proximal lateral V-cut 22O (e.g., FIGS. 1N and 1O), the purpose of this V-cut 22O is to allow for the proximal ventral portion of the PSD 20 to bend when the penile shaft is bending in a ventral direction. The V-cut 22O will provide "give" or move in a ventral direction decreasing the force of the PSD 20 proximal ventral area from pressing on ventral penile anatomic structures, such as the urethra, thus eliminating direct force and potential irritation of the penile tissues.

The distal end 22A of the MC 22 comprises a tapered end 22P to provide a comfortable interface against the glans when placed, and for a subtle cosmetic tapering or narrowing as the PSD 20 approaches the sub-glans area.

PSD: Internal Component 24

The IC 24 comprises a much higher durometer silicone rubber material with the possible addition of a plastic and/or malleable metal alloy. Depending on the amount of hardness needed, high in the case of treating low to moderate levels of erectile dysfunction (ED) and moderate to high levels for erect lengthening needs, the IC 24 can be made of many types of materials and combinations of materials. The type of materials include but are not limited to metal malleable alloys, plastic or resin materials, silicone rubber materials with varying durometers, or any combination thereof. The IC 24 is the portion of the PSD 20 that provides the main structural support in keeping the penis outstretched in the flaccid and erect states, helps correct penile curvatures, and assists in providing additional hardness in ED issues. The IC 24, by its simple volume, provides some girth. The IC 24 plays a significant role in treating erectile dysfunction, considering it can provide hardness and the ability to be bent upwards (erect state) and then bend downwards (for the flaccid state) via the malleable alloy component. An additional internal component 24J (FIG. 10A) can be added to provide additional support in cases of moderate curvatures.

The IC 24 has several functions. Considering the potentially high retraction forces involved with an out-stretched non-erect flaccid and/or erect penis, the IC 24 provides the necessary structural support for preventing penile retraction and for preserving the MC 22 shape and integrity. The IC 24 also prevents the more fragile flexible/stretchy MC 22 from folding on itself (e.g., such as a shirt sleeve rolling up or folding upon itself, especially at the distal end), prevent buckling, and prevent bowing outwards (like an accordion effect).

The anatomic location of the IC 24 is directly within the bilayer space, or pocket space 22I of the MC 22. Since the IC 24 is partially tubular, with a C-shape, it does not extend to the ventral surface of the MC 22. The IC 24 is not in direct contact with any penile tissues. The MC 22 comprises a dorsal mid-line slit 22J, acting as the "doorway entrance point" to allow the IC 24 to be placed into the pocket space 22I; once inserted, the IC 24 is no longer visible after the dorsal mid-line slit 22J is reapproximated and closed. As is seen most clearly in FIGS. 2-2A, the dorsal mid-line slit 22J closes with a special tongue 22JT and groove 22JG closure to "seal" this slit shut; this includes preventing liquids or lubrication (e.g., L-Lube mentioned previously) from exiting through the slit 22J. Both the MC 22 and the IC 24, when joined together as one unit, are placed in the subcutaneous space of the penile shaft, on top of Buck's and Tunica Albuginea Fascia and under the penile skin (see FIG. 8D, for example).

The IC 24 provides the MC 22, as well as the two-part unit as a whole (PSD 20), with a hardening or firming effect during the flaccid and erect states, since the durometer (or hardness) of the IC 24 is much higher. The IC 24 has mild to moderate stretch-ability. The IC 24 also helps counter penile curvature forces and assists in the straightening of the penile shaft. The IC 24 will provide some thickening of the penile girth as well, if needed.

As in the MC 22, the IC 24 also includes a proximal lateral V-cut 24E (FIG. 3) which aligns with proximal lateral V-cut 22O of the MC 22 when the tubular sections are coupled together. Similarly, the IC 24 also comprises a buckle zone 24F (FIG. 3) that aligns with the buckle zone 22L of the MC 22 when the two components are assembled. Moreover, the IC 24 further comprises suture slits 24G near the distal end 24A that also align with the suture slits 22N of the MC 22 when the two components are assembled. Additional suture slits 22NA/24GA may be located at the mid-shaft and proximal areas of the PSD 20.

Figure 3:
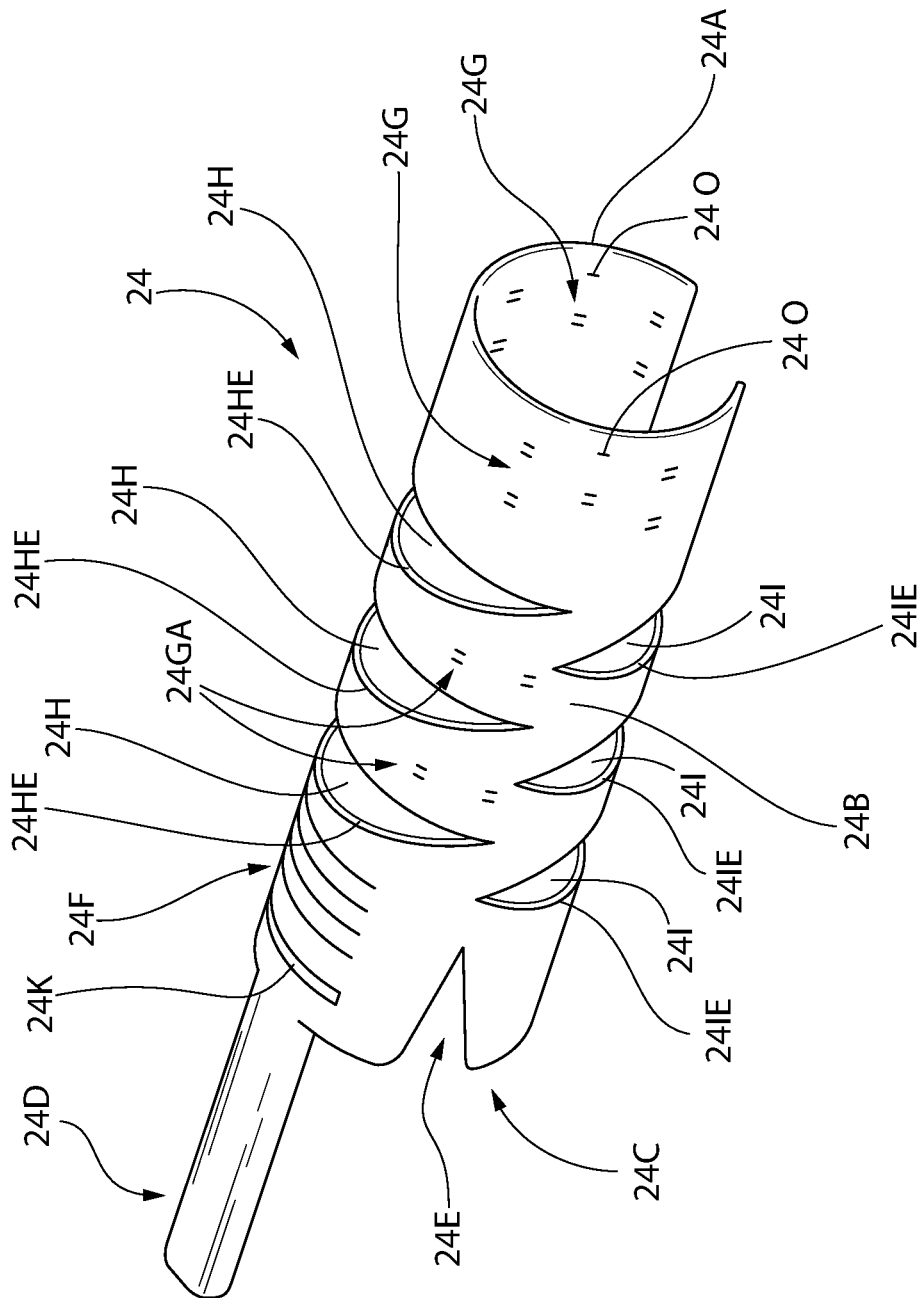
FIG. 3 is an isometric view of the internal component of the PSD.

As can be most clearly seen in FIG. 3, the dorsal side of the IC 24 may comprise a plurality of dorsal V-cuts 24H. The purpose of the plurality of dorsal V-cuts 24H is to permit dorsal bending of the PSD 20 such that the IC 24 can "collapse" (and not lengthen with dorsal bending) without requiring the proximal end flange 24D to displace any further within the MC 22's proximal end flange pocket 22Q (FIG. 2G), and thereby place or transmit excessive pressure on the bony and ligamentous structures in the pubic space/pocket (see FIG. 8E). The ventral side of the IC 24 may comprise a plurality of ventral V-cuts 24I. The purpose of the plurality of ventral V-cuts 24I is to permit ventral bending of the PSD 20 such that the IC 24 can "collapse" and limit its proximal lengthening or movement and thus limit or eliminate any pressure exerted by the IC 24 end flange 24D, and to prevent the ventral portion of the PSD 20 to move in a ventral or ventral-proximal direction.

The IC 24 will also have optional "piping" 24N (FIGS. 3D-3E) on the inner and/or outer surfaces thereof. The piping will be made of the same silicone material and durometer as is the IC. The piping 24N will be elevations, about 1 mm high and rounded, and run the course, longitudinally, to the IC 24's proximal to distal end. This piping 24N will be separated by 4-10 mm apart. The inner surface and outer surface piping 24N will be "staggered" and not be aligned or place "on top" of each other (see FIG. 3E). This piping 24N will provide structural support for the IC 24 and provide less surface area for the IC 24 to interact with the MC 22. Less interaction will limit wear and tear as these two components slide and rub on one another. This piping 24N design may eliminate the need for lubrication as well. It should be understood that the dorsal V-cuts 24H, ventral V-cuts 24I and the buckle zone 24F are omitted in FIG. 3E for clarity only but could also be included therein.

The MC 22, IC 24, and associated minor components such as the sutures S, suture clips 80, T-Device 30 (all of which will be discussed below), etc., work together to provide for delivery of the PSD 20 and for PSD 20 functionality. In addition, these components are designed not only for certain functions, such as flaccid and erect lengthening, girth enlargement, curvature correction, erectile dysfunction 'hardening' assistance, and different custom cosmetic designs and shapes, as desired by the patient, but also designed for medical safety which includes the very materials used as well.

The MC 22 and IC 24 are manufactured in specific predetermined lengths, diameters, and special features. Specific lengths and internal diameter sizes are clinically superior, or advantageous, such as having incremental sizes with lengths ranging from 3.5 inches, with 0.5-inch incremental increases up to about 12 inches in length. It should be noted that the IC 24 is approximately 1 to 2 inches shorter than the MC 22 length. Additional manufacturing variables include various internal diameter sizes to fit patients with low to high penile shaft girth sizes, multiple durometers and girth sizes, multiple material types, and custom options as well.

Figure 3A:
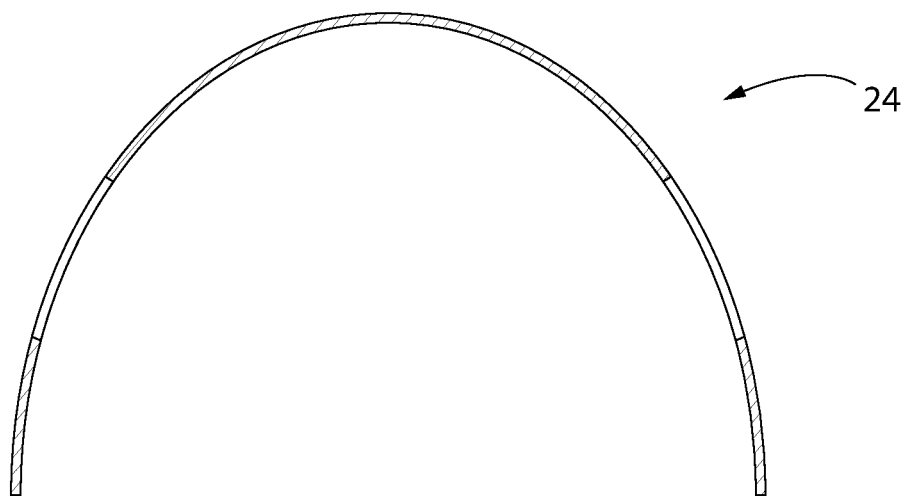
FIG. 3A is an end view of the internal component in an uncompressed state.
Figure 3B:
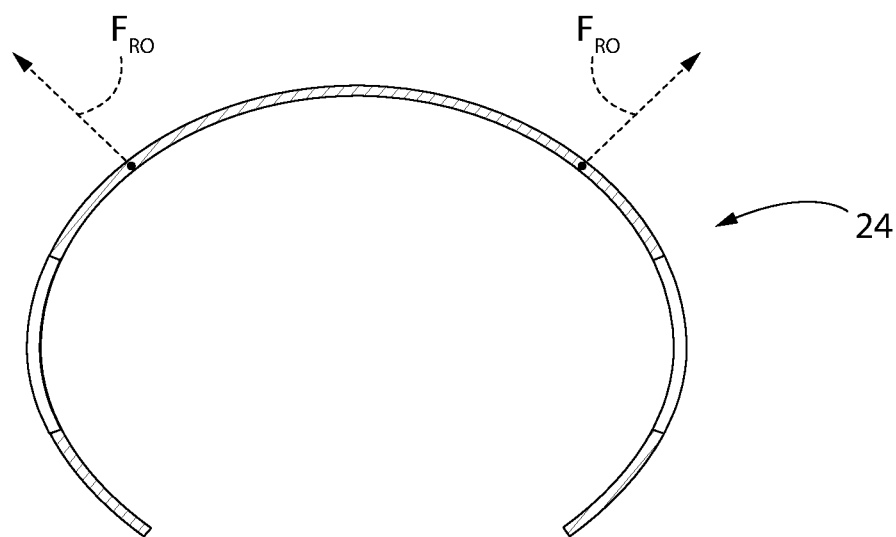
FIG. 3B is an end view of the internal component in an inwardly compressed state.
Figure 3C:
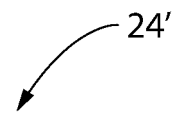
FIG. 3C is an alternative internal component whose initial state is a planar configuration.
Figure 3D:
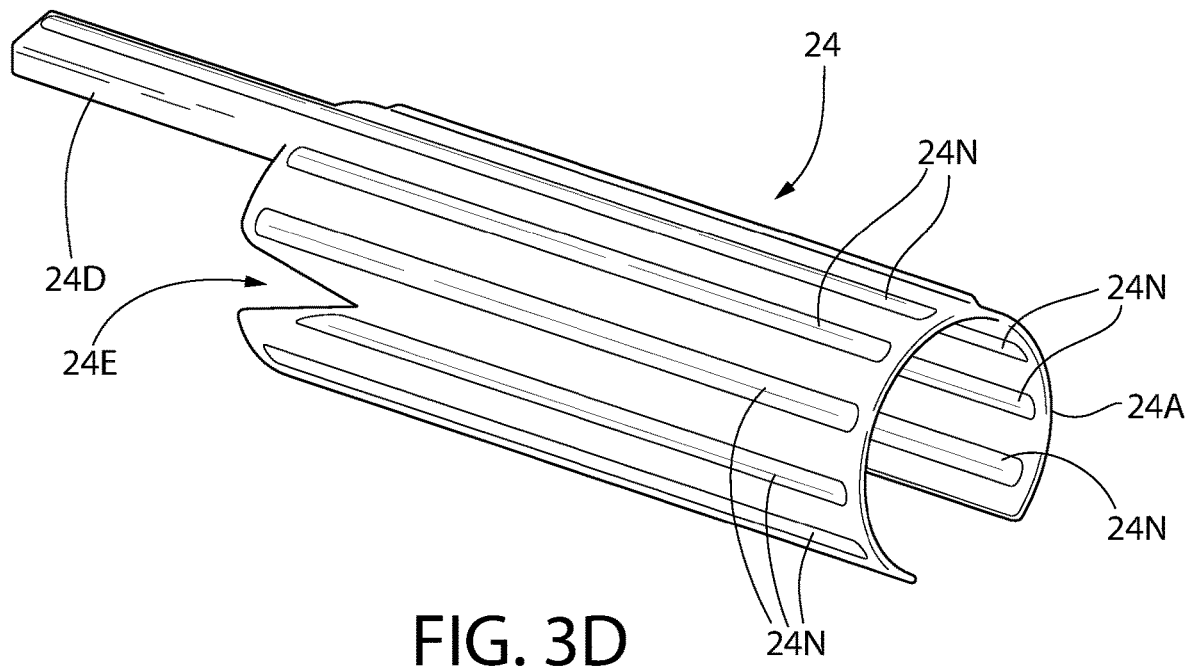
FIG. 3D is a further alternative internal component, similar to the internal component of FIGS. 3A-3B but having longitudinal piping running along its exterior and interior surfaces.
Figure 3E:
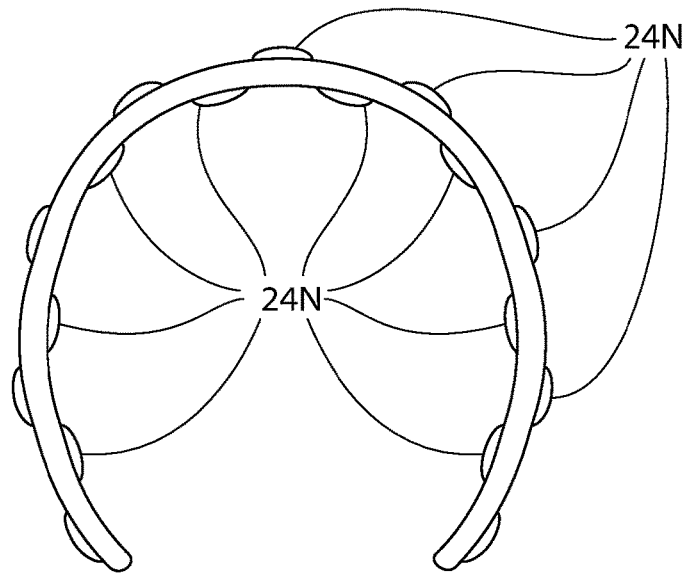
FIG. 3E is an end view of the internal component of FIG. 3D.

As mentioned previously, the IC 24 is shaped like a tube but is an incomplete tube, being open on its ventral side, a C-shaped tubular structure (see FIGS. 3A-3B). This opening of the "C" shaped tubular structure not only allows for expansion during an erection, but does not place pressure on the urethra, directly or indirectly, which is anatomically located on the ventral mid-line area of the penile shaft. This C-shaped configuration is also referred to as "open tubular section." In addition, the IC 24 is manufactured with a larger diameter opening, or even as a flat sheet (FIG. 3C), unlike the tubular shape of the MC 22. As discussed earlier, the IC 24 fits into the pocket space 22I of the MC 22; however, the IC 24 will need to be completely folded/rounded, in the case of a flat-manufactured sheet 24' (FIG. 3C), or partially squeezed closed (FIG. 3B), in the case of a circular-manufactured form, to get it to align and fit into the MC pocket space 22I. As such, the IC 24 is designed to be elastically deformable, and once elastically formed into the desired shape, it will provide outwardly-directed radial force $F_{RO}$ once placed into the MC pocket space 22I. Thus, the IC 24 is always expanding outward, due to it being folded, and this outwardly-directed radial force $F_{RO}$ assists in the outward expansion of the PSD 20 during an erection.

There are many differences between the IC 24 and prior art penile implants. In particular, these prior art penile implants comprise a single part device, providing both penile length and/or girth, having a relatively high durometer, or hard, and this hard device is in direct contact with the penile tissues. The direct contact with penile tissues does, in most cases, results in undesirable pressure points. These types of penile implants transmit stress, through these pressure points, directly to the penis glans, sub-glans tissues, penile shaft fascial tissues, and pubic ligament and bony tissues, which may result in tenderness and pain (considering the penile recoil forces on the device). Chronic exposure of the penile tissues to these pressure points can cause skin inflammation and even result in the necrosis of the skin and rupture of the device through the skin. In contrast, the high durometer IC 24 is not in direct contact with the glans, sub-glans or any penile tissues, but rather only the very soft low durometer MC 22; and it is only the much softer MC 22 that is in direct contact with penile tissues. The IC 24 provides certain functions such as hardness, counters the penile retraction forces, supports the MC 22, and provides some girth, while the MC 22 provides a safe cushion interface between the IC 24 and with the penile tissues, and also provides counter penile retraction forces and girth. This combination of parts provides for tissue comfort, an acceptable external cosmetic "feel" when in the flaccid and erect states, and minimizes or eliminates tissue irritation, tenderness, pain, and possible skin rupture.

In addition, the MC 22 and the IC 24 are designed to alter shape with penile bending. While the penis bends, the device is designed to "bend with" the penis preventing device pressure points on the penile tissues and skin. In contrast, some prior art penile implants are made of relatively hard materials and are not only not able to bend freely, but nearly prevent the natural bending, in any direction, of the penis in the flaccid or erect states. Considering the non-flexibility of these other devices, any bending of the penile shaft causes the hard device to "dig into" the penile tissues. This digging into the penile tissues, or causing pressure points, is due to the non-bending of this hard-rigid structure causing direct high pressure on the penile tissues and skin. This inability to not shorten during bending motions simultaneously with the penile shaft bending (which will collapse and shorten when bent), will result in proximal and distal excessive pinpoint pressures on penile tissues, especially near the glans, penile skin, and at glans and pubic pocket areas. This excessive pinpoint pressure may result in irritation and possible tissue necrosis (tissue death). The same pressure points will be observed with any penile bending or even an up or downward motion experienced during intercourse. This rigid, non-bending type of device placed into the penile tissues and skin has the potential for major issues, such as being a major source of irritation, inflammation, pain, and skin erosion with the potential for the device to break through, literally through, the skin.

In contrast, the IC 24 is not in direct contact with the tissues, which is a key medical safety design.

The IC 24 position allows for a much higher durometer (hardness) to be used since the IC 24 is in direct contact with only the softer MC 22 only, and not the penile tissues directly, especially at the proximal and distal ends where most of the stress is applied from the retraction forces.

The IC 24 is formed from a single mold.

The IC 24 is made from a medium to high durometer silicone elastomer, with the potential of additional elements such as plastic, resins, and/or malleable metals.

The IC 24 does not provide significant girth or penile shaft thickness, but in certain circumstances it can, if needed.

The IC 24 can fold upon itself, but not easily, like the MC 22, due to its higher durometer As described previously, the IC 24 is designed to be used with the MC 22. The IC 24 cannot be used independently because such a use would cause the same potential issues as described previously with regard to prior art penile implants, such as pressure sores, pain, skin ulceration, and penetration of the device through the skin.

The IC 24 may not be needed in certain circumstances, such as in the case where the flaccid retraction force is minimal and a MC 22 only treatment may be appropriate.

The IC 24 comprises multiple suture slit locations 24G/24GA as does the MC 22, since the anchor slits 22M, and subsequent sutures placement, need to go through both components. The reason for additional suture slit locations is because of the possibility that the retraction forces are very high, especially in the case of optimal erect lengthening. Considering this potential high force generation by the retraction of the penile tissues, multiple suture anchor locations may be necessary to not only divert excessive force directly onto the glans corona/rim and other areas of the penile shaft if needed, but also to prevent excessive force onto any one particular suture mount and thus onto the penile fascial tissues such as the Tunica Albuginea. Since the IC 24 and the MC 22 fit together and act as one functional unit, the suture slits 22N/24G align and the suture S passes through either the MC 22 or both the MC 22 and the IC 24 devices at the same time to mount, as needed. There are areas of non-overlap between the MC 22 and the IC 24. For example, the C-Shaped IC 24 will fit into the pocket space 22I of the MC 22, however, the IC 24 will not extend all the way around the penile shaft like the MC 22, so the ventral surface of the PSD 20 will only consist of the MC 22. The anchor locations are primarily located where there is overlap, as well as where there will be no overlap. The MC 22 extends slightly beyond the length of the IC 24 on its distal and proximal locations. The very distal end of the IC 24, and the distal end area of the MC 22, where there is overlap, form the suture anchor spaces. Suture anchors have several functions; they can be used to stabilize the IC 24 to the MC 22. Suture anchors can be used to anchor the MC 22 to the penile fascia. Suture anchors can be used to anchor the MC 22 and the IC 24 to the penile fascia. If the IC 24 and Main Component are mounted to the penile fascia, anchor suture slits will align so the suture can loop around both MC 22 and the IC 24 and attach to the penile fascia (see FIG. 2E, for example).

After the appropriate penile length measurements have been taken and the appropriate size PSD 20 selected, the PSD 20 will be placed onto the penile shaft. Once placed into position, an artificial erection will be induced, a distal lateral line slit 22Z will be opened to expose the suture slit, and a tissue marker will be used to place through the suture slits 22NI/24G of the PSD and make pen marks on the penile fascia. These marks on the penile fascia will assist the Surgeon as to where to place the sutures. Next, the distal lateral line slit 22Z will be closed, then the distal end of the PSD 20 will be inverted or folded to expose the pen marks on the distal end of the penile fascia tissue. Then the sutures S will be placed into Buck's Fascia and Tunica Albuginea fascia, then the suture threads S, will be placed through the PSD 20 suture slits 22N/24G of the both components of the PSD 20, the MC 22 and IC 24. Now, when the sutures S are "threaded" through the PSD 20 suture slits 22N/24G, and through the distal lateral line slit 22Z, then the distal folded end of the PSD 20 will be unfolded, the suture threads S pulled completely through. Then the distal lateral line slit 22Z will be opened, again, to expose the suture slits, and then the suture knots can be made to secure the PSD 20 into position, then the distal lateral line slit 22Z will be closed to which will cover the suture knots. As shown most clearly in FIG. 2E, it should be noted that there distal lateral line slit 22Z also comprises a tongue 22ZT and groove 22ZG type design to form a closure that also prevents fluid movement (e.g., L-lube) from exiting from the pocket space 22I of the MC 22. It should be noted that at each end of the distal lateral line slit 22Z is a tear reduction aperture 22H to minimize any possible tearing of the adjacent MC outer layer 22T1 during opening of the slit 22Z.

In cases where the PSD 20 is providing mild to moderate levels of ED functional support, the IC 24 may comprise a malleable metal material. This not only provides for additional firmness, but also allows for semi-permanent upward (erect position) and downward (flaccid position) bending, as needed, for the appropriate or optimal positioning during intercourse, and post intercourse. This follows the similar principle as the metal rod implants (which are placed in the cavernosal chambers directly), which are currently being used for moderate ED treatment. For example, when the patient wants to have intercourse, he simply bends his penis in an upward position, and the malleable metal will bend and stay in an 'erect' position, and then the patient can have intercourse. Then, when the patient wants to maintain a flaccid state, he bends and positions the penis downward. The PSD 20, in particular the IC 24, will have the similar properties, but the PSD 20, in comparison to the metal rod implants for ED, will have far ranging capability to also add penile girth, penile length, and other features as well.

PSD: Secondary Internal Component 24J

As shown in FIG. 10A a Secondary Internal Component (SIC) 24J for the PSD 20 may be needed in cases where there is a penile curvature that is extreme and additional structural support is warranted. The SIC 24J will be similar to the IC 24 in shape and material, but will be shorter in length to accommodate and provide the added support for the penile curvature area/zone only.

PSD: SIC and IC Plastic/Resin/Metal Component

The IC 24 and the SIC 24J may have the need to be made firmer or harder. There are numerous materials that can provide for the additional hardness including a very high hardness silicone type material. However, if other, even harder materials are needed for support, then plastic, resins, or even metal material will be considered. The addition of any or all of these materials can be done in several ways; for example, small round/square (etc.) flat pieces of metal can be inserted within the IC 24 silicone base material to add additional hardness. Any additional material, that is harder than the silicone used for the IC 24, can be "inserted" within the silicone element of the IC 24.

PSD-Collapsible 20B

An alternative to the PSD-smooth 20 and PSD-S-Fold (20A, 20A1 20A2) embodiments is the PSD-Collapsible 20B as shown in FIGS. 10C-10H. In this embodiment 20B, penile sleeve device only comprises a main component MC 22 so there is no internal component IC 24. In this embodiment 20B, the proximal end flange 22E' comprises a collapsible/expandable chamber 22EC in fluid communication with the pocket space 22I which is filled with either liquid or air. With the PSD-Collapsible 20B implanted within the penile shaft PS and the penis P is in a flaccid state (FIGS. 10C-10E), the majority of the liquid or air remains contained in the medial portion of the PSD-Collapsible 20B, as shown in FIG. 10E and the chamber 22EC is collapsed. However, when the penis P becomes erect, as shown in FIGS. 10F-10H, the expansion of the penis girth drives the liquid or air out of the medial portion of the PSD-Collapsible 20B and into the chamber 22EC, causing it to expand as shown in FIGS. 10F and 10G. Since the PSD-Collapsible 20B is a closed system, when the penis P returns to its flaccid state, the liquid or air returns to the medial portion of the PSD-Collapsible 20B.

PSD-Volume Shift 20C

Another PSD alternative is the PSD-Volume Shift 20C as shown in FIGS. 10I-10O. This embodiment is somewhat similar to the PSD-Collapsible 20B but instead of transferring liquid or air within the PSD itself, the liquid or air is transferred between an external reservoir R and the PSD. Like the PSD-Collapsible 20B, the PSD-Volume Shift 20C comprises no IC 24. In this embodiment 20C, the proximal end flange 22E" comprises an internal passageway that is coupled to, and in fluid communication with, a connecting tube CT which in turn is coupled to the external reservoir R that is implanted within the patient, e.g., between the bladder and pubic bone (FIG. 10I). The pocket space 22I is filled with either liquid or air such that when the penis is in the flaccid state (FIGS. 10J-10L), the majority of the liquid or air shaft PS and the penis P is in a flaccid state (FIGS. 10C-10E), the majority of the liquid or air remains contained in the medial portion of the PSD-Volume Shift 20C, as shown in FIG. 10L and the external reservoir is in a collapsed state, as shown in FIG. 10K. However, when the penis P becomes erect, as shown in FIGS. 10M-10O, the expansion of the penis girth drives the liquid or air out of the medial portion of the PSD-Volume Shift 20C and into the external reservoir R, causing it to expand as shown in FIGS. 10M and 10N. Since the PSD-Volume Shift 20C is also a closed system, when the penis P returns to its flaccid state, the liquid or air returns to the medial portion of the PSD-Volume Shift 20C.

PSD-Spoke 20D

Another PSD alternative is the PSD-Spoke 20D as shown in FIGS. 10P-10R. Like the PSD-Collapsible 20B and the PSD-Volume Shift 20C, the PSD-Spoke 20D comprises no IC 24. In the PSD-Spoke 20D, a plurality of radial spokes SPK are arranged between the MC inner layer 22S1 and the MC outer layer 22T1. Each of these spokes SPK can "collapse" of "flatten" when an outward radial force is applied; e.g., each spoke SPK may be pivotally mounted on one end to either the MC inner layer 22S1 or the MC outer layer 22T1. Thus, with the PSD-Spoke 20D implanted within the penis P, when the penis is in the flaccid state (FIG. 10Q), the radial spokes SPK are substantially radial in direction as shown in FIG. 10Q. However when the penis P becomes erect, as shown in FIG. 10R, the expansion of the penis girth drives inner layer 22S1 towards the outer layer 22T1, thereby causing the spokes SPK to "collapse" as shown in FIG. 10R. When the penis P returns to its flaccid state, the spokes SPK are biased to restore to their substantially radial position as shown in FIG. 10Q.

PSD-Insert 20E

Another PSD alternative is the PSD-Insert 20E as shown in FIGS. 10S-10V. Like the PSD-Collapsible 20B, the PSD-Volume Shift 20C and the PSD-Spoke 20D, the PSD-Insert 20E comprises no IC 24. In the PSD-Insert 20E, the MC comprises a plurality of distinct portions: a distal portion MC-DIST, an insert portion INS and a proximal portion MC-PROX. Each of these portions comprises corresponding coupling members, namely, the distal portion MC-DIST and proximal portion MC-PROX comprise respective collars COL that mate with receptacles REC in respective ends of the insert portion INS. To accommodate different sized penises, insert portions INS of different sizes can be coupled between the distal portion MC-DIST and the proximal portion MC-PROX.

PSD-Telescoping Design 20F

Figure 10Y:
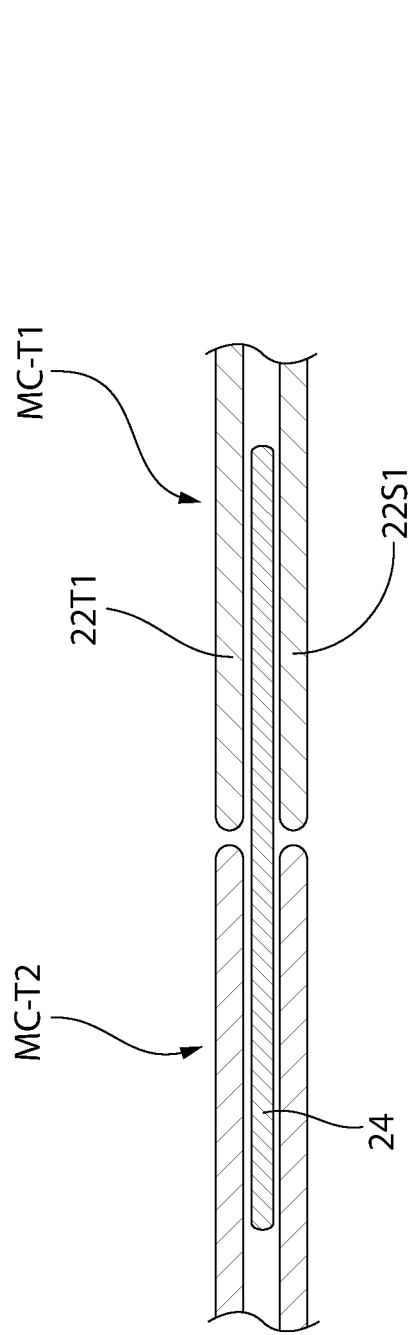
FIG. 10Y is a cross-sectional view of the PSD Telescope taken along line 10Y-10Y of FIG. 10W.
Figure 10Z:
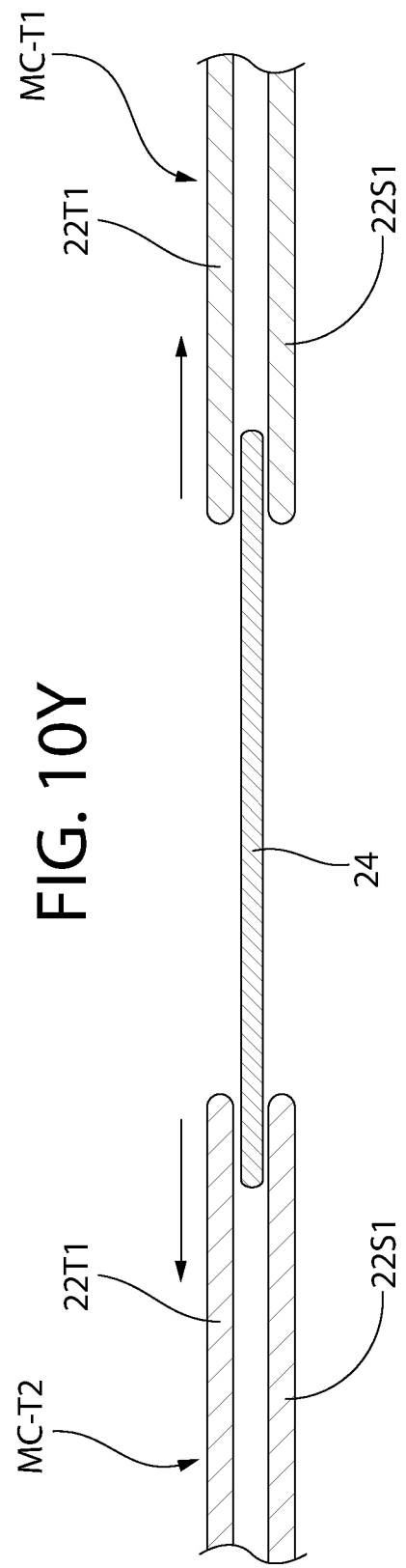
FIG. 10Z is a cross-sectional view of the PSD Insert taken along line 10Z-10Z of FIG. 10X.

In this PSD embodiment, the main component MC 22 comprises two distinct portions that slide over the IC 24. In particular, a distal telescoping portion MC-T1 and a proximal telescoping portion MC-T2 slide over the IC 24 (FIGS. 10W-10X), between inner layer 22S1 and outer layer 22T1 of each of the telescoping portions MC-T1 and MC-T2, as shown in FIGS. 10Y-10Z. Like the PSD-Insert 20E, the PSD-Telescoping Design 20F allows for the length of the PSD to be adjusted in accordance with the penis of the particular patient.

PSD-Fused

The PSD-Fused embodiment is similar to the PSD-smooth embodiment 20 but where the MC 22 and the IC 24 are fused together (e.g., melted) to form a unitary member. As such, there is no need for the dorsal mid-line slit 22J.

PSD-12 Inch

The PSD-12 Inch embodiment is similar to the PSD-S-fold embodiment 20A but only comprises the main component 22 as a single layer element. This device has a standard 12-inch length. When a patient is measured, the device will be cut down to size to fit the patient's penile length.

PSD: Suture Clips 80

As shown in FIG. 2E, Suture Clips 80 are small U-shaped pieces of plastic that will be used to protect the PSD 20 from the pressure of the sutures S. The Suture Clips 80 will be placed into the suture slits 22N/24G, like "straddling" the paired slits. Once placed, the suture knots will lie directly on the Suture Clips 80, not the PSD 20 silicone material. Without the Suture Clips 80 protecting the more fragile silicone rubber material, the suture S material would dig into and burrow through the silicone material over time and thereby destabilize the PSD 20.

PSD: Sutures S

The Sutures S used to mount the PSD 20 to the penile fascial tissues will be a non-dissolvable, very durable, strong type of Urological suture currently used in surgery.

PSD for Partial, Optimal, or Supra-Optimal Penile Flaccid Lengthening

If the patient has a flaccid length of 2-inches, and an erect length of 6-inches, he has the option to increase the flaccid length to 3, 4, or 5-inches, and this would be considered partial flaccid lengthening. If the patient desires a 6-inch flaccid length, which would match his current erect length, this would be considered an optimal flaccid length. Anything below 6-inches is considered a partial flaccid lengthening, and 6-inches will be considered optimal flaccid lengthening. If the patient wants to out-stretch the penis beyond the 6-inch range, let's say to 7 inches, this would be considered supra-optimal flaccid lengthening. There are PSD design differences to achieve partial and optimal flaccid lengthening.

The PSD 20 for partial flaccid lengthening comprises the MC 22 with the IC 24 for support, if needed. The PSD 20 results in lengthening of the flaccid penis by preventing the retraction or recoil forces of the penile tissues. These retraction forces originate from evacuated penile blood from the erect to flaccid state, muscle cell contraction, elastic and collagen fiber contraction, all of which are found within the penile structure. The PSD 20 flaccid length chosen for implantation will correspond to the patient's desired flaccid length gain. The PSD 20 is inserted and then anchored at the distal shaft, also called the sub-glans area (SGA). There is a tapering of the PSD 20 at the proximal and distal ends, so during the flaccid state or upon erection, the PSD 20 is near invisible and impalpable, not being able to feel any elevated ends of the device 20 through the penile skin. It should be noted that the general concept is to have both, the PSD 20 inserted in combination with having a filler treatment (FIG. 8A). The reason for the filler treatment is not only to provide girth to the penile shaft, but also to completely conceal the PSD 20, so that the PSD 20 may be imperceptible if carefully "looked for". Therefore, the filler treatment not only increases girth, increases the flaccid length to a modest degree, but it also provides a collagen layer within and just under the dermal spaces, 26, providing a natural skin tissue-like feel to "hide" the PSD (see FIG. 8A). The Proximal End Flange 22E of the MC 22 might be eliminated from the PSD 20 design if the flaccid length desired is below the flaccid optimal or supra-optimal lengths. If this is the case, the Proximal End Flange 22E might be modified or 'cut off' as needed. Note that to determine the segment of the penile shaft to which the PSD 20 will be placed and sutured to requires the penile shaft be artificially erected, then the penile shaft flaccid segment length that is desired will be marked off regarding suture zones, then PSD 20 will be placed onto that area. Once the PSD 20 is placed, the artificial erection is relieved, and the entire penile shaft, except the mounted segment by PSD 20, will contract and shrink. Also note that normal flaccid lengths need to be determined so an accurate final result can be achieved. For example, if the patient has a 3 inch flaccid length, and a 12 inch erect length, and desires to hang 9-inches flaccid, mounting the PSD 20 to 8 distal outstretched penile shaft inches will result in a final flaccid 9-inch length. This will be calculated by knowing that each 1 inch of flaccid length expands 4 inches (3 flaccid inches expanding to 12 inches erect), so if the distal 8-inches of the erect length are mounted with the PSD 20, that will leave only 1-inch of flaccid length left. So, the mounted 8-inch segment, once the erection has been removed, will remain 8-inches long, and the other 4 inch erect segment will shrink down to 1-inch; and this will total to a 9-inch flaccid length, just what the patient desired.

The PSD 20 for optimal and supra-optimal flaccid lengthening comprises the MC 22 and the IC 24 for support; in addition, the PSD 20 will need the Proximal End Flange 22E to "butt up" against the pubic bone and ligaments. The depth of the pubic pocket space 50 may exceed the length of the Proximal End Flange 22E, and in these cases a Proximal Extension (PE) will be needed to lengthen the Proximal End Flange 22E to fit within the pubic space to ultimately abut up against the pubic bone and ligaments. The PE length needed will vary depending on the amount of existing proximal anatomic "pocket" space by the pubic bony area PR. See FIG. 8E where the reference number 10 indicates a region that may be occupied with ligament and tissues which may limit the Proximal End Flange 22E length. The PE, which abuts up against the pubic bone area PR, is very important to stabilize the PSD 20 from proximal movement. The PSD 20 will need to be limited in extending or moving proximally, especially on the ventral side. Ventral proximal movement of PSD 20 will potentially impinge on sensitive ventral structures such as the penile urethra, corpora cavernosa, corpus spongiosum, etc., and this needs to be avoided. The space on the proximal dorsal penile shaft pubic area is occupied by the PSD 20, thereby preventing any further proximal motion of the PSD 20 and thereby protecting the ventral proximal edge of the PSD 20 from impinging on sensitive penile tissue structures. The PSD 20 is custom fitted to extend into that pubic pocket space. The proximal extension flange 22E of the PSD 20 is very important for optimal flaccid (and erect) lengthening stabilization, and for anatomic medical safety reasons, as discussed. Furthermore, the following terminology is important to PSD 20 operation:

Erect Length: Partial or Optimal erect lengthening

Flaccid Length: Partial, Optimal, Supra Optimal

Flaccid Penis: Out-stretched, Hyper-Stretched

Penile hardness/firmness—low, moderate or high

Functions: Length, Girth, Firmness (ED), Curvatures, Custom, flaccid length maximization Firmness—Low, Moderate, High Retraction forces: evacuated blood, muscle cell contraction, elastic and collagen fiber contraction, and over-stretched muscle-collagen-elastic fiber components.

Penile Curvature—Mild, Moderate

Penile Curvature Degree ranges; Non-Pathological 5 to 20, Pathological 5 to over 90

Careful measurements are taken to accurately and properly place the appropriately length PSD 20 for optimal or supra-optimal flaccid lengthening. To accomplish the patient PSD 20 "fitting", several measurements need to be taken including, but not limited to:

Flaccid "contracted" state girth

Flaccid fully out-stretched flaccid state girth

Flaccid hyper-stretched state girth and length (stretching beyond the normal erect length)

Erect: induced erect penile state length and girth

Erect: length and girth during a hyper-stretched erect state

Degloved: flaccid girth

Degloved: flaccid out-stretched girth

Degloved: flaccid hyper-stretched girth

Degloved: erect girth

Degloved: hyper-stretched erect girth and length

Degloved: obtaining measurement of depth of 'pubic pocket' (measuring to base of penile tissue to pubic bone).

Figure 6:
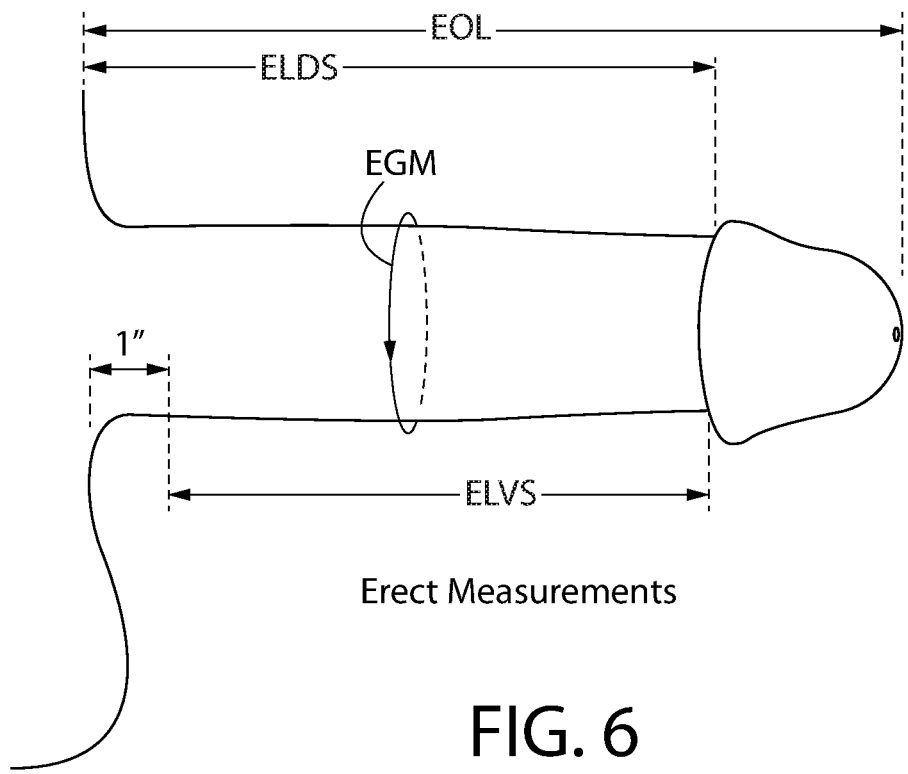
FIG. 6 depicts how penile measurements are taken for an erect penis.
Figure 6A:
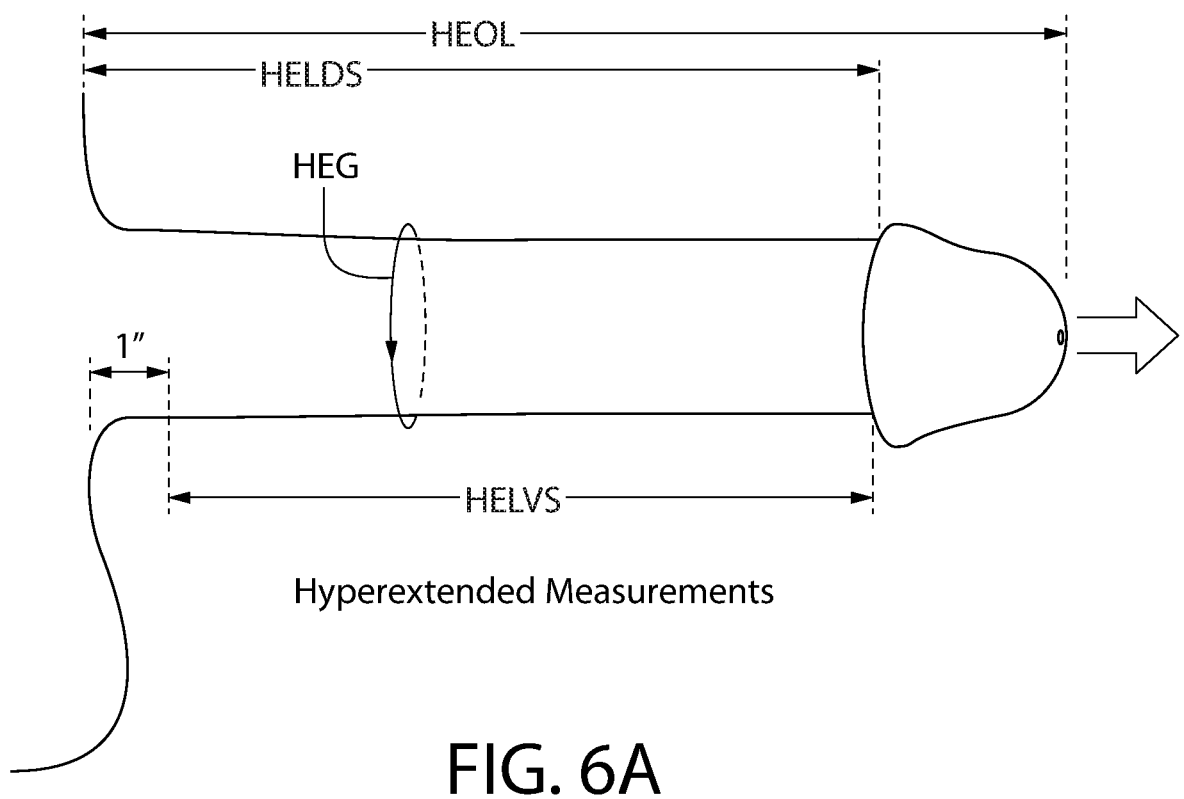
FIG. 6A depicts how penile measurements are taken for a hyperextended penis.
Figure 6B:
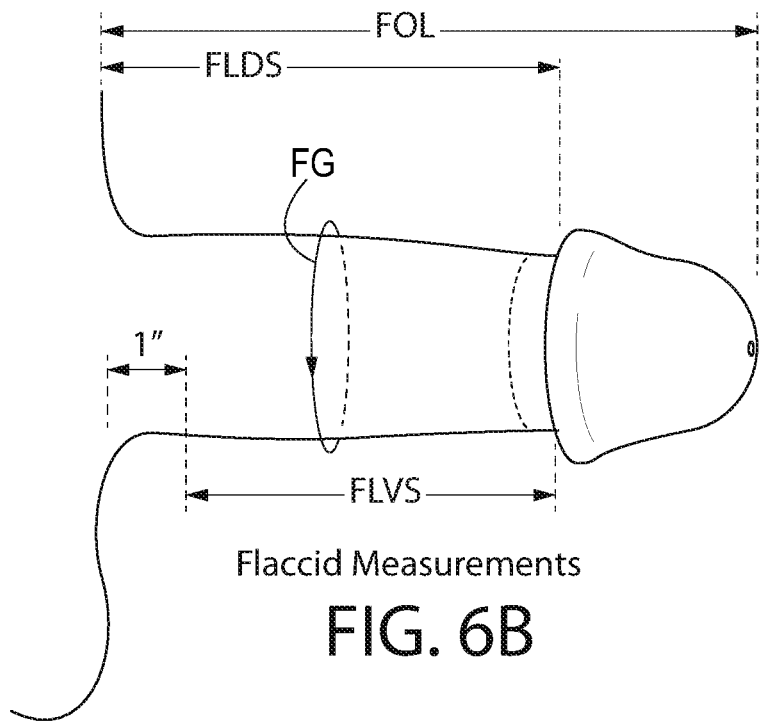
FIG. 6B depicts how penile measurements are taken for a flaccid penis.
Figure 6C:
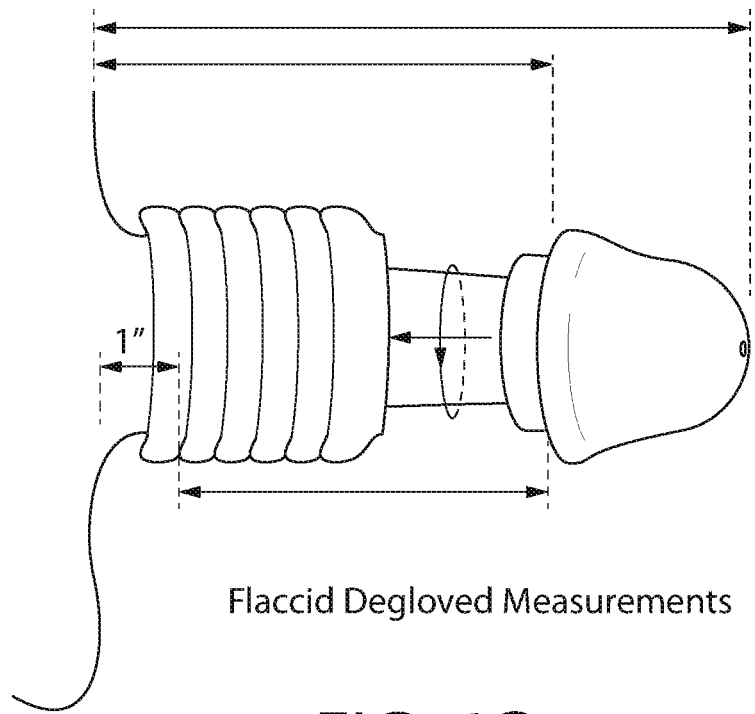
FIG. 6C depicts how penile measurements are taken for a flaccid degloved penis.
Figure 6D:
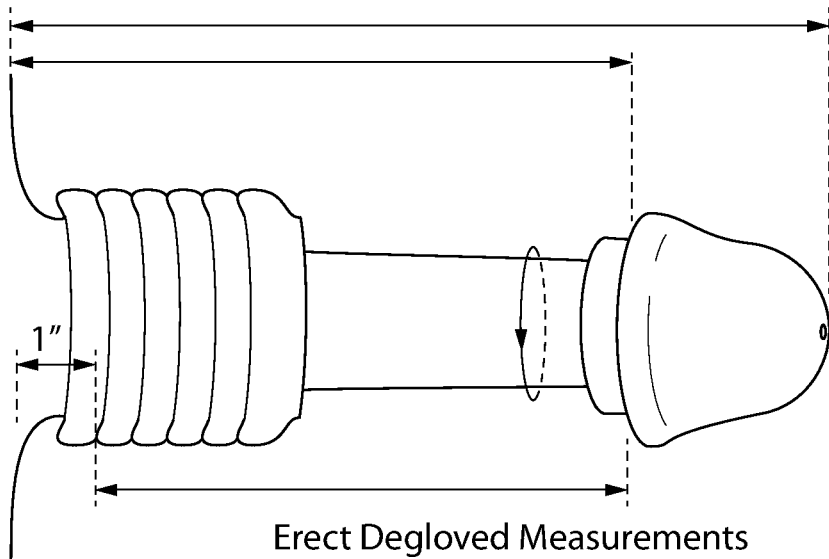
FIG. 6D depicts how penile measurements are taken for an erect degloved penis.
Figure 6E:
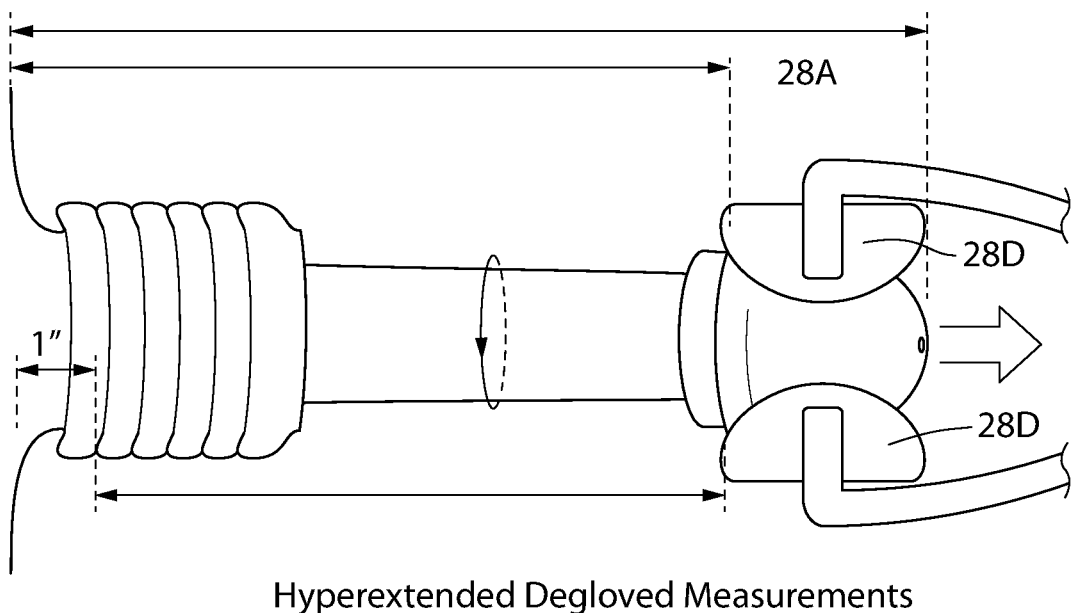
FIG. 6E depicts how penile measurements are taken for a hyperextended degloved penis.

FIGS. 6-6E provide functional diagrams for determining penis length and girth for different conditions of the penis enumerated above.

FIG. 6 sets forth the penile parameters for the erect penis. The erect girth is determined as shown by EGM. The proper way to obtain the erect penis length is to take measurements along the dorsal and ventral sides from the pubic bone to the glans-shaft junction, namely, ELDS and ELVS, respectively. With regard to the ventral side measurement ELVS, that measurement is taken 1 inch away from the peno-scrotal junction. In addition, the overall length EOL from the pubic bone to the meatus along the dorsal side is also obtained. It should be noted that the ventral erect measurement (normal erect and hyper-stretched lengths) is critical. All PSD 20 sizes are selected for patient implantation by this ventral length measurement. For example, if a patient has a dorsal erect measurement of 6 inches, but has a ventral erect measurement of 4.5 inches, then a PSD 20 with a ventral length of 4.5 inches will be selected. The PSD 20 sizes for manufacturing will go by ventral erect lengths. Now, that being said, if the flaccid penile shaft is stretched out to determine how much erect length can be achieved, the measurement will be taken from the ventral shaft glans junction and 1-inch away from the peno-scrotal junction. This is how a PSD will be selected in a patient who wants erect length increase. Again, the PSD 20 will "sit" just below the glans on the distal end, and cannot encroach upon the sensitive peno-scrotal tissues on the proximal end (and this is why a 1-inch 'buffer' is provided so the proximal ventral side of the device will not be in direct contact with these tissues).

FIG. 6A sets forth the penile parameters for the hyperextended flaccid penis. Before any measurements are taken, the flaccid penis is pulled by the glans to stretch out the penis which results in a length that is longer than the erect penile length. For example, if the penile erect length is 6-inches, the hyper-stretched flaccid penis may stretch out to 7-inches. The hyperextended girth is determined as shown by HEG. The proper way to obtain the hyperextended penis length is also to take measurements along the dorsal and ventral sides from the pubic bone to the glans-shaft junction, namely, HELDS and HELVS, respectively. With regard to the ventral side measurement HELVS, that measurement is also taken 1 inch away from the peno-scrotal junction. In addition, the overall length HEOL from the pubic bone to the meatus along the dorsal side is also obtained.

FIG. 6B sets forth the penile parameters for the flaccid penis. The flaccid girth is determined as shown by FG. The proper way to obtain flaccid penis length is to take measurements along the dorsal and ventral sides from the pubic bone to the glans-shaft junction, namely, FLDS and FLVS, respectively. With regard to the ventral side measurement FLVS, that measurement is taken 1 inch away from the peno-scrotal junction. In addition, the overall length FOL from the pubic bone to the meatus along the dorsal side is also obtained.

FIGS. 6C-6E are directed to measurements taken of the penis when it is in a degloved condition, meaning that the penile skin PSK has been pulled back exposing the penile fascia of the penile shaft PS. As such, the girth of the degloved penis can be determined. The flaccid girth state (FIG. 6C) has three measurements: normal flaccid, out-stretched, and hyper-stretched states. The flaccid girth state is measured is in its normal flaccid state (in its normal contracted state), its out-stretched state (pulling the glans until reaching erect length), and its hyper-stretched state (pulling the glans and reaching beyond the erect length). The flaccid length has two measurements: the flaccid length, (the out-stretched flaccid length is equivalent to it erect length, so this measurement is not needed), and the hyper-stretched flaccid length. The erect girth state has two measurements: erect (FIG. 6D) and hyper-stretched (FIG. 6E), using the same length parameters described above with regard to FIGS. 6-6B.

Erect measurements are taken by inducing the erection via injection. The penile shaft is injected with saline to create an artificial erection. Then, with certain measuring instruments, penile measurements are taken. The PSD 20 length is then modified if necessary. Then PSD 20 is inserted and anchored at the distal penile shaft area. The PSD 20 results in optimal or supra-optimal lengthening of the flaccid penis by preventing the retraction or recoil forces of the penile tissues.

PSD 20 for Partial or Optimal Penile Erect Lengthening

Penile erect lengthening can be either partial or optimal. Partial or optimal length is determined by how much "stretch factor" there is of the penile tissues. By way of example only, a patient has an erect length of 6 inches, but it can stretch, when physically pulled, to 8-inches. The patient may opt to increase the erect length to 7-inches, thereby requesting a "partial" erect length gain. If the patient opts to increase the penile erect length to 8-inches, this would be considered an "optimal" erect length gain.

There are minor PSD 20 design differences to achieve partial and optimal erect lengthening. The PSD 20 for partial erect lengthening comprises the MC 22 with the IC 24 for support. The PSD 20 has a key supportive role in keeping the penis in an elongated erect length, being abutted up against the pubic bone and ligaments and preventing the PSD 20 from proximal movement.

Careful intra-operative measurements are taken to accurately and properly select and tailor the PSD 20 for partial erect lengthening. To accomplish the size selection of the PSD 20, penile shaft flaccid and erect measurements are taken with and without saline injections. Then, with certain measuring instruments, an accurate natural erect length can be obtained. The erect penis is then relieved and resumes its flaccid state. Then, the flaccid penis is out-stretched beyond the erect length and measured to determine what additional erect length can be achieved. Once the PSD 20 length has been selected, placement can proceed.

In addition, considering that there could be additional retraction forces due to overstretching the penile tissues beyond the normal erect length, the PSD 20 may be designed with a higher durometer and/or with more thickness, and more anchor suture anchor locations in addition to the distal sub-glans anchoring suture anchor locations as needed. The PSD 20 causes partial lengthening of the erect penis by not only preventing the normal retraction or recoil forces of the penile tissues, caused by muscle cell contraction, elastic and collagen fiber retraction forces, etc., but also by exerting extra force to counter the now hyper-extended, now extra, recoil forces by these same elements. Additional recoil forces may be experienced when the erection process occurs, with blood flow into the penile shaft, on an outstretched penis. The blood enters into the corpora cavernosa CC and attempts to fill its chamber to not only capacity, but also may want to "shorten" to its original shape. It is analogous to trying to fill an outstretched round balloon with air: the balloon fills to its new stretched out form, but it "wants" to return to its normal round shape and so additional forces might be generated with an out-stretched penis onto the PSD 20.

The PSD 20 for optimal erect lengthening comprises the MC 22 and the IC 24. The PSD 20, with the appropriate MC 22 and IC 24 thickness and durometers, and proper location and quantity of suture locations, among other aspects, is very important for optimal erect lengthening and for anatomic medical safety reasons. The PSD 20 is measured accurately. The penile shaft is injected with saline to create an artificial erection, then, with certain measuring instruments, an accurate natural erect length can be obtained. The erect penis is then relieved and resumes its flaccid state. Then, the flaccid penis is out-stretched beyond the erect length optimally and is measured to determine what maximal additional length can be achieved. Once the PSD length has been selected, placement can proceed.

The PSD 20 causes optimal lengthening of the erect penis by not only preventing the normal retraction or recoil forces of the penile tissues, caused by muscle cell contraction, and elastic and collagen fiber retraction forces, but also by exerting an extra force to counter the now maximized hyper-extended extra recoil forces, as already mentioned prior. Additional recoil forces may be experienced when the erection process occurs, with blood flow into the penile shaft, on an outstretched penis. The blood enters the corpora cavernosa CC and attempts to fill its chamber to not only capacity, but potentially to its original shape.

Considering that the PSD 20 exerts a force on the penile tissues, this stretching force will, over time, stretch out the penile tissues, including the collagen, elastic, and muscle fibers, and result in a permanently stretched out penile shaft. Perhaps over a 6-12-month time period, the penile tissues will have stretched, now exerting little to no more recoil tension on the PSD 20. This new "stretched-out state" provides the patient with the option to "re-stretch" the penile shaft again to see if additional erect length can be obtained. This involves removing the original PSD 20 and placing in a new and longer PSD 20.

PSD and Penile Girth or Thickening

Most patients want a combination penile length and girth increase. The primary function of the PSD 20 is to increase penile flaccid and erect length, and the permanent filler is primarily for increasing penile flaccid and erect girth. Since the PSD 20 inherently provides some girth, due to its space-occupying physical characteristics, there are some simple design modifications that can be made to "optimize" this secondary girth function without causing cosmetic tissues. The PSD 20 can be made with varying thicknesses resulting in significant girth gains. However, the PSD 20, if designed to be made much thicker, may introduce increased risks of skin irritation, with the potential of additional complications, and may not be cosmetically pleasing to the touch, especially at its distal, proximal, and proximal ventral "edge" locations (if the PSD 20 is larger in general, the edges may not be easy to conceal from detection). These are the very issues other prior art penile implants on the market are having. Many patients with these implant devices are having them removed due to pain and having an unnatural feel. In contrast, the objective of the apparatus and method of the present invention, in combination of the permanent filler treatment process, is an overall enlargement process that is twofold: use (1) the PSD 20 for primarily lengthening, and (2) the permanent filler for primarily thickening. Considering that the PSD 20 is placed below the Dartos Fascia DF and above Buck's Fascia BF, it would be ideal to strengthen the tissues above the PSD 20 including this Dartos Fascia DF and penile skin PSK. This marriage between the two processes (PSD 20 and filler treatments) will not only address and keep the PSD 20 "bulkiness" to be minimal, resulting in less irritation and stress on the penile tissues, but also results in the permanent filler generating new collagen production, which will not only provide girth, but also thickens and "fortifies" the normal penile skin PSK dermal collagen layer and supra and intra Dartos Fascia (DF), thereby providing added protection from any type of irritation from the PSD 20. So, this additional "fortified", thickened, and protective newly-formed collagen layer within the penile skin PSK and Dartos Fascia DF, in conjunction with the PSD 20, will form a cooperative and synergic effect.

Most patients desire length and girth increases, but there are a few patients who desire only a girth increase, which is an option with the present invention. In other words, the patient wants to maintain his flaccid and erect length, but only increase the flaccid and/or erect girth. If this were the case, then the way to accomplish a flaccid and erect "girth-only" gain would be to place the MC 22 measuring the length of the flaccid penis. The MC 22 is anchored to the distal and proximal ends of the flaccid penile shaft. It should be noted that if the flaccid length is 2-inches, then the PSD 20 will be 2-inches. Then, upon erection, e.g., to a 6-inch erect length, the MC 22 will stretch and thin down resulting in a much thinner form, which will provide some girth in the erect state, but not optimal. The results regarding girth-only goals, especially erect girth, will be limited. These limited girth gains result from limited PSD 20 thickness, stretchability, and thickness size drop per penile inch stretched. The PSD 20 cannot be too thick because this increases the penile tissue stress from the PSD 20 stretching out from the flaccid to erect state, and those generated stresses are then transmitted to the anchor points and penile tissues, possibly resulting in lowering the PSD 20 longevity and causing patient discomfort. Considering this, the patient can be consulted to discuss appropriate recommendations to reach the patient's goals.

Increasing penile erect (and flaccid) girth can be broken down into low, moderate, or high levels. If one desires increased erect girth, with obligatory flaccid girth gains as well, then there could be an increase in the thickness of the MC 22 and, possibly, the IC 24, depending on the amount of permanent filler that is going to be considered.

The range of penile shaft girth thickness size that can be obtained with the PSD 20 ranges between 0.5-8 inches in circumference (not diameter). All girth measurements will be in circumference measurements, not diameter, and in inches, not in the metric system.

Here is an example, with measurements, of a PSD 20 providing a flaccid and erect girth gain. The average penile flaccid girth is 3.75 inches, and the average penile erect girth is 4.75 inches. This "differential" in girth size, from the flaccid to erect state, is 1-inch in circumference. If a patient desires to add a low girth increase, for example, a 1-inch erect girth gain, from 4.75 inches to 5.75 inches, the PSD 20 is modified to be approximately 4/16ths of an inch thick in the flaccid state, which will result in a thickness of 3/16th of an inch thick once stretched out in the erect state. So, once an erection takes place, the penis expands and lengthens causing some "thinning down" of the PSD 20. This size drop, or thinning down of the PSD 20, occurs and plays a role in determining what size flaccid PSD 20 is required to determine the erect PSD 20 girth size. This size thickness PSD 20 yields about a 1-inch erect girth increase, or a 5.75-inch erect girth penile shaft size.

Calculating the circumferential girth gains is in accordance with the circumference equation, $\pi D$, i.e., multiplying the diameter of the PSD 20 by $\pi$ or roughly by 3. So, for example, if there is a PSD 20 of 3/16th-inch (erect state) thickness, then the diameter increase is 6/16th of an inch (3/16th thickness on one side of the penile shaft, and 3/16th of an inch on the other side of the penile shaft=6/16th of an inch total), and the circumferential increase is 6/16th inch diameter×3=18/16th inch, or just about and slightly over a full inch gain in circumference.

During the flaccid state, the PSD 20 is larger, for example, 4/16th of an inch thickness, because it is not out-stretched and thinned down during the expansion of the erect state. The flaccid girth, with a 4/16th size PSD 20, yields about a 1.5-inch increase in the flaccid girth. So, the flaccid girth is 3.75 inches plus 1.5 inches, or a flaccid girth of 5.25 inches. The erect girth, with a 3/16th of an inch size thickness outstretched PSD 20, results in about a 1-inch circumferential gain, yielding an erect girth of 5.75 inches. As the PSD 20 increases to very large thicknesses, the flaccid girth size will begin to approach the erect girth size, so eventually the erect state, with the consistent and same amount volume of blood flow during the erection process, will barely increase the erect girth. For example, in the normal flaccid penis of 3.75 girth, and an erect girth of 4.75 girth, if one adds 4 inches of flaccid girth, now being 7.75 inches (or 7 12/16ths), the amount of blood entering into the penis is the same. So, the erect girth increase might be 1/16th of in an inch, with a resultant 7 13/16th total erect girth.

The primary component of the PSD 20 that provides for most of the girth is the MC 22. The IC 24 can provide significant girth, but since this is the "hard" portion of the PSD 20, increases in the thickness of the IC 24 are reserved for ED, additional erect firmness, and curvature correction needs. If a patient wants to increase his erect girth from 4.5 to 8.5 inches, then if the MC 22 is too thick, it may result in a "soft" feel during the erect state and this is not desirable. In such cases, the IC 24 will be made thicker to provide some of the girth and ensure firmness or hardness is maintained. The MC 22 requires substantial thickness not just for providing girth, but also to provide comfort since living tissue does not like long term pressure placed on it by hard substances. So, a delicate balance will need to be considered when very large size PSDs 20 are being used.

PSD and Penile Hardness or Firmness

Penile hardness, or firmness, can be broken down into low, moderate, or high. If one desires to add this feature, then there is an increase in the durometer (and possibly thickness) of the IC 24 and possibly the MC 22 as well.

Patients with mild or even moderate levels of erectile dysfunction (ED) issues can benefit from a more firm or harder PSD 20. Currently there are medical and surgical treatments for ED. When medical treatments fail to provide added firmness, such as VIAGRA®, or similar oral medications, or injectable and suppository meds, etc., then there are surgical options such as having an implant placed deep within the penis. There are two types of implant devices, the metal rod type, and the balloon pump type. Both of these devices are placed directly into the corpora cavernosa (CC) or the deep tissues of the penile shaft. This surgical procedure is under general anesthesia because there is deep cutting into the penile tissues needed to place the device. This deep cutting will result in significant penile tissue damage specifically to the fine sinusoidal architecture SA of the cavernosa. After placement of these devices, and permanent irreversible damage done, there is no turning back; patients must now rely on this system for the erection process for the rest of their lives. In addition, the balloon implants can malfunction, break, etc., which would then need to be replaced, thereby resulting in another operation with the same risks of infection, anesthesia, etc. Over all, and even considering the risks involved, these metal rod and balloon systems provide very good treatment options for those with moderate ED.

As an alternative treatment for low to moderate levels of ED, the PSD 20 has an optional design feature that can provide greater firmness and thus help with ED support. This PSD 20 can provide a lower risk option for patients with mild to moderate forms of ED. The benefits of using the PSD 20 for ED include; not causing permanent damage to the corpora cavernosal CC tissues; and no need for general anesthesia, and associated risks associated with it, in most cases; and, lastly, the PSD 20 is placed only skin deep, in the subcutaneous space, and easy to remove if needed, without the need to cut deep into the penile tissues.

PSD and Penile Curvature Correction

If the penile shaft is not straight during an erection, the penile shaft has a curvature. Penile curvatures can be classified as mild or moderate. Curvatures can occur naturally or pathologically (caused by a disease or traumatic process, for example). Curvatures can also occur in a variety of locations on the penile shaft, and directions. Curvature directions include a dorsal (upward) curve, a ventral (downward) curve, a right or a left curve, twisted or spiral type curve, or any combination thereof. Curvatures can also be located at particular segments of the penile shaft, such as at the penile base (proximal area), or at the shaft mid-section, or distal shaft area, or a combination thereof. Natural curvatures are generally mild, not in multiple locations, and curve from 5 to 20 degrees. Pathological curvatures can range from a 5 to over 90 degree curvature and be found in more than one location on the penile shaft.

If one desires to correct the curvature, the PSD 20, with certain design changes, can help. To assist in curvature correction, an increase in the durometer (and possibly thickness) of the IC 24 is made and possibly in the MC 22 as well. In addition, a SIC 24J (FIG. 10A) can assist to counter this curvature force. The SIC 24J does not necessarily have to be the same length, durometer, or thickness as the IC 24, but can be custom tailored for the need presented. For example, if the penile curve originates at the mid-section of the penile shaft, then the SIC 24J, if needed, is placed at the mid-section of the penile shaft which would provide additional "straightening" support at that specific location. If the SIC 24J is added, it will be, in general, much shorter in length than the IC 24. The objective of the SIC 24J is for "target" treatment, so its length will be appropriate for the need. This extra support provided by the SIC 24J, whether a partial or full-length support (if needed), helps counter the curvature force directly where it occurs. The SIC 24J can be placed on top of the IC 24 and mounted, with sutures if necessary, to assist in stabilizing this PSD 20, preventing the SIC 24J from sliding out of position. The mounting technique for the SIC 24J to the IC 24 and MC 22 may vary. One option is to simply place the SIC 24J on top of the IC 24, both using the same pocket space 22I within the MC 22 for stabilization. Another technique can be suturing the SIC 24J to IC 24, or suturing the IC 24 and SIC 24J to the MC 22 as well, etc.

PSD and Penile Custom Shape

Custom penile shapes can vary and be numerous. For example, a patient may desire a "veiny" look, which would require adding "veins" 22F to the superficial aspects of the MC 22 mold. Some patients may want specific asymmetries, such as an increased proximal to distal shaft thickness, or even a mid-shaft thickening. Other custom shapes, such as having "bump outs" 22G like implantable "pearl like" effects, can also be possible.

Another special case is with patients who are not circumcised. Regarding PSD 20 placement, the circumcision status is not relevant, however, if permanent filler is going to be used at a future date to increase penile shaft girth, then it is recommended to get a circumcision prior or after PSD 20 placement, and before permanent filler placement. The patient, however, still may opt not to get a circumcision. In this situation, the patient can have the PSD 20 placed, but if the patient wants permanent filler treatment afterwards, the resultant collagen production may only provide little to no girth increase in the distal shaft area, where the foreskin is, in some cases. The area that the foreskin resides on the penile shaft, once erected, occupies approximately one to two fifths of the distal penile shaft. Considering this, the patient may opt to modify the PSD 20 to have improved and more symmetrical balance, if needed, by increasing the distal girth of the PSD 20. This increase will help balance out this potential filler deficit, or area that not much filler can be placed, at the distal one to two fifths penile shaft area. Another remedy would be to add a SIC 24J just at the distal one to two fifths of the PSD 20 to compensate for the disproportion and asymmetric narrowed area due to the little to no girth gain in that area.

PSD: Penile Flaccid Elongation with Girth

The PSD 20 is designed to be a stand-alone device, providing flaccid length and girth, but primarily length with girth to a certain extent. For example, if the PSD 20 is too large (thick), providing the entire desired girth size, which size can be substantial, it may become uncomfortable, palpable to the touch, and increase the risk of skin irritation. Therefore, it is recommended that a filler technique be used (to meet the girth goals) in conjunction with the PSD 20, which would meet the primary length goals. The filler, which results in collagen production, such as that disclosed in U.S. Pat. No. 9,993,578 (Loria), whose entire disclosure is incorporated by reference herein, not only provides the additional girth needed but also provides a natural cosmetic feel and structural support for the penile shaft skin. This structural support is formed by; additional collagen formation within the existing natural dermis collagen, in the immediate penile skin subcutaneous area, and the physical attachment of this subcutaneous collagen to the undersurface of the penile skin or dermis. This "'physically attached" collagen would now be in direct contact with the PSD 20, not the natural penile dermis. This structural support, with all this new collagen in and under the penile skin, will help prevent potential minor skin irritation, inflammation, etc., by direct contact of the PSD 20 on this area. If the patient prefers not to have any permanent filler placement but only place the PSD 20, and finds that the PSD 20, once inserted, feels natural and comfortable, then no further filler treatments will be needed.

The PSD 20, used for flaccid elongation, will typically encounter mild to moderate retraction or recoil forces by the flaccid penile shaft. For example, a patient who wants to optimize his flaccid length, with only an obligatory girth gain from the PSD 20, has measurements of: flaccid length of 4-inches, erect length of 5-inches, and an erect girth of 4.75 inches. In this case, the patient desires to have a flaccid length of 5 inches with an erect girth of 4.75, or as close to that as possible. There is an obligatory minimal thickness of the PSD 20 (a thin MC 22 and, if needed, a thin IC 24) providing a mild counter force needed, to accomplish the full 5-inch goal since the retraction force is minimal (only stretching from a 4 inch to a 5-inch length). The erect and flaccid girth increases some, because even though the PSD 20 is as thin as possible, there still is an obligatory ½ to ¾ inch gain in girth.

Another example is a patient who wants to optimize his flaccid length (or have supra optimal flaccid lengthening) with a minimal girth gain has measurements of; flaccid length of 1-inch, erect length of 8-inches, and an erect girth of 5 inches. Considering there is a lot of retraction forces to counter, the PSD MC 22 will be thicker, and the IC 24 is going to be, most likely in this case, thicker to help counter this moderate to high flaccid penile retraction force. Additional anchors may be used. The length goal is achieved; however, the patient may gain an obligatory 1 to 1.25 inches in girth simply due to the inherent nature of the device having increased girth itself due to the increased thickness of the PSD 20 which is needed to withstand the retraction forces. If any of the aforementioned patients wanted any additional girth, reaching the moderate to high sizes, the MC 22 thickness would increase and/or more filler would be placed. Additional suture anchors are placed as needed. Note that supra optimal flaccid lengthening would increase the flaccid length to 9 or more inches and would also increase the penile erect length which would now require additional structural and retraction force support.

PSD: Penile Erect Elongation with Girth

The PSD 20 withstands a greater force when erect elongation is desired, as opposed to the relatively minor retraction forces encountered with partial or optimal flaccid elongation. Considering this, an overall thicker and harder PSD 20 is required. The MC 22 is thicker with a higher durometer, if needed, and this will provide the additional structural support in addition to the inwardly-directed radial force or "gripping force" needed on the penile fascia to maintain the partial or optimal erect length increase. The IC 24 provides additional support to PSD 20 in withstanding the retraction forces, and prevents the MC 22 from folding on itself, buckling, etc. This IC 24 also provides for firmness to the touch, considering its much higher durometer, and added girth, if needed, on a case by case basis.

Some examples to demonstrate the concept of penile erect elongation are as follows: A patient wants a partial erect lengthening with girth enhancement. His measurements are: flaccid length 3 inches, erect length 6 inches, erect girth 5 inches, and an optimal out-stretched penile length of 8-inches. In this case, the patient wants to be 7-inches in erect length (a partial erect lengthening), and 6.5 inches in girth. Considering these desired patient parameters, there will need to be a moderate thickness and moderate durometer hardness of PSD 20 because the PSD 20 will encounter moderate to high retraction forces and will need to provide the desired girth increase as well.

Another example involves a patient who wants optimal erect length and increase erect girth to 6.5 inches. His measurements are: flaccid length of 4-inches, erect length of 5-inches, erect girth of 4.5 inches, and an out-stretched flaccid penile length of 6.5 inches. In this case, there will need to be a PSD 20 with high thickness to meet the girth goal, and a high durometer to counter the moderate to high retraction forces to accomplish the optimal 6.5-inch erect length and a 6.5-inch girth goal.

Another example involves a patient who wants optimal erect length with a 7.5-inch girth. His measurements are: flaccid length of 1-inch, an erect length of 8-inches, erect girth 5 inches, and an out-stretched flaccid length of 9.5 inches. Considering that there is an excessive retraction force to counter, the PSD 20 will need to be thicker (providing girth and structural support as well) and have a higher durometer to help counter this high penile retraction force and provide the girth gains desired. The MC 22 will be thicker, to accommodate for the girth increase, and an increase in durometer will also be needed; and the IC 24 will have a high to very high durometer with the appropriate variations in thickness. Additional suture anchors are placed as needed.

PSD: Materials

PSD 20:

Main Component 22: Medical Grade Implantable Silicone Elastomer

Internal Component 24: Secondary Internal Component 24J, Proximal Extension flange 24D: Medical Grade Implantable Silicone Elastomer with the possible addition of other bio-materials such as malleable metal alloys are used, such as aluminum, lead, gold, silver, platinum, copper, etc. or combination thereof. Plastic materials may be used as well.

Plastic Suture Clips: Medical Grade Implantable Plastic Component or similar bio-implantable material.

Sutures: Non-Absorbable type.

Delivery Devices

Glans Gripper Device 28: Silicone rubber, metal, and plastic.

T-Device 30: Silicone rubber, metal, and plastic.

Bio-Degradable Lubricant: Medical Grade Sterile Carboxymethyl Cellulose or other types.

Silicone Oil Lubricant: Medical Grade Sterile Silicone oil.

It should be noted that the malleable metal alloy that may be used in the PSD 20, specifically the IC 24 to achieve greater hardness and structural support, and in the MC 22, and/or the proximal extension flange 22E, to achieve a certain firmness or hardness, in addition to assist in proper penile angulation for the ED patient during the erect state, which would be angled upwards, and the flaccid state, which would be angled downwards.

PSD: Durometer

The MC 22 has a very low to moderate durometer, low to high thickness, and very stretchable. These characteristics allow for patient/tissue comfort, expandability during an erection, during penile stretching or bending, low stress on pressure points (distal glans rim area for example) and protects against the potential irritation caused by the hardness of the Internal Component.

The IC 24 has a moderate to very high durometer, low to high in thickness, and has mild to moderate flexibility. The IC 24 provides support and hardness to the PSD 20 as a whole. These characteristics allow for a normal firm/hard feel in the erect state, provide support to the MC 22 preventing folding, buckling, etc., and provide the counter force to the penile retraction.

PSD: Thickness

The thickness of the PSD 20 varies for certain circumstances. For example, the primary concern is to have the MC 22 and the IC 24 thick enough to achieve the lengthening goals and provide girth as a secondary goal. When additional girth is desired, then some thickening of these components provides some, and potentially all, of the desired girth gain. It is difficult to determine if the PSD 20 can provide all of the girth a patient may want without the PSD 20 becoming too large, resulting in feeling unnatural and/or uncomfortable. To address this concern, use of a permanent filler treatment may need to be provided to balance out these issues. The concept is to use the PSD 20 as a primary lengthening device, with some girth as a secondary aspect, and then supplement with permanent filler to reach the desired full girth goal, such that, the final results regarding length, girth, and feel meet the patient's expectations.

The thickness of the MC 22 is, in most cases, greater than the IC 24. The IC 24 may be thicker than the MC 22 in certain circumstances such as in a PSD 20 for ED, or simply a patient's desire to be very firm in the flaccid and erect states.

The thickness of the MC 22 and the IC 24 varies from proximal to distal end due to the need to narrow down, or taper. Other areas of the tubular sections 22/24 are tapered as well, especially in the areas where the IC 24 fits into the pocket 22I of the MC 22.

Excessive thickness, which may increase the inwardly-directed radial force, is avoided because the pressure differential must be maintained for erection purposes. If the thickness (or hardness) of these device components are too high, then the pressure needed to get an erection might not overcome this external inwardly-directed radial force and thus result in a limited erection or blood volume flow into the corpora cavernosal CC tissue.

Different thickness ranges and certain aspects considered:

Main Component 22: 2 to 20 mm thick.

Internal Component 24: 0.5 to 10 mm thick. These ranges provide for all scenarios of erect lengthening, girth, and hardness goals.

Penile retraction forces and desired penile length govern the thickness and durometer of the MC 22 and the IC 24 components. Higher durometer and thickness sizes are used with higher retraction forces and longer penile lengths.

The flaccid thickness of the PSD 20 is thinned down upon erection, due to the PSD 20 being out-stretched in a circumferential manner. This thinning down effect is calculated appropriately to provide an accurate erect girth size.

The normal or average diameter of an erect penis shaft is approximately 1.5 inches or 3.8 cm. The average circumference is 4.75 inches or 12 cm. If a 4 mm (diameter) thick device is placed, it increases the flaccid girth by 1-inch or approximately 2.5 cm. However, when erect, the PSD 20 thins down, possibly by 50% (depending on the amount of normal blood flow into the penile shaft during the erection process), so the erect girth decreases to about ½ inch or 1.25 cm.

If the MC 22 is too thick, and the IC 24 is too thin, it may compromise the final erect firmness. The exact sizes for the MC 22 and the IC 24 are determined intra-operatively by creating artificial erections, via saline injection, and external palpation of the PSD 20. The remedy for increasing erect hardness is simply by increasing the IC 24 thickness and/or durometer, decreasing the MC 22 thickness, or increasing the MC 22 durometer.

The MC 22, in most cases, is the thicker component. It is also flexible, and stretchable. These aspects are key for the penis to become erect without a significant opposing inwardly-directed radial force, and to have a soft device in contact with the penile tissues for comfort and to eliminate irritation and chronic pressure.

PSD: Shape

Edges

Any portion of the MC 22 and IC 24 directly or indirectly in contact with the penile tissues have smooth and rounded edges. In addition, tapered/rounded zones or areas, such as 22P, 22ET, 22DT, 22OT (FIG. 1), etc., are provided for smooth transitions. Tapering is provided but not smaller than a tapered edge thickness of 1-4 mm. Structural integrity of the material and device as a whole, even in the thinner areas such as the tapered areas, is maintained so as not to invite unwanted fragmentation, tearing, etc. at these thinner tapered edges.

PSD: Texture

The general surface of the PSD 20 is smooth in most locations. The buckle zone, for example, may have an undulating pattern, however, the surface of this pattern is smooth and rounded.

PSD: Dorsal Surface

The dorsal surface of the MC 22 has a dorsal mid-line slit opening, spanning a certain length from the proximal to distal end of the MC 22. This slit opening is used to allow the insertion of the IC 24.

Provide cosmetic anatomic venous structure or 'bumpy' options for the dorsal and dorsal/lateral surface of the MC 22.

The buckle zone 22L can be seen on the dorsal surface having a wavy undulating pattern.

The proximal end flange pocket 22Q, that will receive the IC 24 proximal end flange 24D, has its own particular surface architecture. It is designed with elevations and depressions to receive the proximal end flange 24D, if needed, as a tongue and groove or elevation and depression type pattern to assist the proximal end flange 24D and end flange pocket 22Q to lock in place together.

PSD: Ventral Surface

The MC 22 also comprises a molded U-shaped portion 22R (FIGS. 9B-9C) along the entire ventral longitudinal length to limit pressure and accommodate the urethra for urinary and ejaculatory flow. This U-shaped portion 22R allows urinary flow in the flaccid and erect states, and allows ejaculatory flow in the erect state, due to little to no direct pressure placed on the urethra by the PSD 20. The final erect state pulls on the U-shaped portion and flattens it some (see FIG. 9C), so the flaccid design provides for the erect state distorting or stretching this U-shaped area. This means the flaccid shape forms more like a very narrow U-shape at first. Then, upon erection, it widens into a true U-shape.

Provide cosmetic anatomic venous structure options for the MC 22.

The buckle zone 22L can be seen on the ventral surface having a wavy undulating pattern.

PSD: Lateral Surface

Figure 1A:
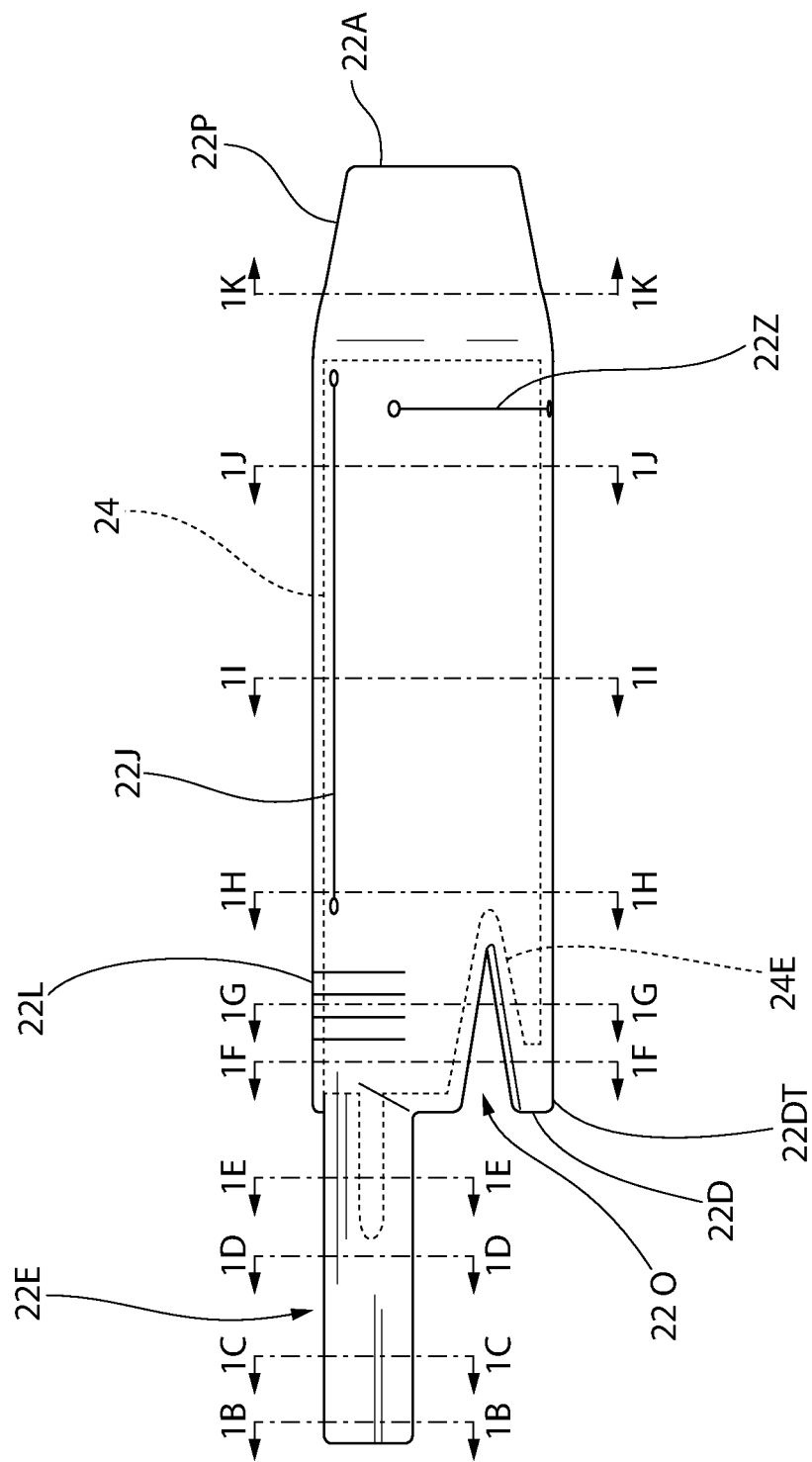
FIG. 1A is a side view of the PSD of FIG. 1.
Figure 1E:
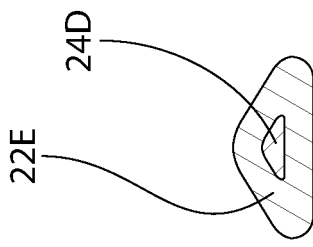
FIG. 1E is a cross-sectional view of the PSD taken along line 1E-1E of FIG. 1A.
Figure 1D:
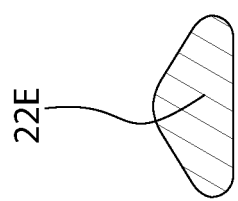
FIG. 1D is a cross-sectional view of the PSD taken along line 1D-1D of FIG. 1A.
Figure 1C:
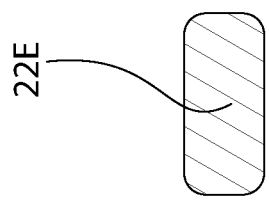
FIG. 1C is a cross-sectional view of the PSD taken along line 1C-1C of FIG. 1A.
Figure 1B:
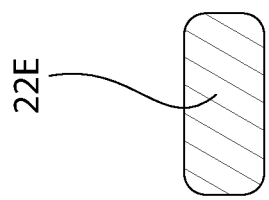
FIG. 1B is a cross-sectional view of the PSD taken along line 1B-1B of FIG. 1A.
Figure 1K:
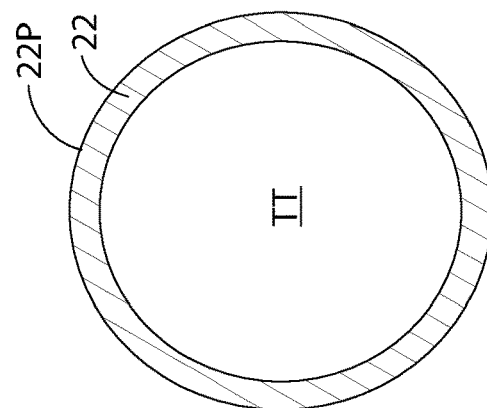
FIG. 1K is a cross-sectional view of the PSD taken along line 1K-1K of FIG. 1A.

A proximal lateral V-cut 22O (in MC 22) and 24E (in IC 24), are placed at the proximal lateral ends as shown most clearly in FIGS. 1A and 2G. This V-cut design allows downward movement of the PSD 20 during downward bending of the penis during squatting motions. This downward bending motion is necessary, and if this did not occur, then the PSD 20 would project proximally and push up against the urethra, spermatic cord, and/or other scrotal tissues, etc.

Provide anatomic venous and 'bumpy' structure options 22F/22G for the MC 22.

The buckle zone 22L can be seen on the ventral surface having a wavy undulating pattern.

PSD: Distal Area

Rounded edges at the distal end of the MC 22 of PSD 20.

Distal tapering of the MC 22 for a natural transition to the sub-glans area.

The Distal Lateral Slit Line 22Z is present to gain access to the suture anchor slits, 22N, for suturing purposes.

Suture anchor slits 22N, to mount (if needed). Additional suture anchor points can be placed along the MC 22 anywhere along the penile shaft, with corresponding or additional "lateral slit lines", as needed, for access.

The pocket space 22I extends within the MC 22 to accommodate and fit the entire IC 24, including in this distal area.

PSD: Proximal Area

Rounded edges at the proximal end 22E, of the MC 22.

The Proximal End Flange 22E has no to minimal tapered edges, but has rounded edges.

The pocket space 22I extends within the MC 22 to accommodate and fit the entire IC 24, including in this proximal area.

The proximal end of the MC 22 and IC 24 may be elongated to form the Proximal End Flange, 22E and 24D, respectively. The reason for the elongated proximal end is to slide into the pubic fascial plane 40 (FIG. 8E) and "fill" the pubic pocket space near the pubic bone PB/ligament area for the PSD 20 to advance. This lengthening will now fill that pubic pocket space and prevent potential proximal movement for stability, balance, and safety.

The MC 22 proximal end will be rounded, or even bulbous, and non-tapered. This type of bulbous and non-tapered end would be more advantageous due to the location of this proximal end, deep under the pubic pocket area where it cannot be "touched" or "felt." Also, if the proximal end is wider, it will be able to withstand higher forces and be able to distribute those forces over a greater surface area. If the proximal end was tapered, then it would exert a higher force per unit area on the bone/ligamentous tissues, and possibly results in pain and inflammation. If the proximal end is rounded, or bulbous, but kept non-tapered, the force distribution over a larger surface area will be greater which will decrease the force per unit area providing less tissue stress and greater comfort. It will be desirable for the PSD 20 to fit snugly in the pubic space or, "fit like a glove". The PSD 20 is to slide in as far as possible on the dorsal area and close to or on the pubic suspensory ligaments. On its ventral side, the PSD 20 is to be close to, but not on, the scrotal area or penile structures such as the urethra. This proximal end abutment into the pubic space and against the pubic bone and ligament, helps lock-in the PSD 20 and prevents proximal movement or sliding of the PSD 20, thereby maintaining stability of PSD 20 as a whole. If PSD 20 were not positioned optimally being abutted up against the pubic bone and ligaments, and was able to slide proximally into deeper areas of the pubic space, this may result in excessive force on the distal suture area if the device is 'pushed' in a proximal direction.

The MC 22 proximal end flange 22E is designed to be cut to reduce its length, if necessary, to fit into the pubic bone/suspensory ligaments space.

Figures 4, 4A:
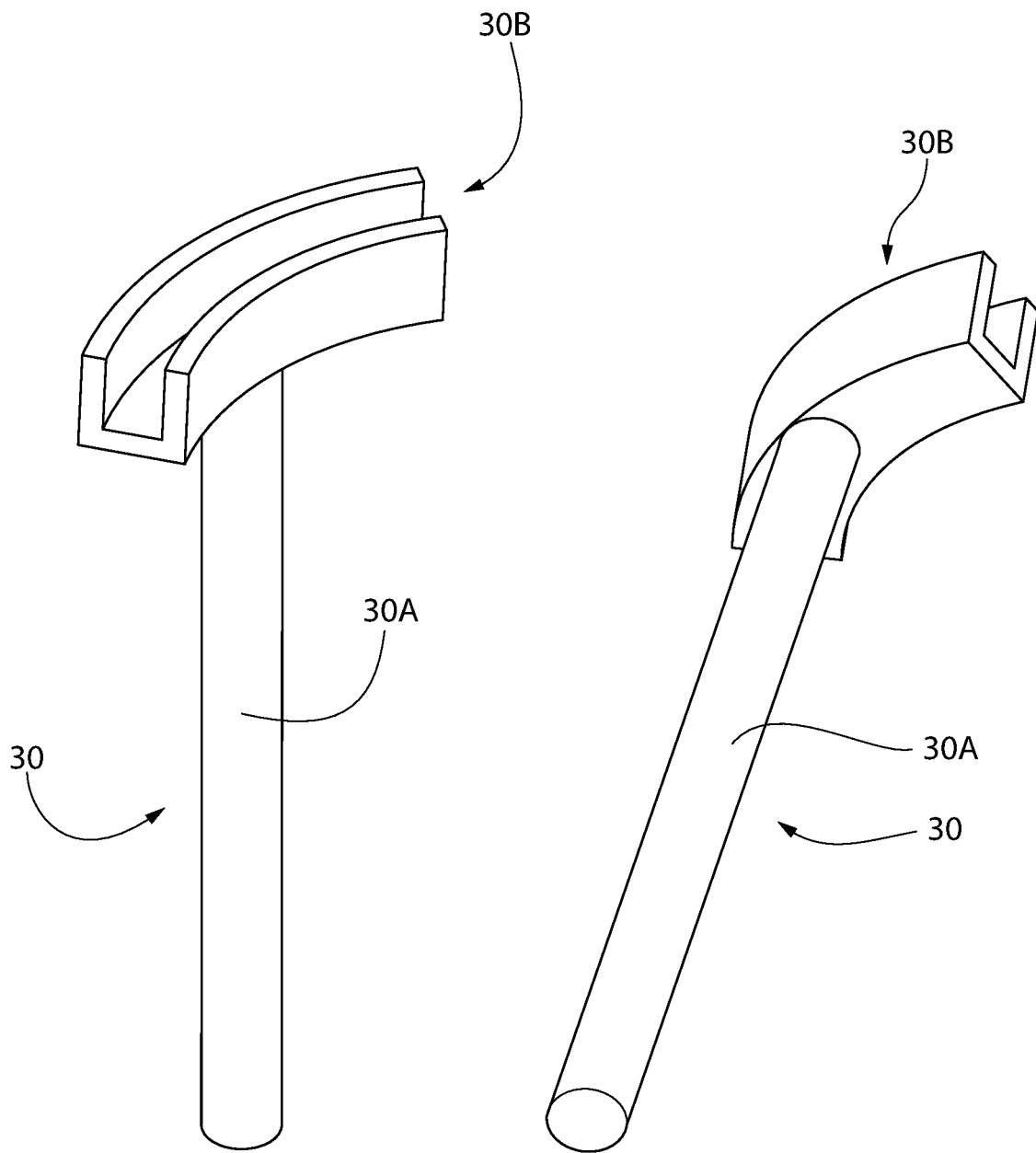
FIG. 4 is an isometric view of a transfer device (referred to as "T-Device") for displacing the PSD along the penile shaft during implantation.
FIG. 4A is another isometric view of the T-Device of FIG. 4.
Figure 4B:
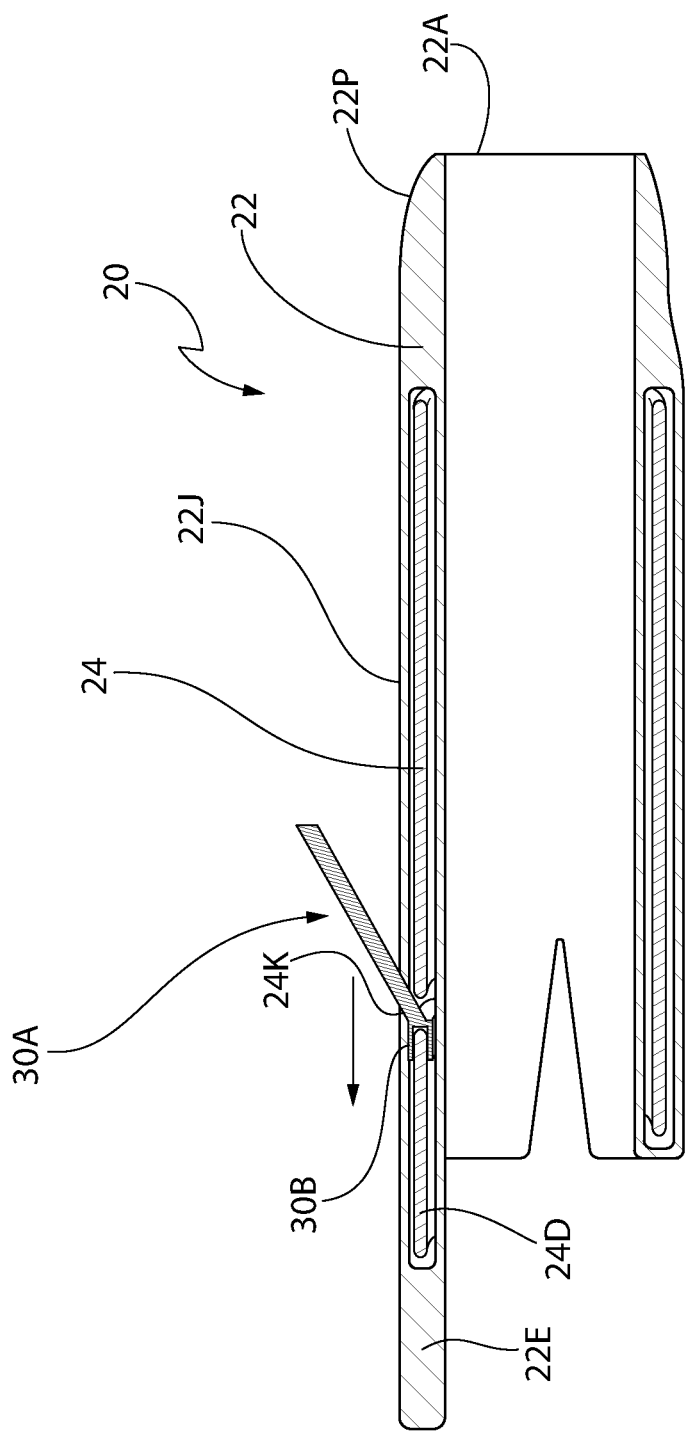
FIG. 4B depicts how the T-Device engages the inner component of the PSD through the dorsal slit to displace the PSD along the penile shaft.

There is a special "slit like" reception area 24K (FIG. 3) on the proximal dorsal area of the IC 24 for the T-Device 30 (FIG. 4-4A) to fit into (FIG. 4B). The T-Device 30 will be first placed through the dorsal mid-line slit 22J of the MC 22, then moved proximally until it reaches the IC slit 24K. The distal end 30B of the T-Device 30 will fit onto the IC proximal dorsal reception slit 24K for the T-Device 30. This "slit like" reception area 24K is where the T-Device 30 will connect to the IC 24 and allow the T-Device 30 to push the PSD 20 into the subcutaneous space of the penile shaft.

PSD: Internal Surface

The MC 22 has an inner layer 22S1 and an outer layer 22T1 (see FIG. 1H) on its dorsal and dorsal-lateral areas to form a pocket space 22I. Pocket 22I will be the space that the IC 24 will fit into, like a "'hand-in-a-glove" type fit.

The MC 22 inner layer 22S1 has an outer surface 22S3 and inner surface 22S2. The outer surface 22S3 is in touch with the inner surface 24L of the IC 24. The inner surface 22S2 is in touch with the penile tissues, specifically Buck's Fascia BF.

The MC 22 outer layer 22T1 has its outer surface 22T3 which is in touch with the penile tissues, and an inner surface 22T2 which is in touch with the outer surface 24M of the IC 24.

The ventral area of the MC 22 is a single layer 22W (FIG. 1H). The inner and outer layer surfaces 22S1/22T1 are smooth, but there will be an S-Fold undulating pattern (FIG. 2K) wherein the inner layer S-Fold is referred to as 95I, and the outer layer S-Fold is referred to as 95O. These S-folds 95I/95O have an undulating or serpentine pattern. The folds themselves will have a smooth surface, but the undulating pattern of the folds will give them a slightly "bumpy" feel to the finger touch. This particular configuration forms the PSD-S-Fold 20A discussed earlier. The PSD-S-Fold 20A will be manufactured as a two piece, MC 22/IC 24 configuration.

Variations of these undulating or serpentine patterns are shown in FIGS. 2J and 2L. In particular, FIG. 2J shows the PSD-wavy-fold 20A1 wherein the inner layer 22S1 and outer layer 22T1 comprise a less undulating or "wavy" serpentine pattern which are designated 95I' and 95O', respectively. Similarly, FIG. 2L shows the PSD-Tight-S 20A2 wherein the inner layer 22S1 and outer layer 22T1 comprise an excessive undulating or tight-turning serpentine pattern which are designated 95I" and 95O", respectively.

PSD and Penile Intra-Op Testing

The PSD 20 will not contain any visible slits on its outside surface. The only slits to be found will be the suture slits 24G in the IC 24 which will be hidden from view under the lateral mid-line slit 22Z (FIGS. 2B-2E). Underneath the suture slits 24G and aligned therewith are the suture slits 22N in the inner layer 22S1 of the MC 22. Certainly, in those PSD embodiments where no IC 24 is used, the suture slits 22N will be directly available and concealed under the lateral mid-line slit 22Z. It should be understood that, as an optional design if needed, a 1 mm port slit 24O (FIGS. 2C-2D) may also be provided in the IC 24 for saline injections to induce an erection during intra-operative testing; this port slit 24O would also be concealed under the lateral mid-line slit 22Z and there would be a corresponding slit (not shown) in the inner layer 22S1 of the MC 22 to permit passage of the needle for the saline injection into the penile shaft PS. Other locations for injection for erect testing will include the proximal ventral side of the penile shaft PS.

PSD and Penile Anchoring

Four or more suture anchoring locations 22N are provided into the distal lateral end and possibly additional more proximal locations if needed, of the PSD 20. The sutures S pass through the inner layer 22S1 of the MC suture slits 22N, and the IC suture slits 24G, and then directly into and then out of Buck's Fascia BF and the Tunica Albuginea TA of the penile tissues. Then a knot is formed. This suture S will mount the PSD 20 onto the penile tissue and stabilize the two MC/IC 22/24 and keep the PSD 20 from moving during flaccid states, erect states, and during intercourse. Additional anchoring locations in the MC/IC 22/24 may be provided to attach or mount the IC 24 to the MC 22 directly.

After suture placement and suture knots are formed, the knots are properly positioned as to not touch the undersurface of the penile skin. The knots will either be tucked below the MC outer layer inner surface 22T2, which knots will also sit on top of the outer surface 24M of the IC 24. The suture knots will never be in contact with the penile skin/dermis or fascia tissues.

Additional anchor locations throughout the PSD 20 length may be provided. If only distal anchors are used, then only partial and minimal distal degloving (pulling the penile skin down one half to 1-inch proximal to the circumcision incision, e.g., like partially pulling down a pair of pants) of the penile skin is performed and a decreased risk of infection and tissue trauma results (this is desirable).

PSD: Forces, and Tissue Involvement During the Penile Flaccid and Erect States

The PSD 20, once inserted and mounted, exerts forces onto the penile tissues and vice versa. The objective is to balance these forces to eliminate undue tissue stress and pressure onto the out-stretched flaccid and erect penile tissues, especially during intercourse or sexual activity.

Flaccid Partial, Optimal, and Supra Optimal Lengthening

The penile retraction force, which is exerted primarily in the flaccid state, is countered by the PSD 20 for partial, optimal, and supra optimal flaccid lengthening. This PSD 20 will provide a counter force which will be applied and simultaneously substantially limit or eliminate the PSD 20 direct tissue tension or pressure on the sub-glans (high risk area) or any other penile tissue areas. Long term PSD 20 use is accomplished by the appropriate design characteristics in addition to the proper selection of material, durometer, thickness, shape, and mounting techniques.

Erect Partial and Optimal Lengthening

The penile retraction force, which is exerted in the erect state, is countered by the PSD 20 for partial or optimal erect lengthening. This penile retraction force, which is exerted by the retraction of the out-stretched penile shaft and during the erection process, is, in some cases, can be high. This PSD 20 will provide a counter force which will be applied and simultaneously substantially limit or eliminate the PSD 20 direct tissue tension or pressure on the sub-glans (high risk area) or any other penile tissue areas. Long term PSD 20 use is accomplished by the appropriate design characteristics in addition to the proper selection of material, durometer, thickness, shape, and mounting techniques. Having a thicker Main Component and Internal Component, in addition to the possibility of additional anchoring locations, will be important to stabilize the penile shaft and prevent untoward pressure points on the penile tissues.

Proximal Forces

The two primary areas where forces are exerted on the penile and pubic tissues are at the distal and proximal ends of the PSD 20. The proximal area of the penile shaft and pubic area can handle a fair amount of force considering that the tissue makeup is primarily ligamentous and bony. The distal area of the penile shaft is the most fragile and sensitive area to be concerned about. The PSD 20, without anchoring via sutures S, exerts high force or tension directly on the distal sub-glans area. That is why suture mounting of the PSD 20 is necessary to divert these forces to the underlying very strong ligamentous Buck's and the Tunica Albuginea penile shaft fascial tissues.

A patient having the PSD 20 implant in over time will result in the penile shaft collagen and elastic fibers to stretch out, resulting in less retraction or recoil forces. This is favorable, especially at the distal shaft area. This collagen and elastic fiber 'stretch out' is also favorable if the patient wants to be "re-stretched" by removing the current PSD 20 and placing a longer one in. This will result in more lengthening of the erect penile shaft.

Distal Forces

There are two primary areas of concern regarding forces that are exerted on the penile tissues, the proximal pubic and distal sub-glans areas. The sub-glans area, located distally, is of primary concern.

The sub-glans area requires the greatest protection. This area is the primary source of irritation and pain if too much pressure is exerted on this penile tissue over time. If any long term, even minor force, is applied to this area, skin irritation, pain, and even skin ulceration is possible. Considering this, sutures are used to mount the distal area of the device onto the very strong ligamentous type tissues of the penile shaft, the Tunica Albuginea and Buck's Fascia. This suture mounting prevents movement of the PSD 20 in a distal direction, preventing PSD 20 pressure from being directly transmitted onto the glans and sub-glans tissues. Anchoring sutures are placed in the distal area of the PSD 20 and the knots are placed, as previously specified, in direct contact with Buck's Fascia BF, or placed on the outer surface of the IC 24 and under the outer layer of the MC 22. When force is placed on PSD 20, either through intercourse, etc., the force exerted onto the PSD 20 will be diverted and transmitted away from the sub-glans area and to the mounting sutures. Then the stress or force placed on the mounting suture will be transmitted onto the strong ligamentous type fascia, the Tunica Albuginea TA.

It should be noted that knots are not sensed or felt by the patient since they are not in direct contact with the penile tissues.

In general, the PSD 20 is designed to distribute the forces in the broadest fashion and to limit or eliminate the potential for long term inflammation and trauma. It should be noted that these are the main issues with prior art penile implants—high tissue pressure irritation and pain in this sub-glans area, in addition to skin ulceration and protrusion, which is causing many patients to have it removed.

If anchored correctly and the proper PSD 20 size and shape is selected, the long-term prognosis is favorable. Between mounting the PSD 20 at the distal shaft area and eventually the penile shaft collagen and elastin fiber stretching over time (which would decrease penile recoil forces and PSD 20 pressures on the penile tissues), this significantly helps reduce or eliminate sub-glans area stress, irritation, and potential pain.

Inwardly-Directed Radial Forces, $F_{RI}$

PSD 20 inwardly-directed radial forces $F_{RI}$ are kept at a minimum. These forces play a moderate roll in stabilizing the out-stretched flaccid or erect penile shaft; however, these forces need to be kept at a minimum, so blood flow is not constricted or limited during the erection process.

The MC 22 comprises a stretchable elastic silicone elastomer. Placing the MC 22 on the penile shaft is similar to placing a stocking on a leg. The MC 22, like a stocking, will exert a minimal or very low inwardly-directed radial force, $F_{RI}$. This inwardly-directed radial force exerted from the MC 22 is transmitted onto the penile shaft tissues, particularly Buck's Fascia BF, Tunica Albuginea TA, Corpora Cavernosa CC, Corpora Spongiosum CS, and associated nerves, blood, and lymphatic vessels.

This inwardly-directed radial force $F_{RI}$ is exerted during the flaccid state and, more so, the erect state.

During the flaccid state, the MC 22 is designed to not exert excessive inwardly-directed radial force $F_{RI}$ and hinder or prevent urine flow.

During the erect state, the MC 22 is designed to not exert excessive force to prevent blood flow into the corpora tissues during the process of erection in two primary ways: the first is the S-Fold 95I/95O pattern design found in the inner and outer layers of the MC 22 (FIG. 2K). These folds 95I and 95O will allow the beginning erect girth expansion to occur easily, and with minimal inwardly-directed radial force $F_{RI}$ by the simple unfolding of the S-Fold 95I/95O. When the S-Folds 95I/95O have completely unfolded, the silicone material of the MC 22, which is elastic and very stretchy, will stretch out easily for the balance of the erect girth increase until the full erection has been achieved. The IC 24 does not play a significant role in exerting inwardly-directed radial force since the IC 24 has a C-shape and is not a complete tubular structure, like the MC 22. Considering this, the IC 24 will simply "open up" during the erection process. In addition, the IC 24 will have potential outwardly-directed radial force to exert, so the IC 24 will negate some of the inwardly-directed radial force exerted by the MC 22.

During the erect state, and during the sex act inwardly-directed radial forces $F_{RI}$ are exerted. The PSD 20 may add some additional inwardly-directed radial force $F_{RI}$, and this force will not be excessive as to increase the tension high enough to push blood out (lose erection) during the sex act itself.

The PSD 20 exerts a minimal amount of this force, which not only helps oppose the penile flaccid retraction force by its "grip" on Bucks fascia/Tunica preventing its retraction, but also the PSD 20 being a physical obstacle, being 'seated' in the pubic pocket space and mounted at the penile distal end, in the path of retraction and maintaining length as well.

There is a pressure differential that needs to be maintained. The inwardly-directed radial force $F_{RI}$ of the PSD 20 also interacts with the outwardly-directed radial force $F_{RO}$ from the erection process. This becomes significant because a pressure differential needs to exist, otherwise if the amount of blood flow pressure needed to cause an erection is equal or lesser than the inwardly-directed radial force exerted externally from the device, the erection will not occur. In addition, if the PSD inwardly-directed radial force $F_{RI}$ exerted is added to the external force of the sexual act, the addition of both forces should not exceed the ability of the penile tissues to retain the blood within the corpora. The outwardly-directed radial force exerted by the IC 24, which will counter and negate some of the inwardly-directed radial forces of the MC 22, will provide the appropriate differential force needed for the erection to occur.

Outwardly-Directed Radial Forces, $F_{RO}$

Outwardly-directed radial force $F_{RO}$ is exerted by two different mechanisms. The primary outwardly-directed radial force is exerted by the blood flow entering into the penile shaft during the erection process.

The outwardly-directed radial force $F_{RO}$ exerted by this erection blood flow must exceed the inwardly-directed radial forces $F_{RI}$ externally applied from the PSD 20 and the act of sex itself. To achieve this differential in pressure, allowing the outwardly-directed radial force $F_{RO}$ not to be diminished appreciably, two main factors are involved. First, the MC 22 is unfoldable and stretchable, and exerts minimal inwardly-directed radial forces $F_{RI}$, and, secondly, the IC 24 is "spring-loaded", meaning that when the IC 24 is inserted into the MC 22, which is shaped into a flat sheet, is bent or partially closed first to then fit into the MC 22. This "spring-loaded" mechanism allows the IC 24 to exert an outwardly-directed radial force $F_{RO}$ on the MC 22 thereby countering and limiting the net inwardly-directed radial force $F_{RI}$ upon erection.

In addition, the MC 22 itself comprises one large pocket space that extends proximally 22IP, distally 22ID and laterally 22Q (FIG. 2G) for the IC 24 to insert into. This pocket space holds the IC 24 firmly onto the MC 22. The IC 24 provides additional outwardly-directed radial expansion force allowing greater ease of expansion under certain situations (some patients, for example, may mount a weak erection so even moderate inwardly-directed radial forces $F_{RI}$ may thwart the erection process).

Penile Human Anatomy, Physiology, and Safety Considerations and Flaccid-Erect States, and Posture in Relation to the PSD 20

The erect, and especially the flaccid penis, will bend, shorten, lengthen, twist and go through all those motions and in combination of all those motions as well. The PSD 20 is designed with an elastic stretchy silicone material to bend, shorten, lengthen, twist, etc., to a great degree, thereby accommodating for these motions. If a rigid device, such as other patented devices, is placed, all of these motions would cause moderate pressure points directly on the penile tissues. It can be appreciated trying to bend a flaccid penis with a hard-rigid device in place—this would cause the rigid device to dig into the penile tissues and cause irritation and pain.

The PSD 20 is designed with soft materials, rounded and tapered edges, flexible areas, etc., to avoid tissue injure and irritation. During normal physical activity, such as squatting down or in a seated position, the penis alters its position due to its attachment to the pelvis pubic bone and ligaments. When the pelvis moves or rotates, the penis moves as well. Considering that the PSD 20, which is now attached by sutures to the penile fascia, will move with pelvic motion so it is imperative that the PSD 20 does not cause excessive stress or pressure on the penis, especially at the suture anchors at the distal portion of the penile shaft, or surrounding tissues during pelvic movement and thus penile movement. For example, during a full squatting motion, the penis pulls inward due to the pelvic rotation that occurs. If the penis pulls inward, then the PSD 20 pulls inward as well. The dorsal side of the PSD 20 moves inward and in parallel step with the dorsal side of the penis, thereby avoiding pressure stress issues here. The ventral side of the PSD 20 moves inward (proximal) but has the potential to place stress on the ventral surface of the penile shaft and other tissues if there is no accommodation for this inward movement. Therefore, to avoid PSD 20 proximal movement stress on the penile tissues, there will be several safety designs to prevent tissue injury. The first safety design will be the rounded edges 22DT (FIG. 1N) of the proximal ventral end 22D of the Main Component. The rounded edges will promote a sliding motion along the tissues, instead of a sharp 'digging' in effect resulting in irritation and possibly pain. A second safety design is the MC proximal lateral V-cut, 22O, will be placed in the proximal lateral area of the MC 22. An IC proximal lateral V-cut 24E, will parallel the 22O, and will be placed in the proximal lateral area of the IC 24. These V-cuts 22O/24E will allow the proximal end of the PSD 20 to widen and allow for a dorsal-ventral expansion, or drop down, at its most proximal area. This allows tension relief and prevents excess pressures on penile and surrounding tissues when the penis is moving in a proximal direction or in a dorsal bending position.

During ventral or downward bending motions the concave side of the penis (ventral side) will shorten and move the PSD 20 proximally. When the PSD 20 moves proximally, it will slide as it moves, not tearing or gripping penile tissues. In addition to the ventral side of the PSD 20 being shorter in length to allow proximal movement without interfering or abutting up to tissues, the proximal area of the PSD 20 has a proximal lateral V-cut 22O/24E that will allow this section to "drop down" in a ventral direction if pressure is placed on the area. This V-cut area will provide "give" to prevent unnecessary pressure to be exerted on the proximal edge of the PSD 20 and the penile tissues. Lastly, the PSD 20 will shorten, to some degree, by material compression.

During dorsal or upward bending motions, the concave side of the penile shaft will shorten. Considering the PSD 20 on the dorsal surface extends to the pubic pocket space 50 (FIG. 8E), the PSD 20 will not be able to "slide" in the proximal direction. Considering the PSD 20 is sutured into place at the distal area of the penile shaft, the PSD 20 cannot slide distally. Since the PSD 20 is made of elastic materials it will shorten when compressed to some degree, and this will help keep pressure off of the distal suture anchor locations. In addition, the IC 24 has a plurality of V-cuts 24H on the dorsal surface. When the penis bends in a dorsal or upward direction, the dorsal V-cuts 24H will approximate, thereby shortening and not lengthening and thereby placing minimal to no pressure on the proximal pubic nor distal suture anchor locations. During the dorsal bending the MC 22, which is made of silicone material that is very flexible and stretchy, will simply compress and also lift upwards some, like bulging, to compensate for the shortening.

Elongation, by physical pulling whether in the penile flaccid or erect state, will place minimal expected stress on the distal suture area of the penile tissues. Regarding the proximal area, and because the PSD 20 is not permanently fixed or mounted at the proximal area, the PSD 20, if pulled or elongated, will simply slide distally (and slightly out of the pubic pocket temporarily). Pushing down or shortening motions will cause the PSD 20 to compress, slide proximally on its ventral side, the proximal lateral V-cuts will widen, the MC 22 will buckle up a little, and the IC 24 plurality of V-cuts will approximate, and will prevent excessive pressure to be exerted on the distal suture anchor areas and pubic pocket area. In addition, the dorsal and ventral bending safety features will also assist in relieving stress or pressure with shortening motions. Twisting motions, which is a combination of the above, will be accommodated by the aforementioned safety mechanisms.

PSD and Flaccid-Erect State Penile Position

The penis P normally hangs downward in the flaccid state, and then projects upward and outward in the erect state. Upon implanting the PSD 20, the penis P will also tend to project downward in the flaccid state. The PSD 20 will, in addition, drop downwards with gravity, due to the weight of the device 20, and due to the proximal end flange 24D being non-tubular and allowing the main body of the PSD 20 to easily bend downwards. The PSD 20 (and penis P) can be moved upwards and downwards if lifted with a hand for example with the easy bendability of the PSD proximal flange 22E. The PSD 20, to some degree, might not entirely drop fully in a downward position but outwards due to the scrotal position relative to the penile shaft, and the length of the penile shaft itself. The scrotum may contract inwards towards the body, and actually provide "lift" to the penile shaft PS, thus elevating it in a more upward position. The shorter the penile shaft PS the more elevated in appearance it will naturally be. This elevation, due to the scrotal contraction and/or very short penile retraction state, will lift the penile shaft PS with or without a PSD 20 implanted, so the upward projection of the penis P would be its natural position regardless.

PSD and Pressure on Penile Sub-Glans Area

The PSD 20 exerts an inwardly-directed radial "gripping" force to the penile tissues helping to stabilize the extended penile shaft PS. Even though the PSD 20 is suture mounted distally and abuts at its proximal end to the pubic bone and ligaments, this inwardly-directed radial "gripping" force, holds the tissue, to some degree, and helps prevent the recoiling or retraction forces of the collagen, elastin, and muscle fibers.

These collagen, elastic, and muscle fibers exert not only an inward "collapsing" force, but also a "pulling" force, in a distal to proximal direction. During the flaccid state this force results in a shortened deflated shrunken penis P in length and girth. These fibers exert an appreciable inward "collapsing" force, also called inwardly-directed radial force $F_{RI}$, and this is evident in the flaccid state of the penis P being retracted (shortened) and losing girth (deflated or "collapsed").

Upon physical stretch of the flaccid penile tissues, the linear recoil or retraction forces opposing this stretch are maximal. These linear recoil forces are countered primarily by the distal suture mounting of the PSD 20, the proximal abutment of the PSD 20 by the pubic bone and ligament area, and the little gripping effect of the PSD 20 material directly contacting the penile tissues. All of these "anti-recoil" factors maintain the PSD 20 in the most favorable (lengthened) position.

These anti-penile retraction elements, opposing the proximally directed linear retraction forces of the penis P, help re-direct these opposing proximally directed linear forces away from the glans and sub-glans area and onto the distal fascial tissues (via suture mounting), such as Buck's BF and the Tunica Albuginea TA fascial elements, in addition to the pubic bone and ligamentous area (via abutment of PSD 20). The PSD 20 is designed to redirect and eliminate, or at least minimize all forces directed onto the Glans and sub-glans area of the penis in order to avoid, as discussed previously, the sub-glans tenderness and pain that has been observed with patients using prior art penile implants.

PSD and Urethral Tension

Figure 9B:
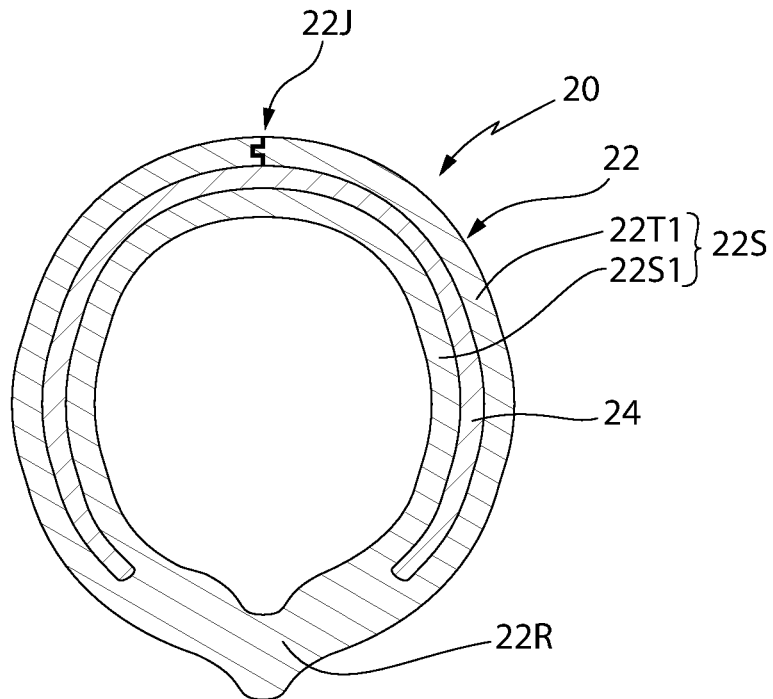
FIG. 9B is a cross-sectional view of the PSD taken along a line similar to 1H-1H of FIG. 1A showing the U-shaped ventral portion in a neutral condition.
Figure 9C:
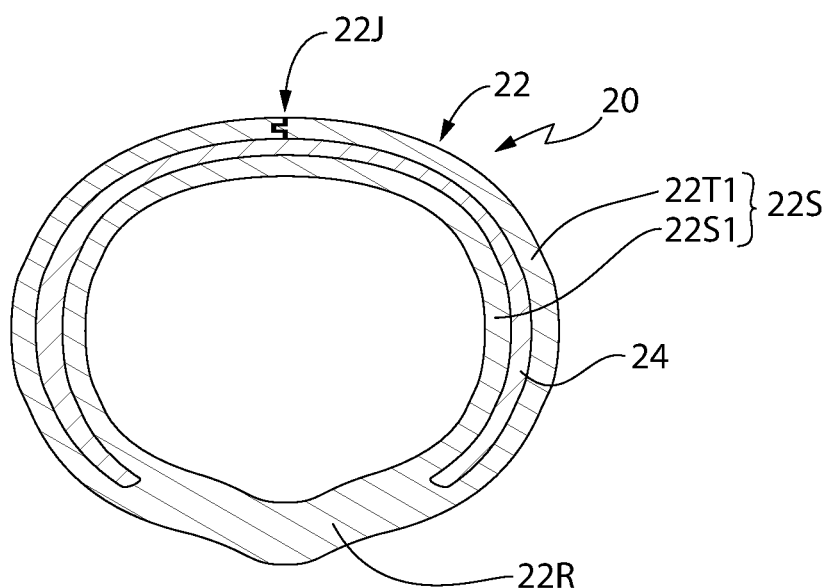
FIG. 9C is a cross-sectional view of the PSD similar to FIG. 9B but showing how the U-shaped ventral portion expands to permit urinary flow in the flaccid and erect states by relieving pressure on the urethra.

The PSD 20 is designed to avoid exerting direct or indirect pressure on the urethral area (U). If pressure is exerted in this area, a turbulent urinary flow may result and cause tissue irritation. As mentioned previously, a U-shaped mold design 22R for the MC 22 is employed to take all pressure off the urethra area U in the flaccid and erect states. Considering that the IC 24 is open on its ventral side, there is no contact on the urethral area and therefore requires no modifications. (FIGS. 9B-9C).

PSD and Erection Blood Flow Pressure Differential

The PSD 20 is placed directly on the penile shaft tissues, including Buck's Fascia BF and the Tunica Albuginea TA. The PSD 20 exerts a limited or minimal inwardly-directed radial force $F_{RI}$ eliminating or minimizing impeding the erection blood flow process.

When a normal erection takes place, blood flows into the corpora cavernosa CC and the corpora spongiosum CS with minimal opposing forces such as the retraction/recoil forces/pressure from the penile structural tissues themselves such as the collagen, elastin, and muscle cell fibers. The blood flow causing the erection must enter into the cavernosal tissues with a fair amount of (normal) pressure to overcome not only the normal retraction forces of the penile tissues but also fill the penis in its entirety, filled to capacity resulting in a very firm "hard" feel. When the PSD 20 is implanted, there is a small amount of inward pressure or inwardly-directed radial force $F_{RI}$ exerted when the erection blood flow process occurs. This minimal amount of pressure increase will not impede the erection process. The PSD 20 is designed to have four elements to limit this amount of pressure; the S-Fold 95I/95O in the inner and outer layers 22S1/22T1 of the MC 22; the very high stretch-ability of the silicone material itself; and the $F_{RO}$ exerted by the IC 24; and the outstretched position of the penile tissues which eliminates the contracting forces of the collagen, elastic, and muscle fibers that would normally be encountered during an erection process. These four factors will minimize the forces opposing the erection process.

The S-Fold 95I/95O in the inner and outer layers 22S1/22T1 of the MC 22 will simply unfold when the penile pressure from the erection process increases. When the penile erection process continues, the S-Folds 95I/95O will completely unfold, but will only allow for an erect girth expansion of 1-1.5 inches. Now, when the erect penis P continues to increase in its girth size, the second element, PSD 20 stretchability, will now allow the rest of the erect girth circumference to be realized. The third element helping reduce the $F_{RI}$ issue, is the assistance of the $F_{RO}$ of the IC 24. This $F_{RO}$ had been helping with the process of limiting the $F_{RI}$ throughout the erection girth expansion process. Note that the outer layer 22T1 of the MC 22 will contain about 50% (maybe place a range of 10-90%) less S-Fold 95O than the inner layer 95I. The MC 22 is designed to exert minimal $F_{RI}$ on the flaccid tissues, so when the erection process occurs the MC 22 stretches out easily due to the unfolding of the S-Folds 95I/95O found in both inner and outer layers 22S1/22T1 and stretching of the very stretchable silicone elastomer used. The IC 24, which is spring-loaded to exert a $F_{RO}$ immediately upon placement, provides some assistance to the $F_{RO}$ exerted by the erection process. In addition, the IC 24 is open on the ventral end which allows the IC 24 to open more freely. (FIGS. 3A-3B).

PSD and Excessive External Forces

There are many different (natural) circumstances by which external forces, other than those exerted by the PSD 20, are applied to the penile shaft. For example, many scenarios exist such as placing the penis in tight underwear, fondling during the erect/flaccid states, bending, pulling, downward pushing, masturbation, sexual act, etc. The PSD 20 is designed to "give", "buckle", and bend, while anchored and stable under such circumstances.

Dorsal Bend

When the penis P is bent in a dorsal (upward) direction, the penile shaft skin and fascia "shorten" on the dorsal (concave) side and lengthen on the ventral (convex) side. The PSD 20 adjusts by shortening; the IC plurality of V-cuts 24H approximating, and some minor upward compression and buckling of the softer Main Component 22 silicone material. This adjustment eliminates generating significant pressure or forces on the proximal pubic area abutment space and the suture mounted penile tissues at the distal penile area. If these counter anti-pressure/force elements of the PSD 20 design were not in place, then there would be too much force exerted onto the distal suture anchor points, and subsequently the glans and sub-glans areas, and the proximal pubic abutment area or pubic pocket space 50. Stress relief is accomplished by shortening the length of the IC 24 via the plurality of dorsal V-cuts 24H. See FIGS. 3 and 9-9A. Thus, when dorsal bending occurs, the V-cuts 24H collapse (see FIG. 9), thereby permitting the IC 24 to bend without causing the proximal end flange 24D to displace further within the pocket 22Q of the MC 22, and subsequently pushing the device further into the pubic pocket space 50 and tissues. In addition, a structural design including an accordion type buckling zone 22L of the dorsal proximal area of the MC 22 (as well as a corresponding buckling zone 24F of the IC 24) ensures that when the penis P is bent in a dorsal upward direction, the shortening of the penile dorsal skin and fascia coincide with a parallel shortening of the PSD 20. The proximal area of the MC 22, and the IC 24, are manufactured in a slightly wavy fashion (e.g., buckling spaces 22L and 24F, respectively) so that when excessive force is exerted, the MC/IC 22/24 bend or bow and the slightly wavy areas 22L/24F becomes wavier (the peak and trough depths of the waves increase). This design provides the "give" and relieves stress with this dorsal bend situation. It should be further noted that the MC 22, considering its very stretchable material, collapses upon itself when compressed or when force is exerted, so a wavy design may not be necessary. This feature helps in preventing excessive forces exerted on the penile tissue.

Ventral or Lateral Penile Bending

A wave "buckle" design may not be required on the lateral or ventral portions of the MC 22 because these areas do not directly abut up to any structures, so the MC 22 freely "slides down" the penile shaft PS to compensate for the decreased length of the ventral downward bent penile surface. However, when the PSD 20 slides down, it may exert pressure on the urethra U and/or other tissue components in the area. The PSD 20 design takes into account the penile ventral anatomy and the ventral downward bending of the penile shaft and the posterior movement of the PSD 20. A wave might be considered, or a built-in joint, such as the proposed proximal lateral V-cut 22O, which can be made on both of the PSDs' MC/IC 22/24. There will be a proximal lateral V-cut 22O on both lateral sides of the MC 22. There will be a proximal lateral V-cut 24E on both lateral sides of the IC 24, so when the PSD 20 moves in a posterior direction (like in a ventral bend) the PSD 20 will not only slide proximally, but "gives" at the built-in joint area allowing the PSD 20 to widen or open up. This opening or inferior drop relieves the stress placed on the ventral penile elements such as the urethra. In addition, stress relief is accomplished when the ventral length of the IC 24 is shortened, using a plurality of ventral V-cuts 24I (if needed), similar to the plurality of dorsal V-cuts 24H (if needed). Thus, when ventral bending occurs, the IC 24 plurality of ventral V-cuts 24I collapse or approximate to one another, thereby preventing further proximal ventral displacement or proximal movement and thus preventing tissue pressure and stress.

The Act of Intercourse or Masturbation—Penile Push Pull Forces

All modifications to anchor and stabilize the PSD 20 greatly assist in stabilizing the PSD 20 and preventing tissue stress points. To add additional assistance to increase force distribution, patients are instructed to use oil lubrication (S-Lube) during intercourse or masturbation. The lubrication, with the sliding motion of the hand or vaginal/anal tissues across its surfaces, transmits the pressure more evenly, with less drag or pull on the penile skin tissues, and therefore less transmission of forces onto the PSD 20 and subsequently onto the penile suture mount area and pubic bone and ligament areas. So, this sliding on the penile skin throughout the penile shaft prevents or significantly reduces excessive pinpoint force distribution (or drag on the skin and thus the PSD 20 and penile tissues) onto the distal, midshaft, and proximal shaft areas. Avoidance of this pinpoint force is critical, especially in the distal sub-glans area where the anchoring is located.

PSD and Penile Implant

PSD and Penile Foreign Body Reaction

Upon placement of the PSD 20, the body immediately responds to this implant as an "enemy", or a foreign body. This response by the body to this 'foreign body; is called a Foreign Body Reaction FBR. Considering the size and material makeup of the PSD 20, the body treats this implant as a foreign body, and thus, a Foreign Body Reaction FBR via the immune system takes place. This type of FBR reaction is common with implants, including Breast Implants, Knee and Hip Implants, etc.

The body, or immune system, encounters a foreign body or implant device, it will first need to determine if this foreign substance is dissolvable, engulf-able, or surround-able. If the device is not dissolvable or engulf-able, then the body mounts a foreign body reaction that surrounds it with collagen. This FBR that surrounds the foreign body is essentially entombing or encapsulating it and protecting the body from contact with it.

A FBR is desirable in this circumstance. The immune system "sees" this PSD 20, determines it is "foreign" and reacts by developing a collagen sheet enveloping the PSD 20 in its entirety, "entombing" it in a collagen sheet or envelop. This collagen layer developed by the immune system will prove to be beneficial providing a buffer space or another layer between the PSD 20 and the surrounding tissues, and therefore result in the PSD 20 not touching the penile tissues directly. This will provide another layer of cushion and protection from irritation as well. The new collagen formation, via the FBR, provides some stabilization of the PSD 20. Another advantage of the PSD 20 being entombed within this collagen envelope is that this protects the PSD 20 against long term degradation attempts from immune system exposure and chemical breakdown, and thereby provides longevity of the product.

PSD and Penile Ventral Area

Alternative designs of the PSD 20 are available to match the clinical situation presented. For example, the PSD 20 may comprise the same length throughout, with no proximal end flange 22E and 24D. This will result in the PSD 20 have the same length on its dorsal and ventral sides. The reason for this is that the pubic pocket space 50 (space by the pubic bone and ligament area) may not exist, in a substantial manner, in some patients. In this case, the dorsal and ventral lengths will be the same. The PSD 20 can be either manufactured without the proximal end flanges 22E/24D or they can be "cut-to-fit" as well.

Since there is space in the pubic bone and ligament area 50, the length of the PSD 20 on its ventral side will, in the vast majority of cases, be shorter in length than the length of the dorsal side of the PSD 20. In addition, the shortened length of the ventral side of the PSD 20 with the proximal lateral V-cut 22O, will also accommodate for the proximal movement of the penile shaft during squatting motions. The reason for this design is because the ventral area of the penile shaft, involving the urethra and scrotal tissues, anatomically moves proximally when a person squats down (or if the penis P is bend in a downward fashion), and the penis P is drawn into the body. This occurs because the penile shaft PS is attached to the pelvic/pubic bone and ligaments, so when the person squats down the pubic bone rotates and pulls the penis P into the body. When this occurs, the PSD 20 will also be pulled into the body as well considering that the PSD 20 is attached with sutures at the distal area. Now, if the PSD 20 is the full length of the penile erect length and the person tries to squat down, the penis P and the PSD 20 move into the body, but the problem here is that with ventral proximal motion of the PSD 20 into this area, the PSD 20 may "dig into" the urethral and scrotal areas of the penile shaft PS, thereby resulting in temporary pressure/irritation there. Even though the PSD 20 is designed to be smooth with rounded edges in all appropriate places which will allow for the PSD 20 to slide along the penile tissues, another safety mechanism, the proximal lateral V-cut 22O will allow for additional or unexpected movement of the device in case there was additional tension or pressure in that area. Considering this, the ventral side of the PSD 20 is thus made shorter in length, will be smooth with round edges, and will have a large proximal lateral side V-cut 22O to allow a ventral drop down of the ventral portion of the device 20 to relieve pressure on proximal ventral tissues. In addition, the plurality of V-cuts on the IC 24 ventral surface 24I (if needed), which will parallel the plurality of dorsal V-cuts 24H, will allow for the ventral surface of the PSD 20 to collapse closed during ventral bending thus preventing elongation of the device into sensitive urethral and scrotal tissues proximally.

PSD and Uncircumcised Patients

It is always recommended to be circumcised prior to any procedure involving male enhancement, which would include PSD 20 insertion, filler treatment, etc. The reason for this is that the foreskin, or uncircumscribed skin, is very thin and fragile. The PSD 20, or any implantable subcutaneous device may have the potential to irritate this thin skin over time. In addition, permanent filler cannot be injected, with substantial quantities, into this thin skin which results in a narrower asymmetrical and imbalanced distal penile shaft. If a patient refuses to get circumcised there is a low risk option available. If the patient desires to just have a PSD 20 placed, and not have a circumcision, then there is no issue except for a small risk of skin irritation by the foreskin area. However, if the patient wants a PSD 20 and filler treatment, then a custom PSD 20 can be designed to be thicker at the distal end to compensate for having no, or little, filler placed there.

For example, assume the patient is 2 inches in flaccid length, 3.5 inches in flaccid girth, 6-inches in erect length, and 4.5 inches in erect girth. His desire is to optimize his flaccid length and achieve a 7-inch erect circumference/girth. The patient then has the PSD inserted, which now yields a 6-inch flaccid length, 5-inch flaccid girth, 6-inch erect length, and a 6-inch erect girth. Considering that the filler treatment is next, to now increase the erect girth the additional inch desired, the filler will now be placed in the penile shaft, but little will be placed in the distal shaft "foreskin" area F of the penile shaft. The 7-inch girth goal will be reached in the proximal and mid-shaft regions, but not at the distal foreskin F location. This evidently will result in a possible girth imbalance if the foreskin area F does not accept a reasonable amount of filler. In this case where the filler cannot provide the girth gains at the distal portion of the penile shaft, the PSD 20 can be designed to be thicker in that distal region either by directly adding a SIC 24J for that space, or have a custom designed PSD 20 made, with a thicker distal end to compensate for the lack of filler placed in the distal shaft foreskin area. Either solution will achieve a much better balance. So the PSD 20, not the filler treatment, can thus provide the lack of girth at that distal shaft location. After PSD 20 placement, the proximal and mid-shaft will be 6 inches in circumference, and the distal shaft will be 7 inches. Then, after two or three filler treatments, the proximal and mid-shaft flaccid girth will reach the 7-inch size now matching the distal 7-inch girth provided by the PSD. A filler "transition" zone FTZ, will be created between the larger PSD distal end (being 7-inches in girth) and the smaller portion approximating (which is 6-inches in girth). To address this filler transition zone FTZ, filler will be placed in this area to provide an appropriate transition (from skin with filler to skin with just the PSD 20 under it) into the distal shaft area in order to provide a "feels natural" experience.

PSD Delivery Devices

Figure 1J:
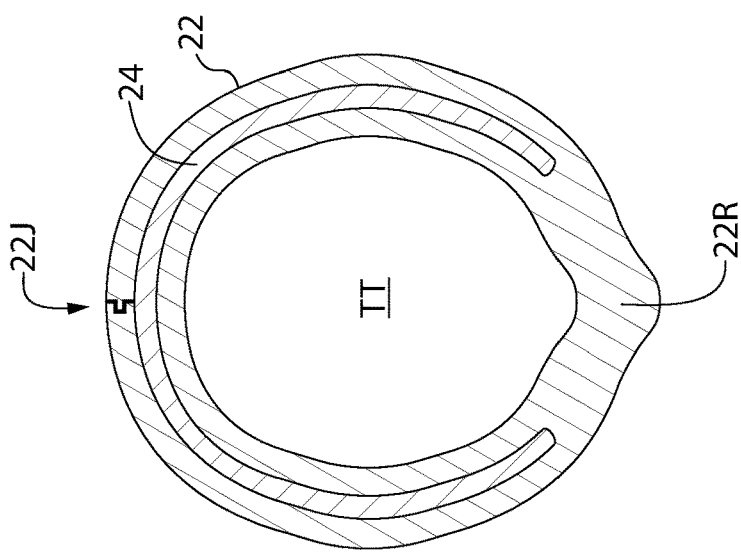
FIG. 1J is a cross-sectional view of the PSD taken along line 1J-1J of FIG. 1A.
Figure 1I:
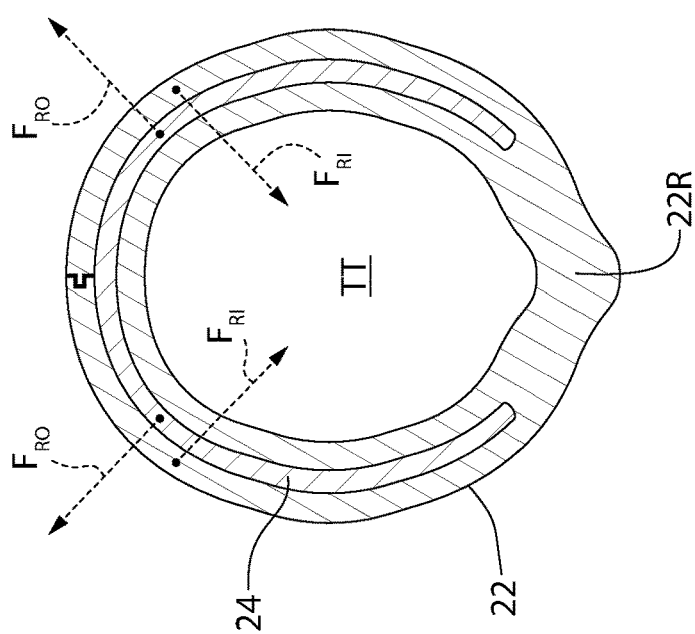
FIG. 1I is a cross-sectional view of the PSD taken along line 1I-1I of FIG. 1A.
Figure 1M:
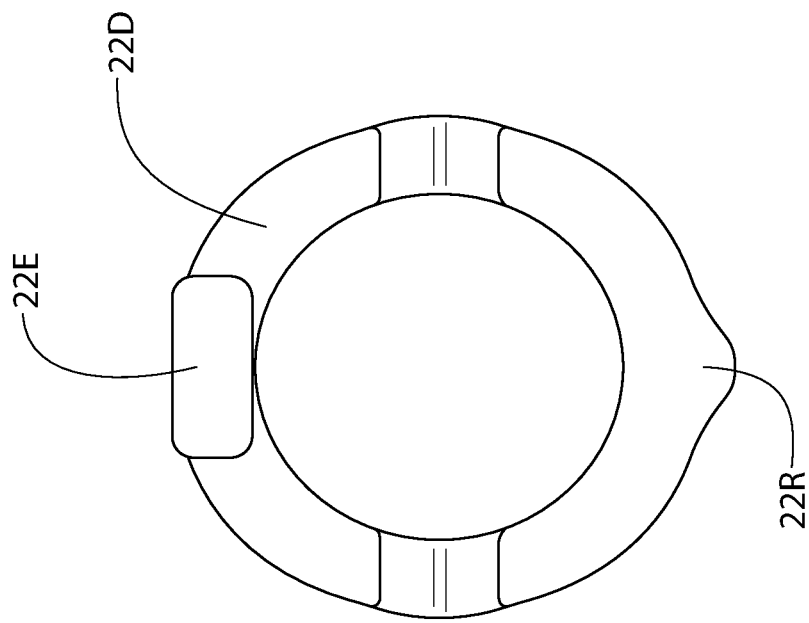
FIG. 1M is a back view of the PSD of FIG. 1A.
Figure 1L:
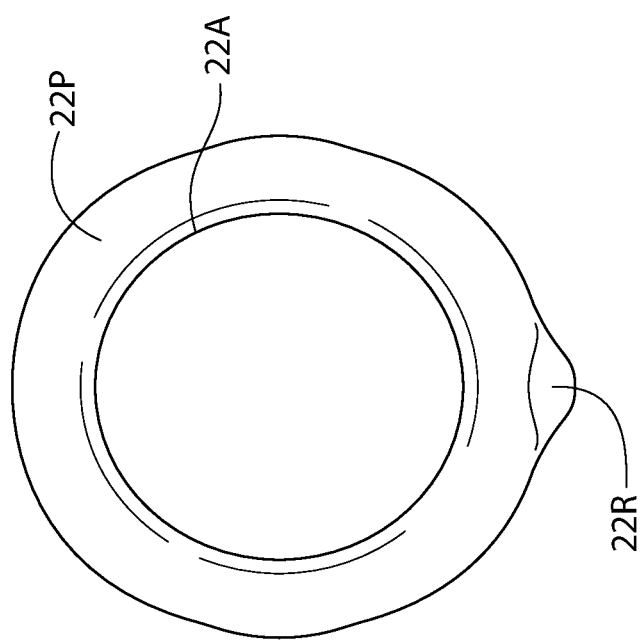
FIG. 1L is a front view of the PSD of FIG. 1A.
Figure 1N:
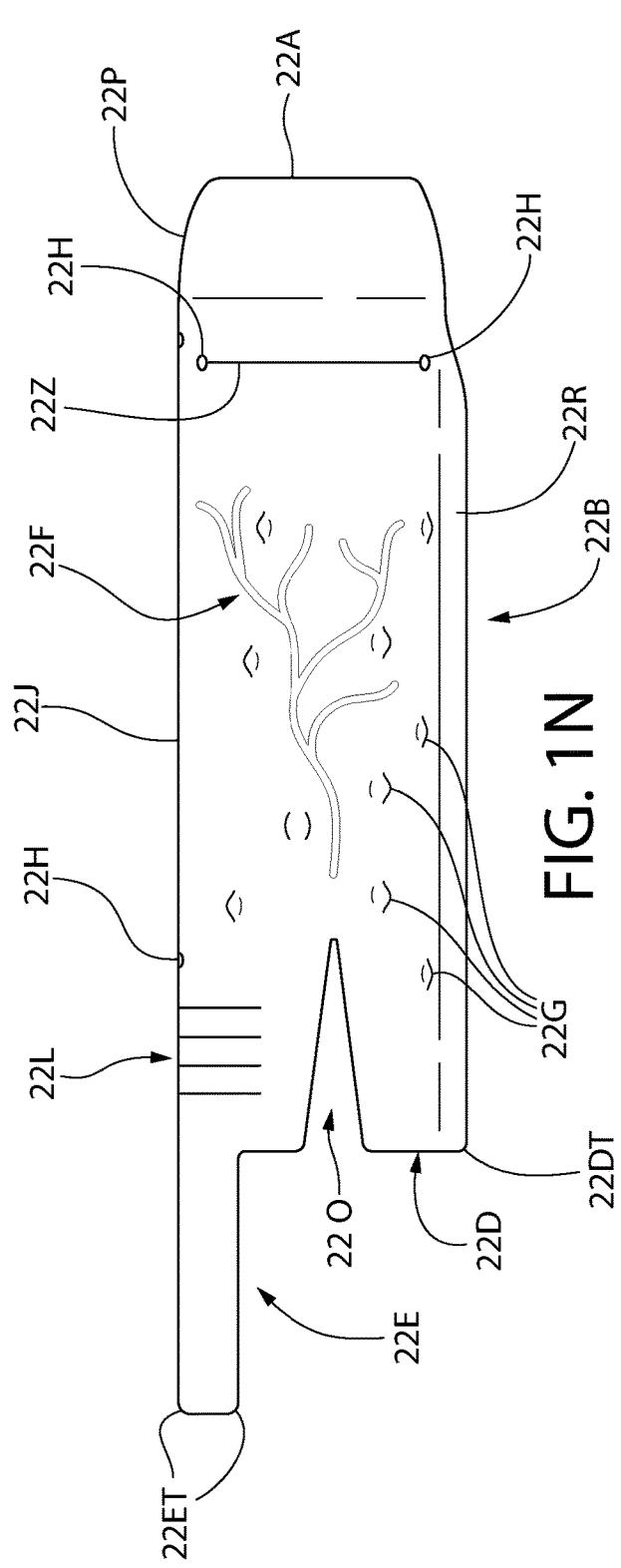
FIG. 1N is a side view of the PSD of FIG. 1A.
Figure 1O:
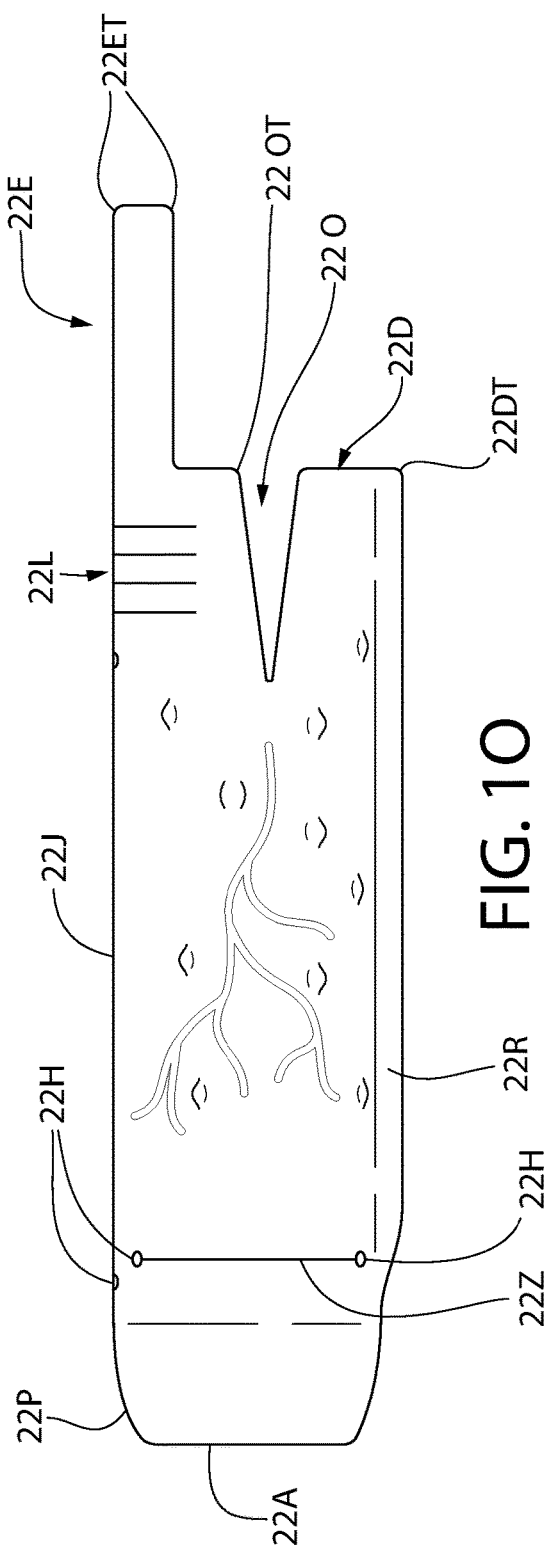
FIG. 1O is the other side view of the PSD of FIG. 1A.

The PSD 20 is delivered to the subcutaneous penile shaft subcutaneous space SS (FIG. 7B) via delivery devices. The delivery devices comprise two components; the Glans Gripper Device 28 (FIGS. 5-5A) and the T-Device 30 (FIGS. 4-4B). The Glans Gripper Device 28 is designed to be placed the PSD's tubular tunnel TT (FIGS. 1, 1J and 7B), then gently grip the glans, and with gently pulling motion of the Glans Gripper Device 28 and a pushing motion of the PSD 20, the PSD 20 will slide over the glans and into the subcutaneous space SS of the penile shaft PS. The T-Device 30 is used to assist in the pushing proximal motion of the PSD 20. The T-Device 30 will insert itself into a proximal dorsal reception slit 24K (FIG. 4B) of the IC 24. The T-Device 30 will gain access to slit 24K by being placed through the dorsal mid-line slit 22J of the MC 22. The objective of these delivery devices is to deliver the PSD 20 into the penile subcutaneous area SS, then be pulled out, leaving the PSD 20 in place. The Glans Gripper Device 28 comprises a distal end 28A, a medial portion 28B and a proximal end 28C comprising finger grips. The working distal end 28A comprises respective pads 28D on each tine of the distal end 28A.

It is preferred that the PSD internal surface 22S2 and external surface 22T3 (FIG. 1H) be lubricated with a biodegradable sterile Carboxymethylcellulose Gel Lubrication (C-Lube) to assist in sliding the PSD 20 into the subcutaneous space SS and onto the penile fascia tissue (PF) and penile skin underside (PSU) The C-Lube is a safe non-irritating Carboxymethylcellulose gel, or other very viable substitutes such as hyaluronic acid gel, or certain non-irritation and easily digestible oil.

Furthermore, it should be noted that when the PSD is implanted, the foreign body reaction FBR will surround the PSD 20 with a collagen layer. This layer entombs the PSD 20 making it unseen or invisible to the immune system.

The IC 24 and MC 22 will need to slide on one another if a plurality of V-cuts and/on the dorsal and/or ventral sides (24H and 24I) are to approximate, edge to edge (24HE/24IE, respectively). When the penis P bends, the plurality of V-cuts will approximate, thus moving or sliding within the MC pocket space 22I. Silicone rubber materials sliding on each other may result in friction, and thereby result in wear and tear on the IC 24 and MC 22. To help prevent this, Sterile Medical Grade Silicone Oil (S-Lube) may be used to lubricate the pocket space 22I of the MC 22 to allow for the IC 24 to slide on the MC 22 while the V-cuts edges are approximating or are in a sliding motion. Theoretically, if a lubricant such as Silicone Oil is used, it may need to be replenished over time. There is a potential pathway for the oil to migrate out of the dorsal mid-line slit 22J of the MC 22 and into FBR capsule space (FBCS). If this is the case, there is one solution that will help to maintain the presence of S-Lube within the pocket 22I of the MC 22, and that is to periodically (e.g., every 2 years, etc.) re-inject with S-Lube in the implanted PSD 20, i.e., inject within the pocket space 22I of the MC 22.

Main Component Dorsal Mid-Line Slit 22J

The MC dorsal mid-line slit 22J will need to be designed to help prevent leaking of the S-Lube into the pocket space 22I. This will be done by making the edges of 22J into a tongue 22JT and groove 22JG pattern (see FIG. 2A), whereby they will fit together in this fashion. It should be noted that at each end of the dorsal mid-line slit 22J is a tear reduction aperture 22H to minimize any possible tearing of the adjacent MC outer layer 22T1 during opening of the slit 22J.

PSD Delivery Technique (DT)

The PSD 20 is delivered into the penile subcutaneous space via the Delivery Technique (DT). The PSD 20 is first lubricated with C-Lube on its external and internal surfaces 22T3 and 22S2 (FIG. 1H) of the PSD 20. The user grips the T-Device 30 via a handle portion 30A and inserts a curved working distal end 30B through the dorsal midline slit 22J of the MC 22 and slides the distal end 30 along the dorsal side of the IC 24 until the distal end 30B is engaged within the IC receiving slit 24K. Once in place, the Glans Gripper Device 28 is placed through the PSD tubular tunnel TT (FIG. 7B) and grips the glans G using respective pads 28D (e.g., silicone mitts) on the working distal end 28A. Then, with a careful forward motion of the PSD 20, the T-Device 30 is pushed proximally while pulling the Glans (G) simultaneously with the Glans Gripper Device 28, the PSD 20 will slide into position onto the subcutaneous space SS of the penile shaft.

Figure 7:
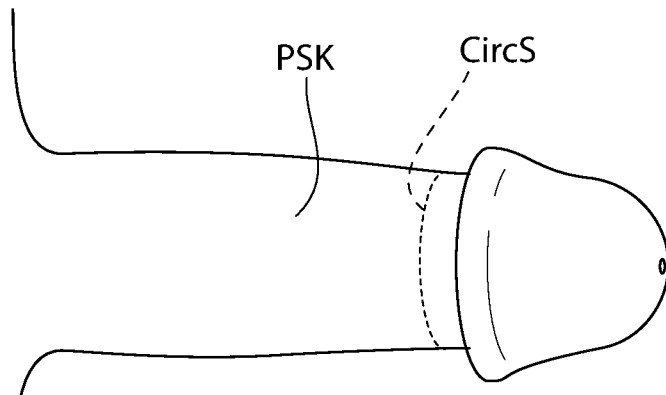
FIG. 7 shows the patient's penis prior to implantation of the PSD and where the existing circumcision scar is to be opened.
Figure 7A:
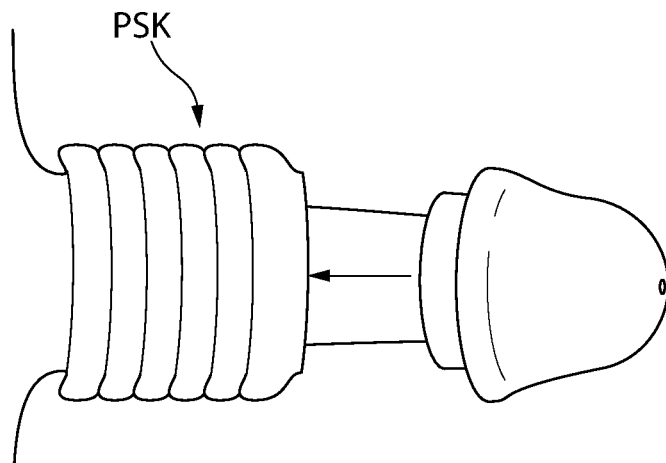
FIG. 7A depicts how the penis is degloved and the penile skin is pushed proximally toward the pubic area.
Figure 7B:
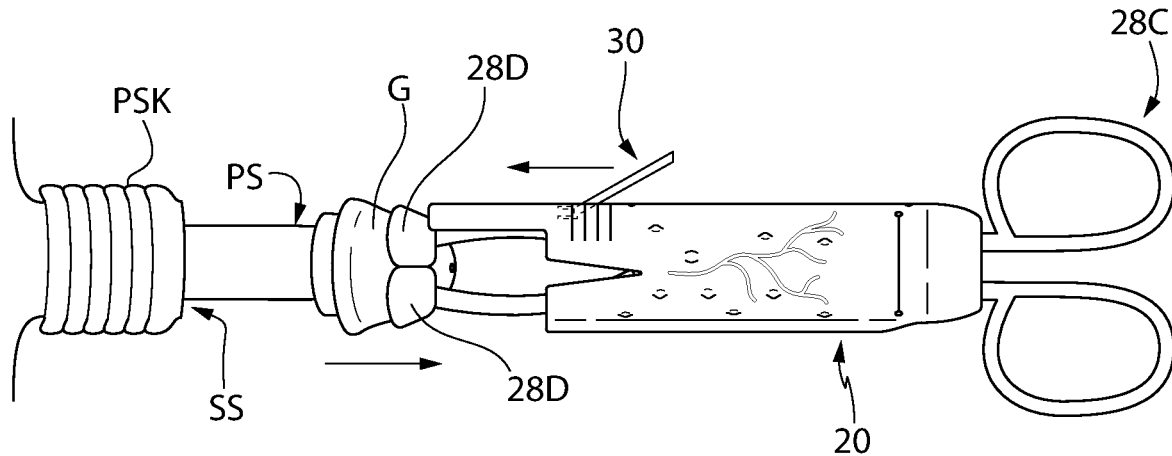
FIG. 7B depicts how the glans gripper device is used to deliver the PSD onto the degloved penis after penile measurements have been taken.
Figure 7C:
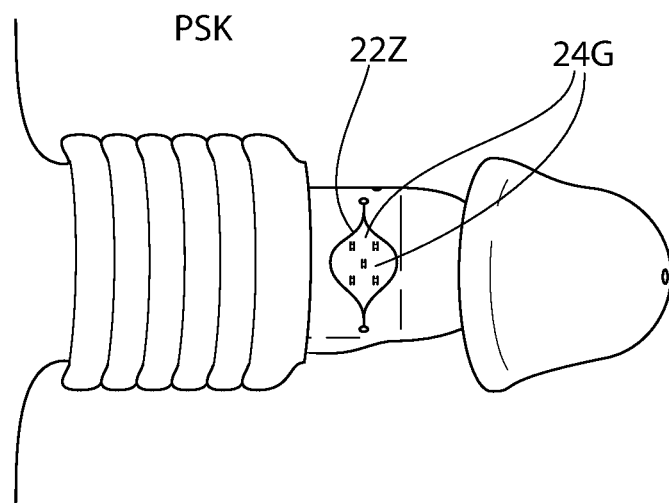
FIG. 7C depicts the suture slits of the PSD being exposed to permit pen markings on the penile shaft to be made therethrough.
Figure 8:
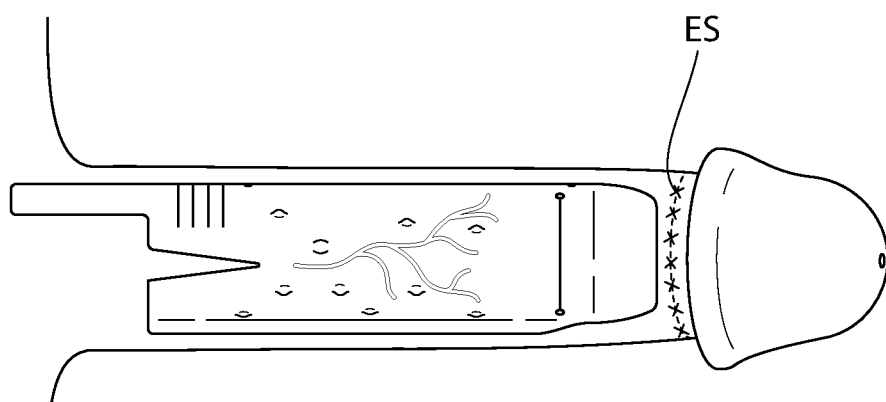
FIG. 8 depicts the PSD implanted on the penile shaft, the penile skin returned to the circumcision line and external sutures being used to close the circumcision line.
Figure 8A:
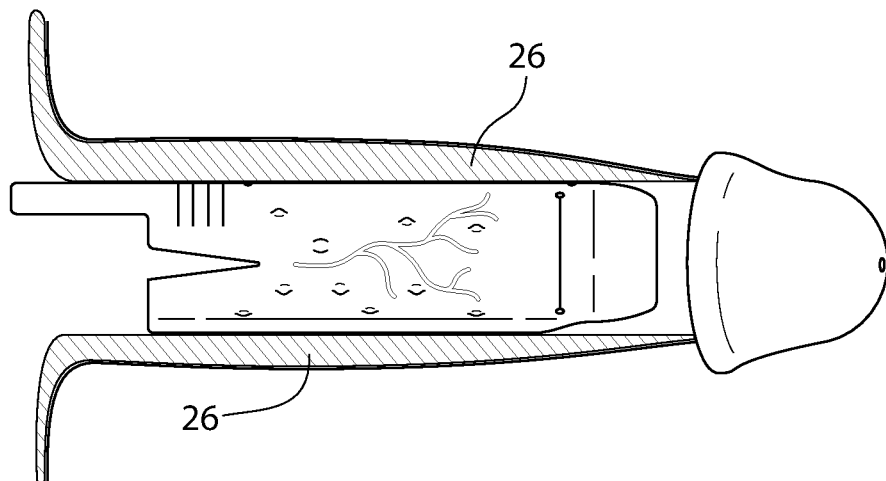
FIG. 8A depicts the additional step of implanted a filler around the implanted PSD to further increase penile girth.
Figure 8B:
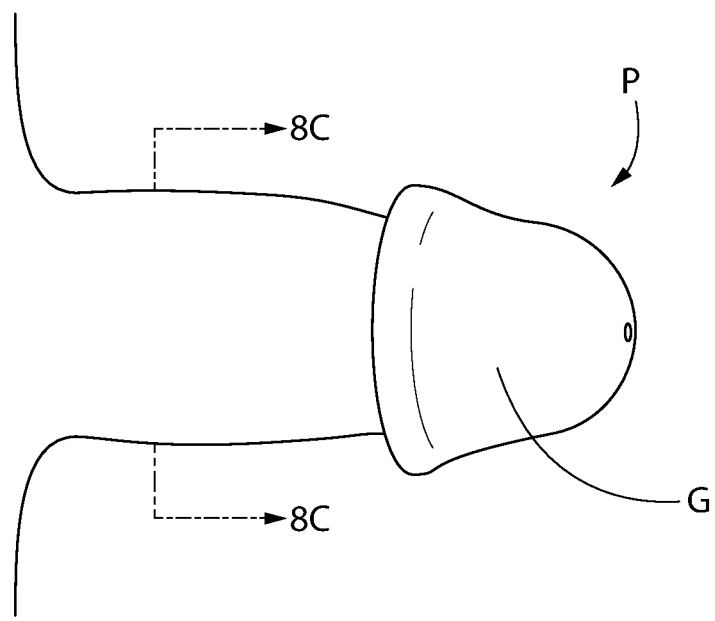
FIG. 8B depicts a flaccid penis and FIG. 8C is enlarged cross-sectional view of the flaccid penis taken along line 8C-8C of FIG. 8B.
Figure 8C:
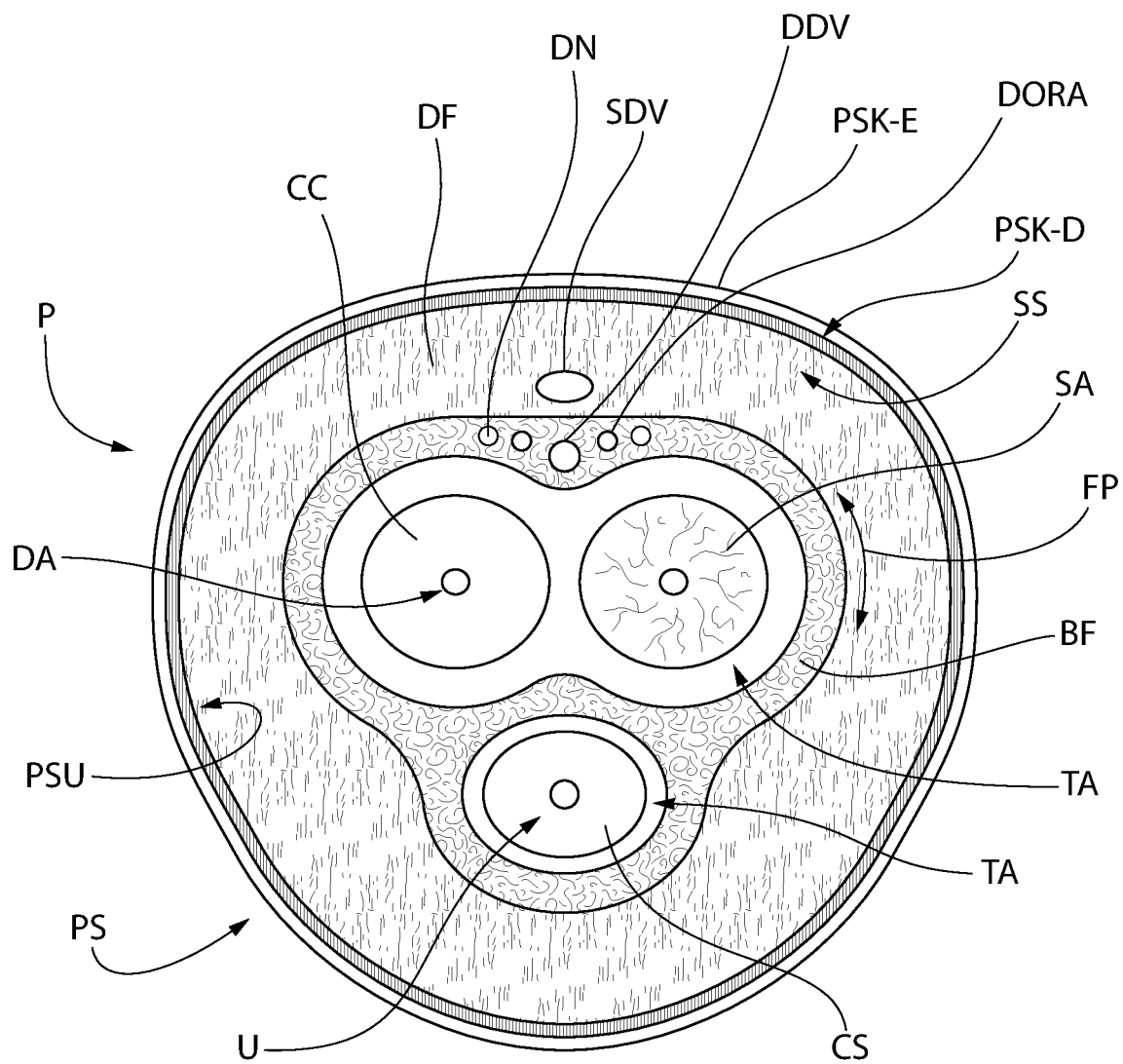
Figure 8D:
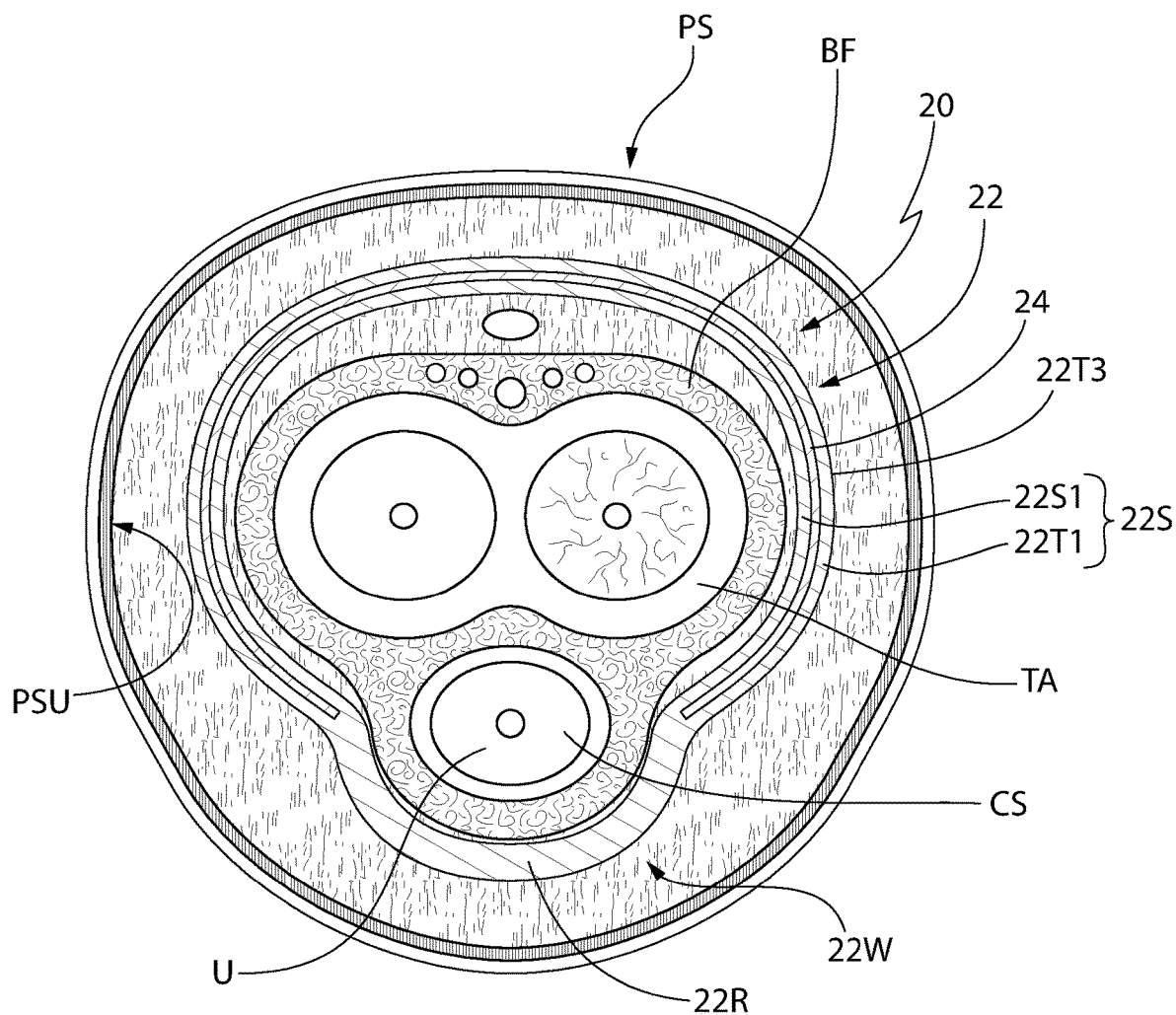
FIG. 8D is a cross-sectional view similar to FIG. 8C but showing the PSD implanted on the penile shaft.
Figure 8E:
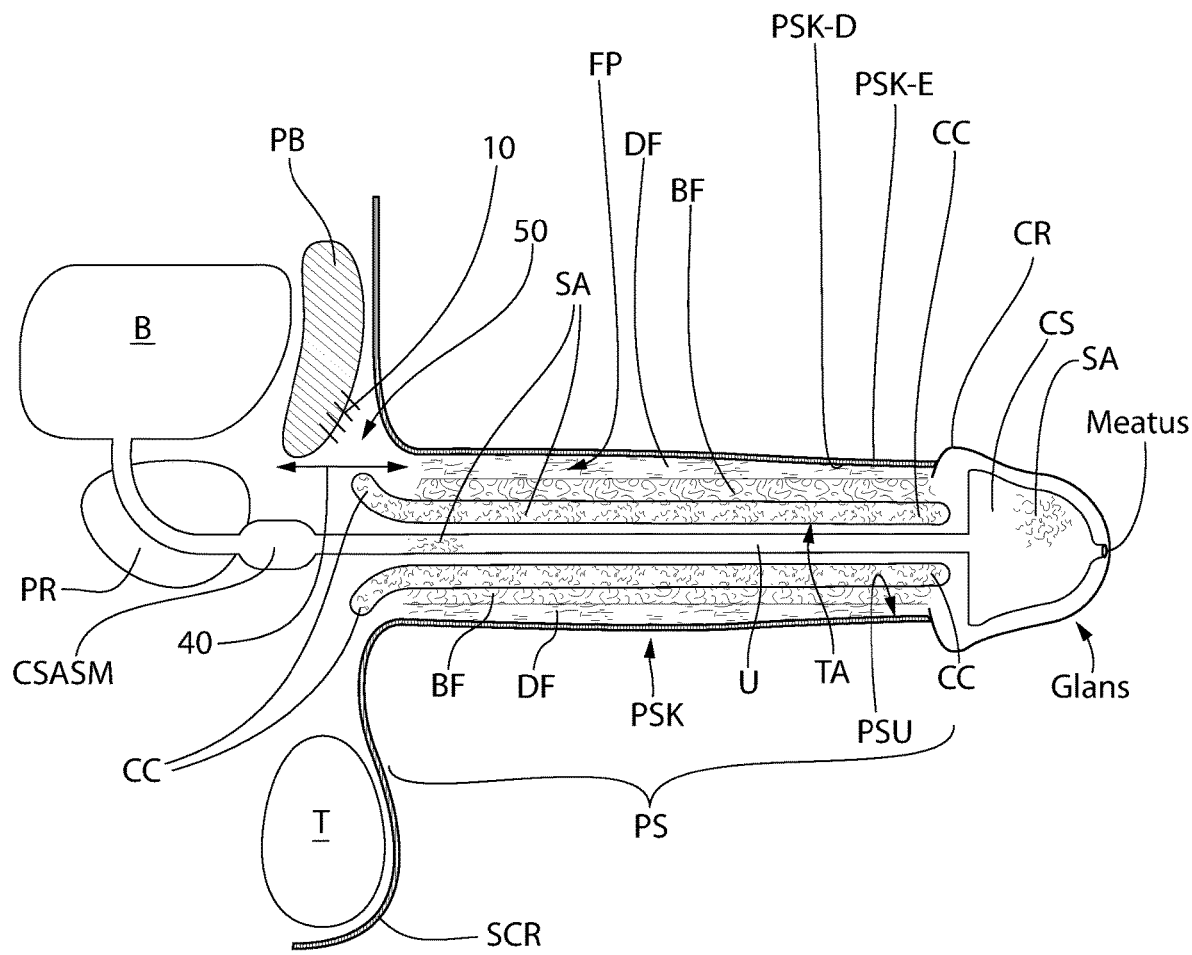
FIG. 8E is functional longitudinal cross-sectional view of a penis depicting the various vessels therein.
Figure 8F:
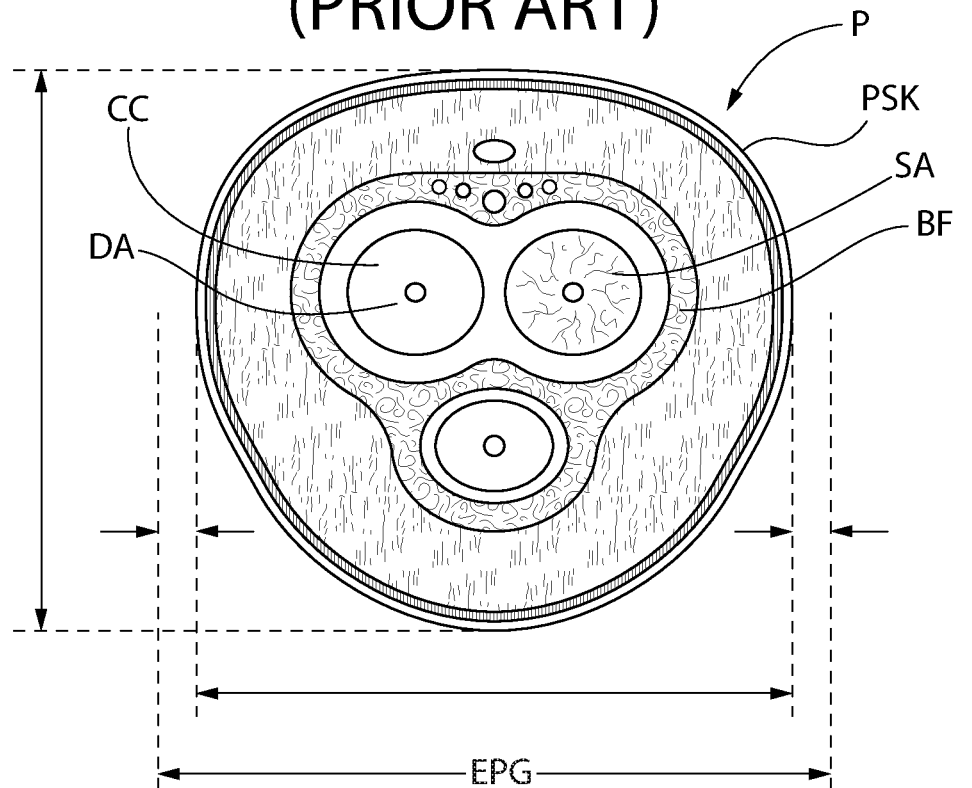
FIGS. 8F and 8G are cross-sectionals views of a penis and a penis having the PSD implanted therein to demonstrate the increased girth added by the presence of the PSD.
Figure 8G:
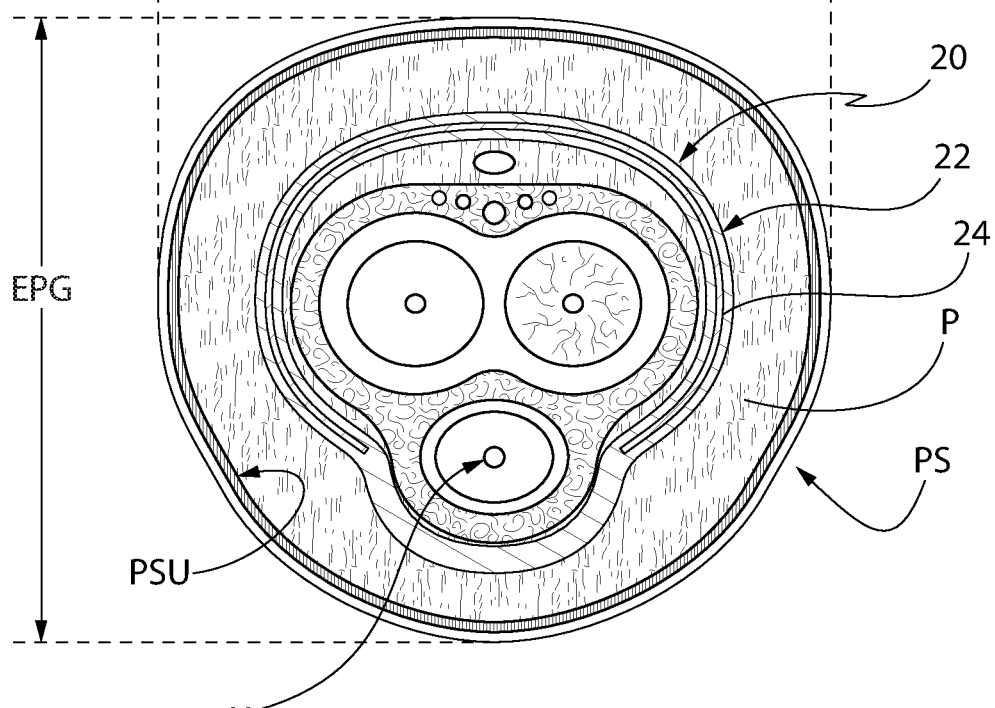
Figure 8H:
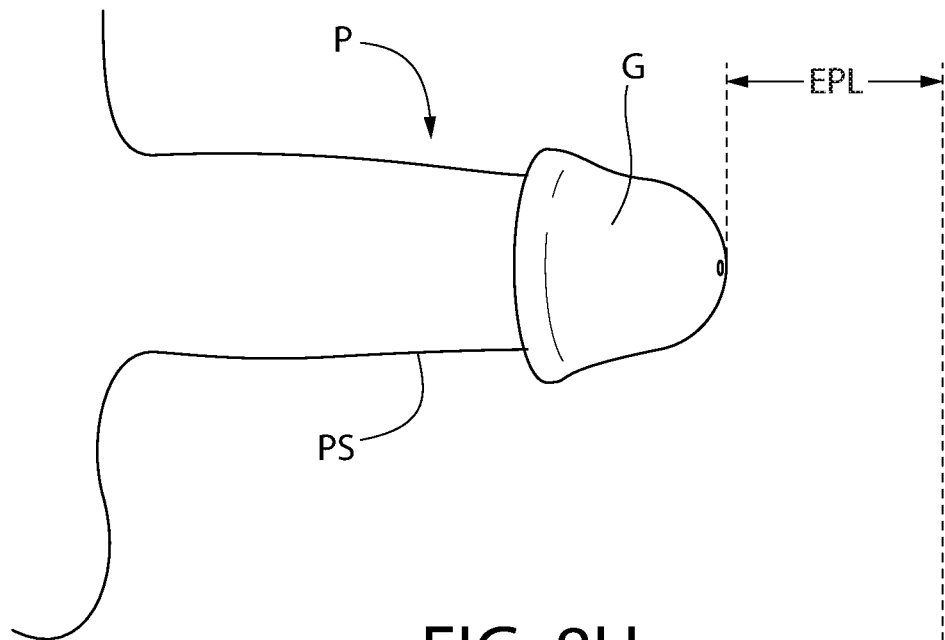
FIGS. 8H and 8I are side views of a penis and a penis having the PSD implanted therein to demonstrate the increased penile length added by the presence of the PSD.
Figure 8I:
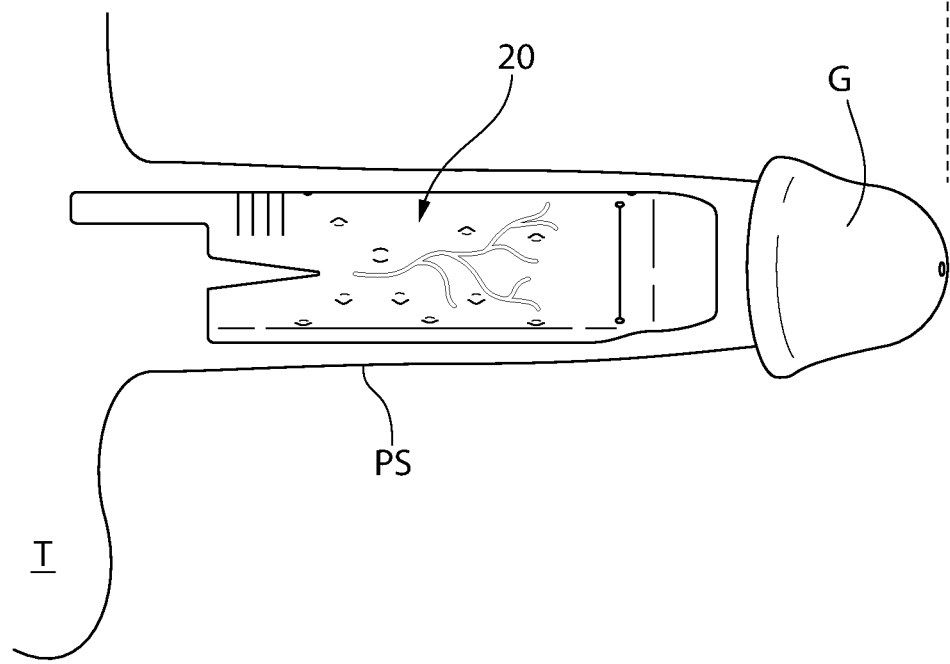
Figure 8J:
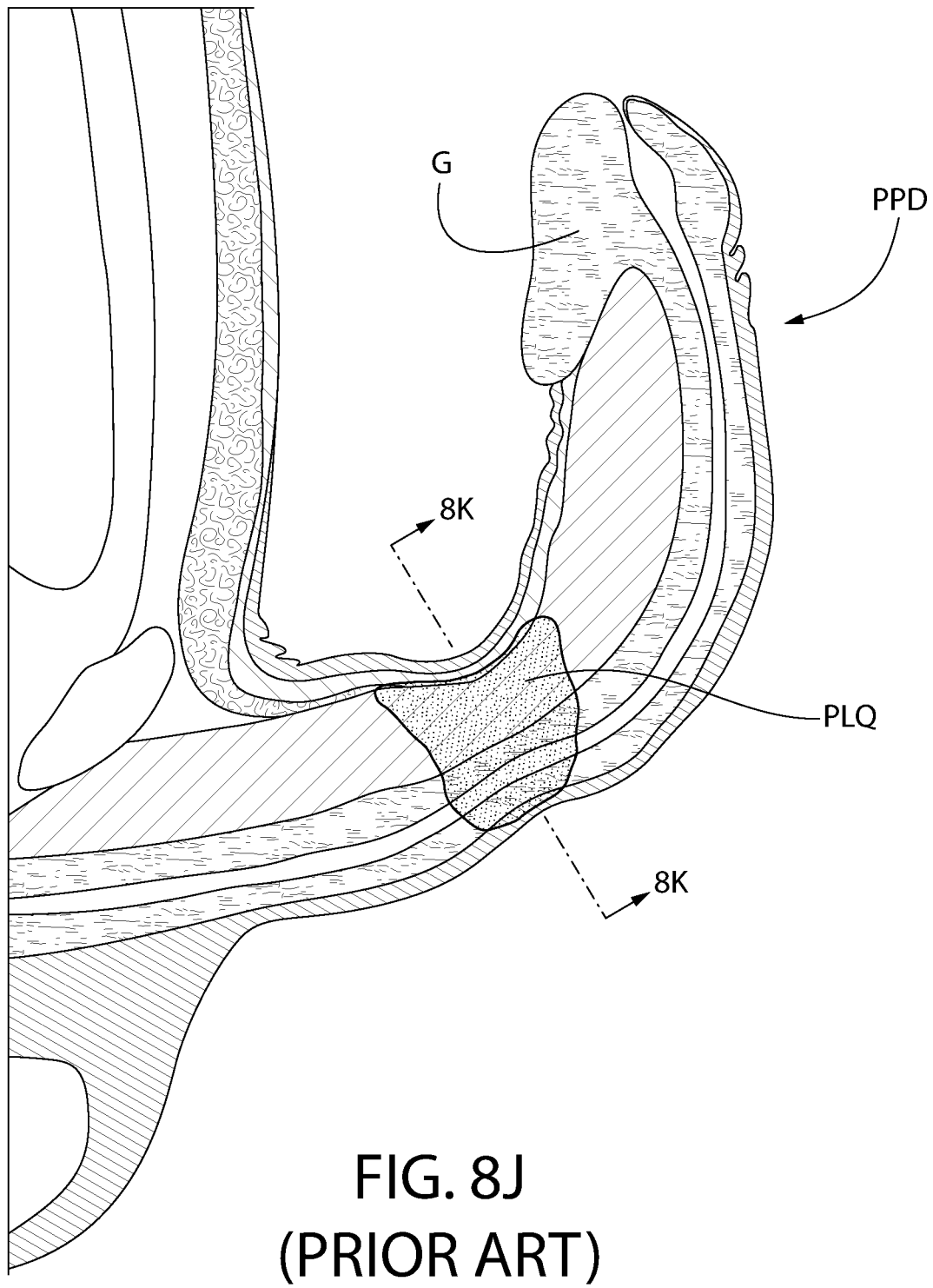
FIG. 8J is a diagrammatic view of a penis with Peyronie's Disease showing how the presence of plaque misshapes the penis.
Figure 8K:
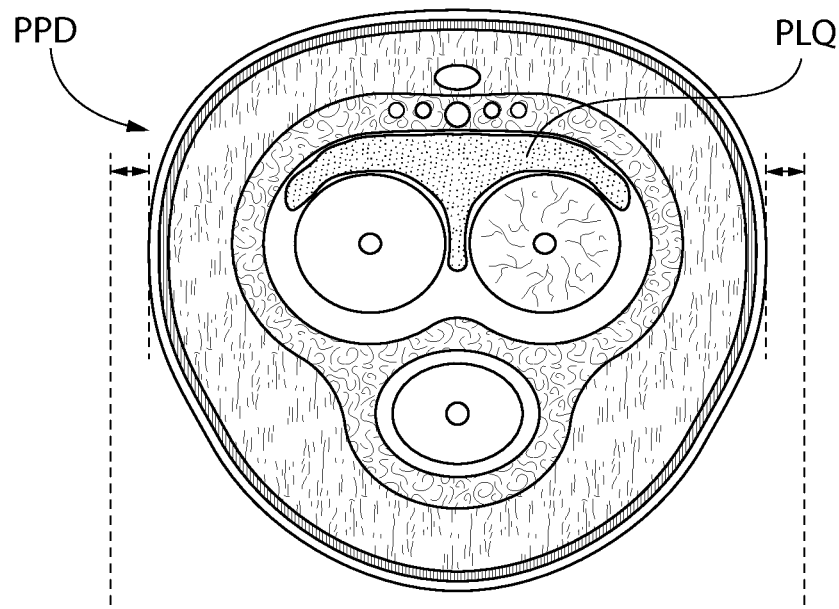
FIGS. 8K and 8L are cross-sectionals views of a Peyronie's Disease penis and a Peyronie's Disease penis having the PSD implanted therein to demonstrate the increased girth added by the presence of the PSD.
Figure 8L:
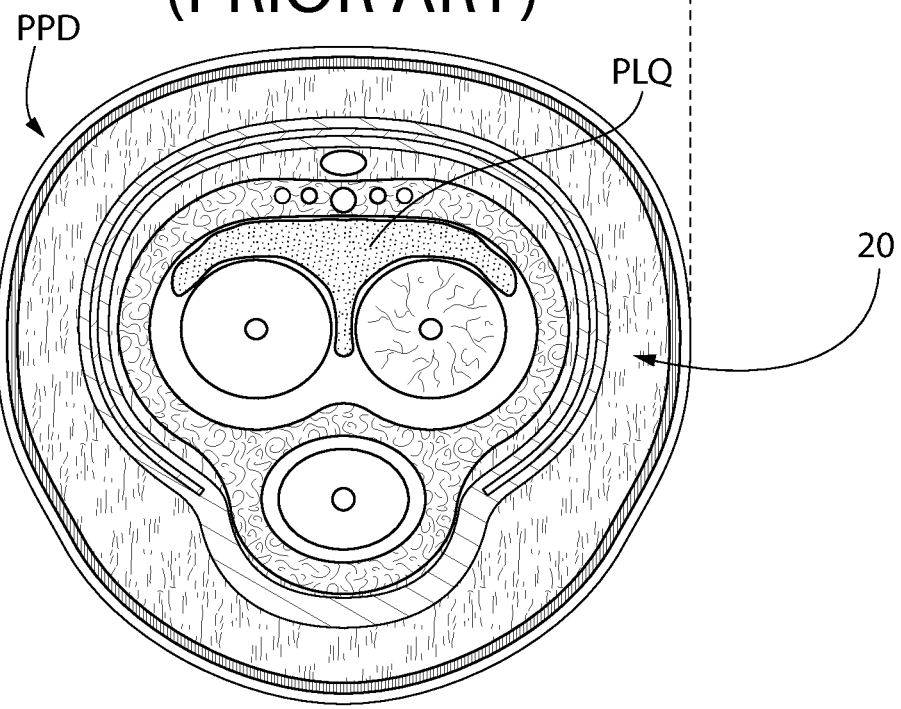
Figure 8M:
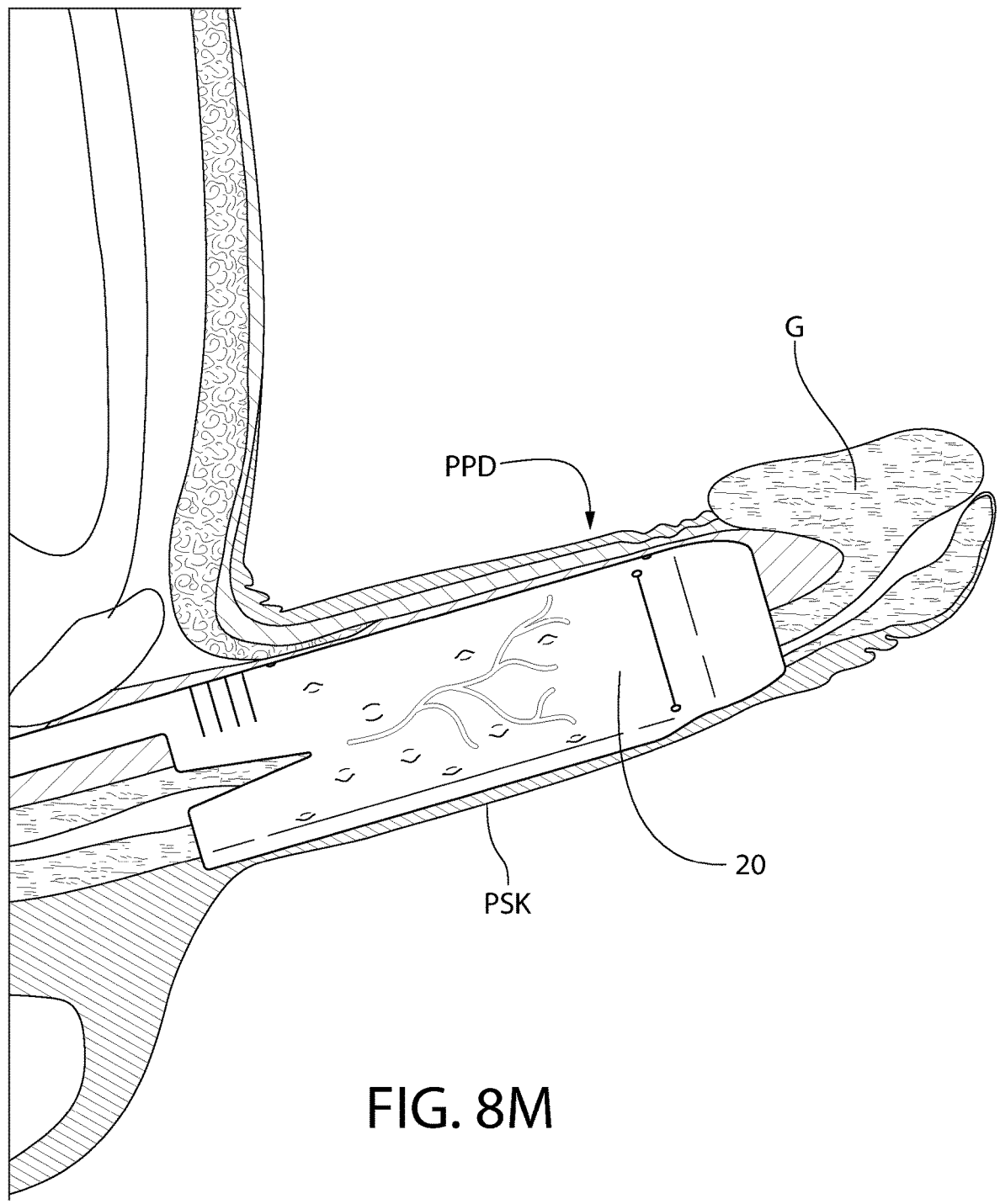
FIG. 8M depicts how the implantation of the PSD restores a more natural erect profile to a penis with Peyronie's Disease.

The DT, using the Glans Gripper Device 28 and the T-Device 30 for delivering the PSD 20 is depicted in FIGS. 7-8 and comprises the following steps:

1. The patient is prepared in a sterile fashion.
2. The patient is provided with topical and local anesthesia.
3. A superficial incision is made along the existing circumcision line (FIG. 7), such that the penile skin PSK can be displaced to reveal the subcutaneous space SS of a patient's penis (FIG. 7). By opening this existing circumcision scar CircS, there are no additional scars formed. Note: if the patient is not circumcised, then a circumcision line will be made, and as distal as possible on the penile skin sub-glans area SGA.
4. Fascial plane FP dissection (FIG. 7A) takes place using blunt instruments. This makes a clear unobstructed path for PSD 20 placement just on top of Buck's Fascia BF and all the way into the pubic pocket 50. All blunt dissection is above Buck's Fascia BF.
5. Frequent lavage is performed with sterile saline and antibiotics.
6. Length and girth measurements are taken for the PSD 20 in flaccid and in induced erect states (saline injection into corpora cavernosa CC), as discussed previously. Dorsal and ventral sides of the penile shaft PS are measured from the proximal end, all the way to the sub-glans area. In addition, depending on the goals, an outstretched flaccid length is also taken. It is important to measure the true erect length (for an optimal flaccid PSD 20), and an outstretched flaccid length (for an optimal erect PSD 20 and Supra-optimal flaccid lengthening).
7. Once the size of the PSD 20 has been determined, the correct size PSD 20 can be selected.
8. The PSD 20 is first lubricated on its external 22T3 and internal 22S2 surfaces (FIG. 1H) with C-Lube or similar biodegradable dissolvable lubricant. The pocket space 22I of the MC 22 is lubricated with S-Lube.
9. The T-Device 30 is then inserted (FIG. 4B) through the dorsal midline slit opening 22J of the MC 22 and positioned onto the IC T-Device reception slit 24K (FIG. 4B).
10. Once the T-Device 30 is in place, the Glans Gripper Device 28 is placed through the PSD tubular tunnel TT and grips the glans G, as shown in FIG. 7B.
11. Then, with a careful forward motion of the PSD 20, pushing with the T-Device 30 and pulling the Glans G simultaneously, the PSD 20 will slide into position onto the penile tissue and under the penile skin PSK.
12. Markings will be made on the penile tissue using a medical non-toxic pen. The pen will be placed through the suture slits 22N/24G (FIG. 7C) to make the pen markings directly onto the penile tissue to exactly correspond to where the suture slits are.
13. After the pen markings are made, the distal end 22A of the PSD 20 will be folded over, like cuffing a shirt sleeve, to expose the distal penile tissue and the pen marking locations.
14. Sutures will then be placed into the Tunica at those pen marked areas.
15. Then the suture ends will be threaded through the PSD dorsal surface suture slits 22N/24G to come out of the corresponding suture slits on the PSD's ventral surface.
16. Then the distal end 22A of the PSD 20 will be folded back into position.
17. Then the sutures will be pulled through 22N/24G completely, and then knots will be made (FIG. 2E). It should be noted that the S-Clip 80 will need to be in place before the knots are placed.
18. Pressure and length measurements are taken while the PSD 20 is in place. An erect state will be induced (saline injection into corpora cavernosa CC). The pressure is measured to determine the differential between the erect pressure prior to PSD 20 placement. Erect state observations take place, with special attention to erect length, erect girth, PSD 20 shape, distal tension, etc.
19. Final lavage with sterile saline and possible antibiotics.
20. External sutures ES are placed to close the circumcision line, as shown in FIG. 8. Suture removal, if non-absorbable sutures were used, will take place on day 14.
21. No intercourse until day 30.
22. Subsequent permanent filler treatment 26 (FIG. 8A) in 30 days.

PSD: Removal and Re-Insertion

Considering that the PSD 20 is placed in a permanent secured fashion under the penile shaft skin PSK, even though it can be removed at any time placed, long term stretching of the penile tissues will occur and subsequent restretching at a later point in time will be possible. This will subsequent penile tissue stretching will allow for additional penile flaccid and/or erect length by placing a longer PSD 20. For example, when the PSD 20 is placed into position, it not only exerts a force and prevents the penile shaft from retracting when in its flaccid (and erect) state, but it also causes penile tissue changes resulting in a "stretch effect". This constant applied force ultimately stretches-out the penile shaft PS resulting in lengthening in the flaccid and erect states. Then, after the penis P has stretched out and the applied force from the PSD 20 has reduced, the PSD 20 can be removed and a new and longer PSD 20 can be placed in and now apply a "new" force, again, to re-stretch the penile shaft PS to new and greater lengths. The removal of the PSD 20 involves a sterile technique, opening the circumcision line, anchor suture removal, and then sliding the PSD 20 out. Then a new PSD 20 can be inserted, if the patient desires additional lengthening. Considering the penile tissues have had time to stretch, a new PSD 20 can be placed to "re-stretch" the tissues even further to obtain additional erect lengthening.

PSD: Selection Guidelines: Some Clinical Examples

Patient #1: Desires Sub-Optimal Increase in Flaccid Length Only

Patient Info 46-year-old white healthy circumcised male with normal penis.

Erect Dimensions: 6-inches in length, 4.75-inches in girth

Flaccid Dimensions: 2-inches in flaccid length, 3.75-inches in girth

Patient Desires: Flaccid length increase to 5-inches, no change in girth.

Tx: PSD S-Fold 20A without PE (no proximal end flanges 22E/24D). PSD 20A will be 5-inches in length.

Insertion Technique: Standard circumcised line entry, blunt dissection with measurements, device placement on out-stretched penile shaft and PSD 20A mounted on 1.5 inches of stretched out penile shaft which would equal 4.5 inches. Then, post placement, the PSD 20A will occupy 4.5 inches of the flaccid stretched penile shaft, while the remaining ½ inch will remain ½ inch.

Sutures placed at distal and proximal locations to stabilize the PSD 20A.

Patient #2: Desires Optimal Increase in Flaccid Length Only.

Patient Info 32-year-old white healthy circumcised male with normal penis.

Erect Dimensions: 7-inches in length, 4.5-inches in girth

Flaccid Dimensions: 3-inches in flaccid length, 3.5-inches in girth

Patient Desires: Flaccid maximal length increase to 7-inches, no change in girth.

Tx: PSD S-Fold 20A 7-inches in length.

Insertion Technique: Standard circumcised line entry, blunt dissection with measurements, device placement on out-stretched penile shaft and PSD 20A mounted stretched out penile shaft to optimal length of 7-inches, Sutures placed at distal location to stabilize the PSD 20A.

Patient #3: Desires Increase in Erect Length

Patient Info 58-year-old black healthy circumcised male with normal penis.

Erect Dimensions: 7-inches in length, 5-inches in girth

Flaccid Dimensions: 4-inches in flaccid length, 4-inches in girth

Patient Desires: Optimal erect length increase, no change in girth.

Tx: PSD S-Fold 20A: If optimal stretch is 8-inches, then an 8-inch length device is placed. Both components provide for structural support. The Internal Component, which may need to be thicker due to the retraction forces presence, adds physical support against the retraction force and assists in the "firm" feel of an erection.

Sutures placed at distal location to stabilize the PSD 20A.

Patient #4: Desires Optimal increase in Girth Only

Patient Info 21-year-old white healthy circumcised male with normal penis.

Erect Dimensions: 5-inches in length, 4.75-inches in girth

Flaccid Dimensions: 2-inches in flaccid length, 3.75-inches in girth

Patient Desires: Girth increase to 6.5-inches, no change in length, no insert device desired. Not concerned with flaccid retracted look post filler tx.

Tx: Filler treatment only.

Injection Technique: Standard Protocol.

Patient #5: Desires Optimal Increase in Girth and Optimal Flaccid Length

Patient Info 28-year-old white healthy circumcised male with normal penis.

Erect Dimensions: 5.5-inches in length, 4.5-inches in girth

Flaccid Dimensions: 2.5-inches in flaccid length, 3.5-inches in girth

Patient Desires: Girth increase to 6.5-inches, optimal flaccid length.

Tx: PSD S-Fold 20A 5.5 inches in length, and permanent filler treatments.

Injection Technique: Standard Protocol of 2-3 treatments of filler treatments to reach 6.5-inch girth. Note: If a larger Main Component is inserted with Internal Component for firm feel, then maybe can accomplish some additional girth, and reduce the filler treatment to two sessions.

PSD Insertion Technique: Standard circumcised line entry, blunt dissection with measurements, device placement on out-stretched penile shaft and PSD 20 mounted on 1.5 inches of stretched out penile shaft which would equal 4.5 inches. Then, post placement, the PSD 20 will occupy 4.5 inches of the flaccid stretched penile shaft, while the remaining ½ inch will remain ½ inch.

Sutures placed at distal and proximal locations to stabilize the PSD 20.

Patient #6: Desires Optimal Increase in Girth and Optimal Erect Length

Patient Info 60-year-old Spanish healthy circumcised male with normal penis.

Erect Dimensions: 5-inches in length, 4.5-inches in girth

Flaccid Dimensions: 2-inches in flaccid length, 3.5-inches in girth

Patient Desires: Girth increase to 6.5-inches, optimal Erect length.

Tx: PSD S-Fold 20A: If max stretch out is 6.5-inches, then a 6.5-inch length PSD device is placed. Note: A thicker Main Component may be considered to assist in girth; this limits filler treatments needed. There might be a possibility to provide the entire length and girth with the Main Component and Internal Component.

Injection Technique: Standard Protocol of 2-3 treatments to reach 6.5-inch girth.

PSD Insertion Technique: Standard circumcised line entry, blunt dissection with measurements, device placement on out-stretched penile shaft and PSD 20 mounted on 1.5 inches of stretched out penile shaft which would equal 4.5 inches. Then, post placement, the PSD 20 will occupy 4.5 inches of the flaccid stretched penile shaft, while the remaining ½ inch will remain ½ inch.

Sutures placed at distal and proximal locations to stabilize the PSD 20.

Patient #7: Pt with Existing PSD 20 Desires to Increase Length of the Erect State Patient Info 22-year-old white healthy circumcised male with normal penis.

First PSD 20 placed in 12 months ago and insertion procedure uneventful

Original Erect Dimensions: 6-inches in length, 4.5-inches in girth

Original Flaccid Dimensions: 2-inches in flaccid length, 3.5-inches in girth

Post PSD insertion Erect Dimensions: 7-inches in length, 5.5-inches in girth

Post PSD insertion Flaccid Dimensions: 7-inches in length, 5.25-inches in girth

Patient Desires: Length increase to 7.5-8 inches. Girth increase to 6.5-inches, optimal Erect length desired on second PSD 20 placement.

Tx: Second PSD S-Fold 20A: Max stretch is 8-inches, then an 8-inch length device is placed. Both components will be higher in durometer and thickness for structural support of a now lengthy penile shaft. The Main Component provides most of the counter force of the penile retraction and is thicker to do this and provide for the girth increase. The Internal Component is of higher in durometer and thicker for support and provide some girth increase. The Internal Component adds physical support against the retraction force and assists in the "firm" feel of an erection as well. Note: Combination filler treatment will be recommended to not only achieve the girth size, but also to thicken the skin of the penile shaft to provide support and a more natural palpable feel of the PSD 20.

Injection Technique: Standard Protocol of 2-3 treatments to reach 6.5-inch girth.

PSD Insertion Technique: Standard circumcised line entry, blunt dissection with measurements, device placement on out-stretched penile shaft and PSD 20 mounted on 1.5 inches of stretched out penile shaft which would equal 4.5 inches. Then, post placement, the PSD 20 will occupy 4.5 inches of the flaccid stretched penile shaft, while the remaining ½ inch will remain ½ inch.

Sutures placed at distal and proximal locations to stabilize the PSD 20.

Patient #8: Uncircumcised Patient Desires Optimal Erect Length and Girth

Patient Info 29-year-old Black healthy uncircumcised male with normal penis.

Measurements:

Erect Dimensions: 6-inches in length, 4.5-inches in girth

Flaccid Dimensions: 2-inches in flaccid length, 3.5-inches in girth

Goal Post PSD insertion Erect Dimensions: 7-inches in length, 7-inches in girth

Goal Post PSD insertion Flaccid Dimensions: 7-inches in length, 6.5-inches in girth Patient Desires: Optimal Erect Length increase to 7-inches. Girth increase to 7-inches.

Tx Note: Special consideration of PSD 20 design considering the Pt does not want to be circumcised. The PSD 20 is modified distally or expanded to a 7-inch (total) circumference.

Tx: PSD S-Fold: Hyper-stretched flaccid length is 7-inches, then a 7-inch length device is placed. Both MC 22/IC 24 of the PSD 20 will be higher in durometer and thickness for structural support of a now lengthy penile shaft. The MC 22 provides some of the counter force of the penile retraction and is thicker, providing for the girth increase. The IC 24 is higher in durometer providing most of the counter force of the penile retraction, and thicker to provide some girth increase. The IC 24 adds physical support against the retraction force and assists in the "firm" feel of an erection as well. Note: Combination filler treatment is recommended to not only achieve the girth size, but also to thicken the skin of the penile shaft to provide support and a more natural palpable feel of the PSD 20. Very little filler is placed distally, but just tapers to keep a natural transition from filler to PSD 20 in foreskin area.

It should be understood that the placement of the PSD 20 can be supplemented with the use of permanent silicone oil filler treatments to reach desired girth goals. In addition, such treatments can assist in concealing the PSD 20 (e.g., the patient may be able to feel edges of the implanted PSD 20). Alternatively, placement of the PSD 20 alone may be sufficient to the patient in achieving the girth and flaccid-erect length size desired.

Erectile Dysfunction (ED) Support

The PSD 20 may provide Erectile Dysfunction (ED) support. For example, if a patient cannot achieve a very firm erection, the PSD 20 may provide structural support, from the harder IC 24, thus providing the additional firmness desired. On the other extreme, if a patient cannot have an erection normally, even with medical treatment, and opts not to have a penile balloon implant or metal rod implants placed, then a PSD 20 can be designed to provide a full, or near full, erect firm penis by selecting harder durometer materials for the MC 22 and IC 24. Also, additional anchor locations at the mid and proximal shaft levels might be provided.

If an ED patient desires to have a balloon implant device placed, a PSD 20 can be used simultaneously, but the PSD 20 placed on first. The PSD 20 provides length and girth, while the balloon implant provides the erection function. Filler treatments may be needed to provide the "finishing touch" to hide any palpable components under the skin and also to provide additional girth if needed. Note that the filler not only provides for additional girth and assists making the PSD 20 (and balloon implant, if used) feel better to the touch, but also this thickened skin, as a result of the filler treatment, diverts pressure off of the internal devices (from external "hand" or "vaginal" forces touching the now thickened skin), promotes stability, results in less stress placed directly on the devices, and less stress and irritation on the skin tissue as well.

When a patient is evaluated for ED and/or an enlargement procedure, there are several factors that need to be discussed. If the patient has ED, then the root cause needs to found (internal medicine and/or Urology departments for patient evaluation). If ED continues, even after, for example, the Diabetes has been under control, then the patient can then try medication/device therapy (pills, injections, suppositories, penis pumps, etc.). If the medication/penis pump device treatment does not work (The penis pump will help draw blood into the penile cavernosal tissues, then when full, a rubber band is placed at the penile base area to keep the blood "in". This may be a viable option in some patients), the patient is then evaluated for a cavernosal (balloon or metal rod implant) or subcutaneous device (PSD 20). Although a cavernosal implant is usually preferred, the PSD 20 can be considered an alternative, as mentioned above, and if a penile pump was added, this may be a beneficial partnership. As mentioned previously, the IC 24 can be made of a malleable metal material. This allows for not only upward and downward bending, as needed for intercourse, but also provides for additional hardness needed for the erection state.

If a patient has ED and wants enlargement, then a combination PSD 20 and permanent filler treatments may suffice. If an erection is not firm enough, then a balloon/metal rod implant should be added.

If a patient does not have ED, then the PSD 20 in combination with permanent filler treatments can possibly handle all of the patient's desires for increased girth and length.

Penile Stocking Insert 400

The subject disclosure also features a penile stocking insert 400 effective for increasing a length of a penis in its flaccid or erect state (FIGS. 11A-11I). The penile stocking insert may comprise an elongated tubular body having a proximal end and a distal end. In some aspects, the insert may be configured to be implanted into a penile shaft underneath a penile skin and sutured to a penile fascial tissue layer so that the insert can prevent or reduce shrinkage and elongate an appearance of the penis in its flaccid state, and can further elongate the appearance of the penis in its erect state. In one embodiment, the proximal end may be disposed near a pubic bone and the distal end may be disposed near a glans coronal rim of the penis. The distal end of the body may be at an angle so as to abut against the curvature of the glans coronal rim.

One of the unique and inventive technical features of the present invention is the elongated tubular body 405 constructed from an elastic material. Without wishing to limit the invention to any theory or mechanism, it is believed that this technical feature of the present invention advantageously provides for a compressive force, typically mild to moderate, to be applied evenly around the penile shaft, thus elongating the length of the penis without causing discomfort to the user nor interfering with regular tasks and activities. None of the presently known prior references or work has the unique inventive technical feature of the present invention.

In some embodiments, the present invention features a penile stocking insert 400 effective for increasing a length of a penis in its flaccid or erect state. Preferably, the penile stocking insert 400 may be in any suitable configuration to achieve elongation of the penis while being medically safe and comfortable to a user. Furthermore, the penile stocking insert 400 is preferably capable of expanding and flexing in multiple directions without causing pain or discomfort to the user.

Figure 11:
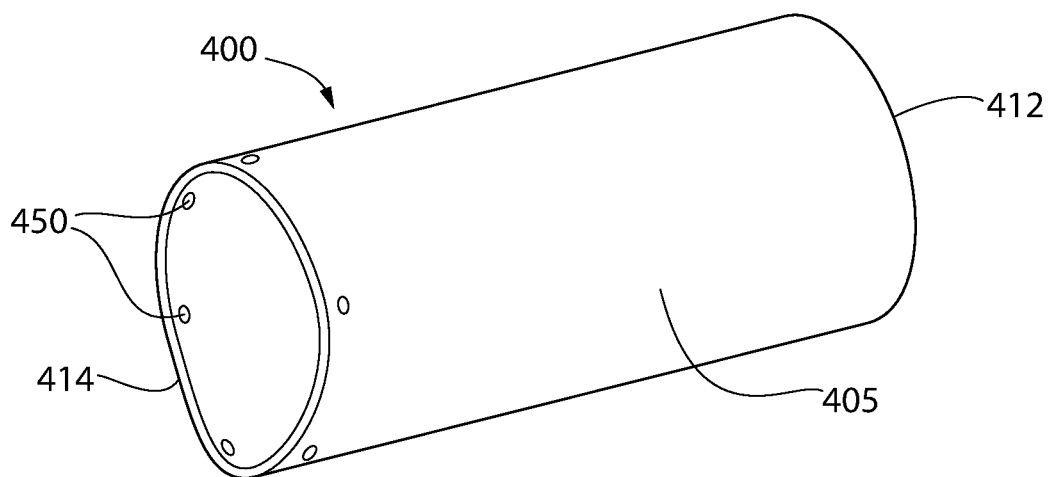
FIG. 11 is an isometric view of a penile stocking insert of the present invention
Figure 11A:
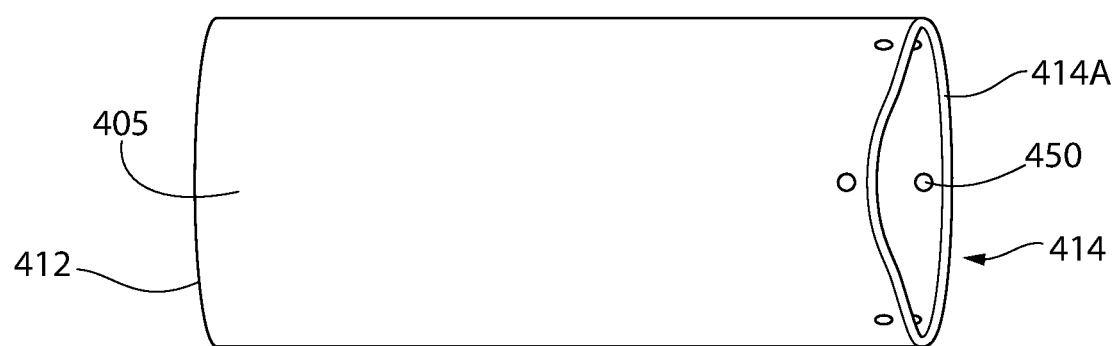
FIG. 11A is a side view of the penile stocking insert showing a vertical edge on the right end.
Figure 11B:
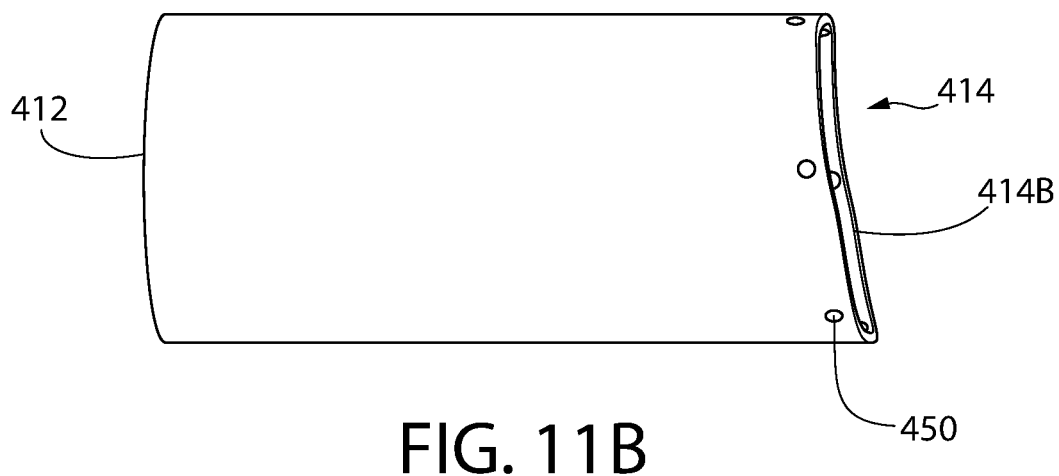
FIG. 11B is a side view of the penile stocking insert showing a diagonal edge on the right end.
Figure 11C:
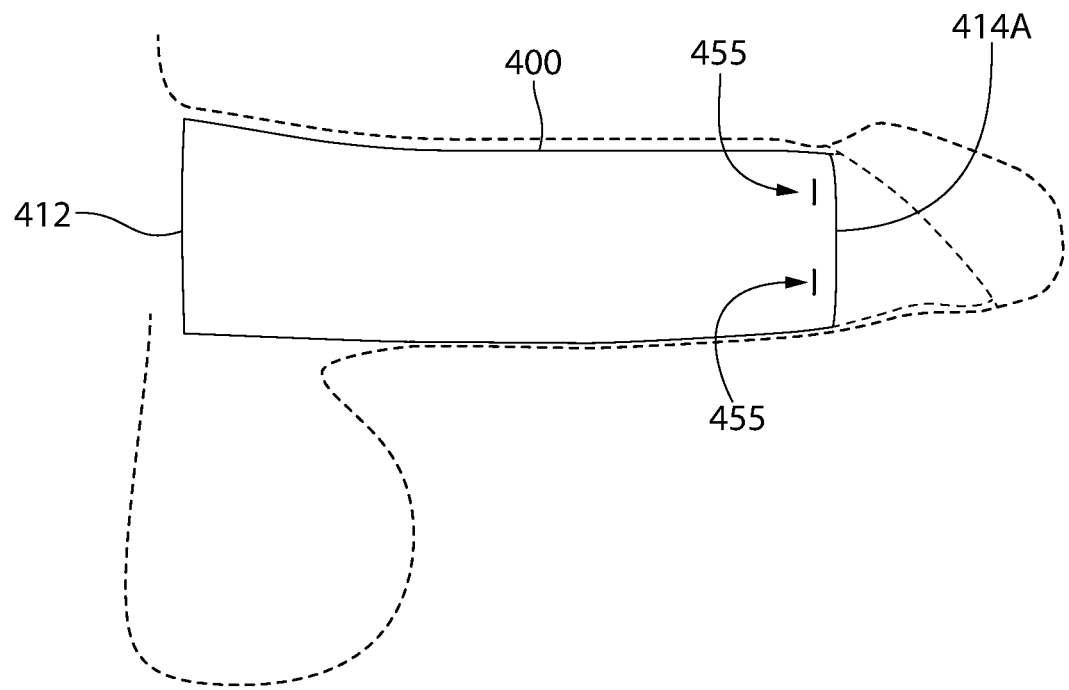
FIGS. 11C and 11D show side views of a penis with the respective penile stocking insert implanted therein.

Referring now to FIGS. 11A-11I, in some embodiments, the penile stocking insert 400 may comprise an elongated tubular body 405 having a proximal end 412 and a distal end 414 (FIGS. 11A-11C). In some embodiments, the exterior surface is convex and the interior surface is concave such that the body 405 has a circular cross-section when viewed from the proximal or distal end. The curvature of the body 405 may be similar to a surface curvature of the penis, which is advantageous in that it mimics the substantially round shape of the penis, thereby maintaining the natural shape of the penis when the insert 400 is implanted. Without wishing to limit the invention to a particular theory or mechanism, the insert 400 may prevent or reduce shrinkage, and increase the length of the penis in its flaccid state. In addition, the insert 400 is capable of bending and expanding with the penis as it also bends and becomes erect. Further still, the insert 400 can increase the length of the penis in its erect state.

In some other embodiments, the insert 400 may be sewn or attached to any tissue layer of the penis in order to function in accordance with the present invention. For example, the insert may be sewn to the Buck's fascia and/or tunica albuginea to provide for an effective increase in flaccid penile length and for long term stability of the implanted body. However, other methods of attaching the insert to the penis may be utilized, such as stapling, gluing, and the like.

Figure 11D:
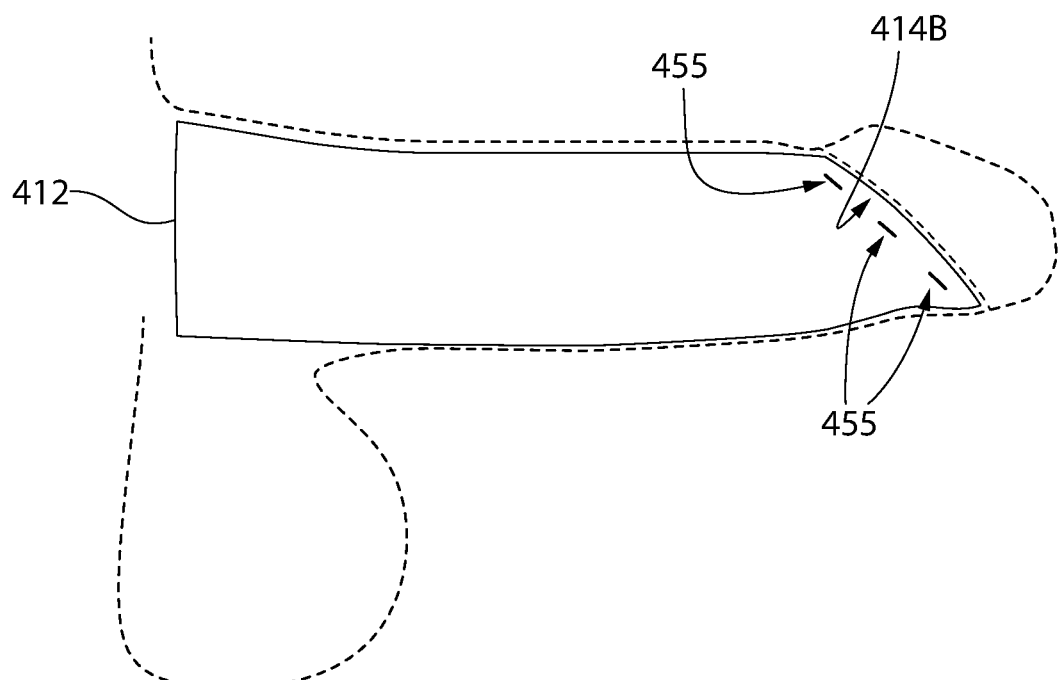

In preferred embodiments, the insert 400 may be configured to be implanted into a penile shaft of the penis and underneath a penile skin such that the proximal end 412 is disposed near a pubic bone and the distal end 414 is disposed near a glans coronal rim of the penis. (see FIG. 11F) In some embodiments, the distal end may be at a diagonal angle 414B (FIGS. 11B and 11D) when viewed from a left or right side of the penis so as to abut against and conform to a curvature of the glans coronal rim. In other embodiments, the distal end may be vertical 414A (FIGS. 11B and 11D). In some embodiments, the proximal end 412 may have a flat edge with rounded corners to allow for the insert to comfortably rest against the pubic bone. Further still, the tubular body 405 completely encloses around the penile shaft and is configured to apply a compressive force around the penile shaft, thus elongating the length of the penis. Preferably, the tubular body can bend upwardly or downwardly and sideways to allow for complete movement of the insert.

In preferred embodiments, the tubular body may be constructed from a flexible, medical-grade elastic material capable of applying a compressive force around the penile shaft, yet stretchable to allow for erection of penis. For example, the tubular body may be constructed from a medical-grade flexible, stretchable, and soft type of silicone rubber. This flexible and stretchable material is advantageous in that allows for the insert to bend with the penis while maintaining its structure. To illustrate, when the insert is mounted, or sutured, the penis may retract and if the material is too soft or pliable, the insert may bow out and protrude, which would make the insert visible through the penis skin. Further still, it is preferred that the material can stretch and expand to accommodate a penis entering an erect state. In other embodiments, the use of medical grade silicone may allow for the insert to be used for the duration of the user's lifetime.

Preferably, the ends of the tubular body have rounded tips. It is critical that the hard edge, thereby ensuring that the insert is comfortable to the user. Further, the ends of the insert may taper to the rounded tips, which advantageously allows for easier insertion of the tubular body into the penis.

In some embodiments, the insert may have a length of about 3 to 6 inches from the proximal end to the distal end. In one embodiment, the insert may have a length of about 3-4 inches. In another embodiment, the insert may have a length of about 4-5 inches. In yet another embodiment, the insert may have a length of about 5-6 inches. This variance in length will accommodate for natural variances in penile length as well as providing a recipient of the insert with a variety of choices regarding a desired penile length. In yet other embodiments, the penile insert may be manufactured to have an initial length of about 9-U inches. The penile insert may then be cut down to size to fit each recipient individually and to a desired penile length.

Preferably, the outer surface of the penile insert is convex, and the interior surface is concaved. This can allow for the penile insert to have a curvature similar to that of the penis such that the penile insert can be flushed with the penis without causing discomfort to the user.

In some embodiments, the elongated tubular body 405 can have a thickness ranging from about 0.5 to 3 mm, and taper to a rounded 1 mm end distally and proximally. In other embodiments, the elongated tubular body 405 can have an interior diameter ranging from 3-5 cm. The diameter may vary according to a patient's needs, and the desired compressive force. In some embodiments, the elongated tubular body 405 has smooth interior and exterior surfaces.

According to some embodiments, the suture aperture 450 (FIGS. 11B-11C) may have a diameter of about 0.5 to 1.5 mm. For example, the diameter of the suture aperture is about 1.5 mm. However, it is to be understood that the insert is not to be limited to any of the aforementioned dimensions, and that one of skill in the art will select the appropriate dimensions to achieve the desired effects of the present invention.

Figure 11E:
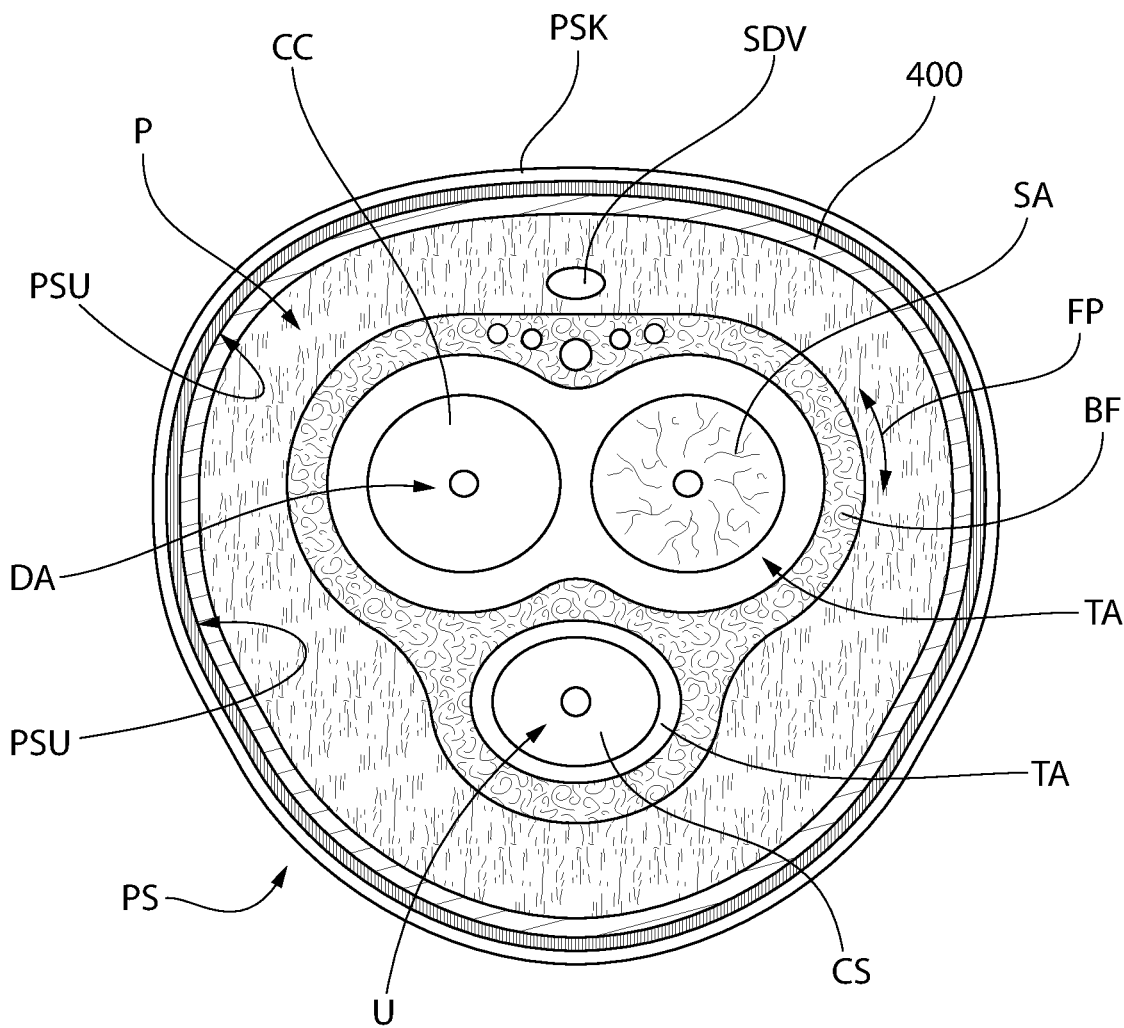
FIG. 11E is a cross-sectional view of the penile stocking insert implanted on the penile shaft.
Figure 11G:
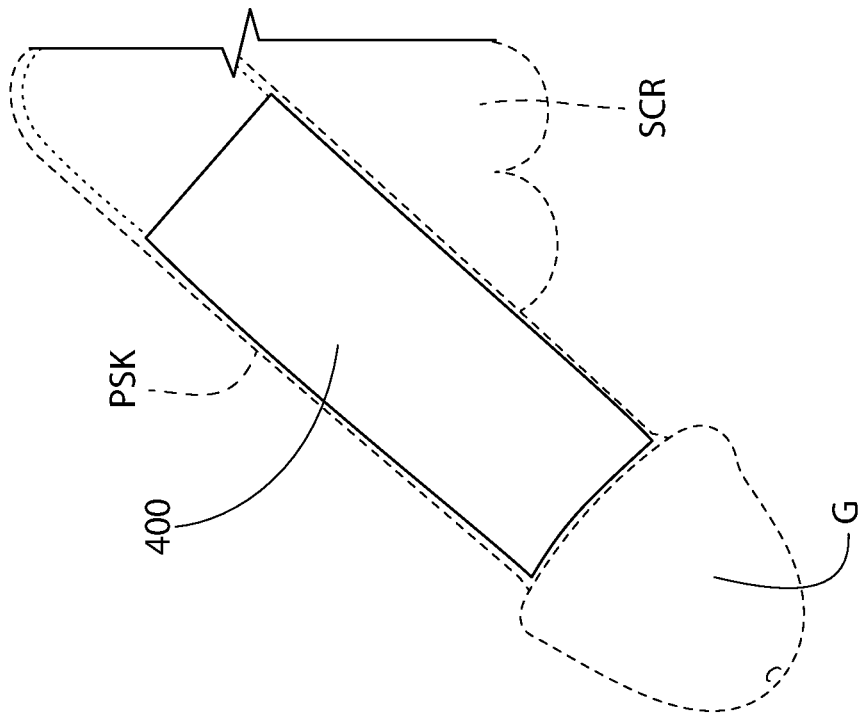
FIGS. 11F and 11G show respective views of the penile stocking insert implanted with the penile stocking insert of FIG. 11G being longer than the penile stocking insert of FIG. 11F.
Figure 11F:
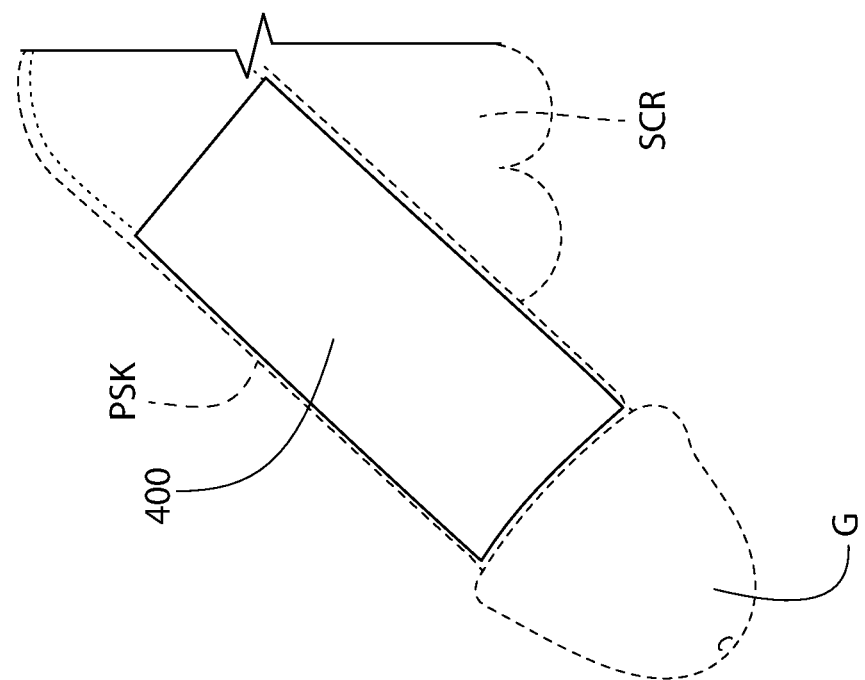
Figure 11H:
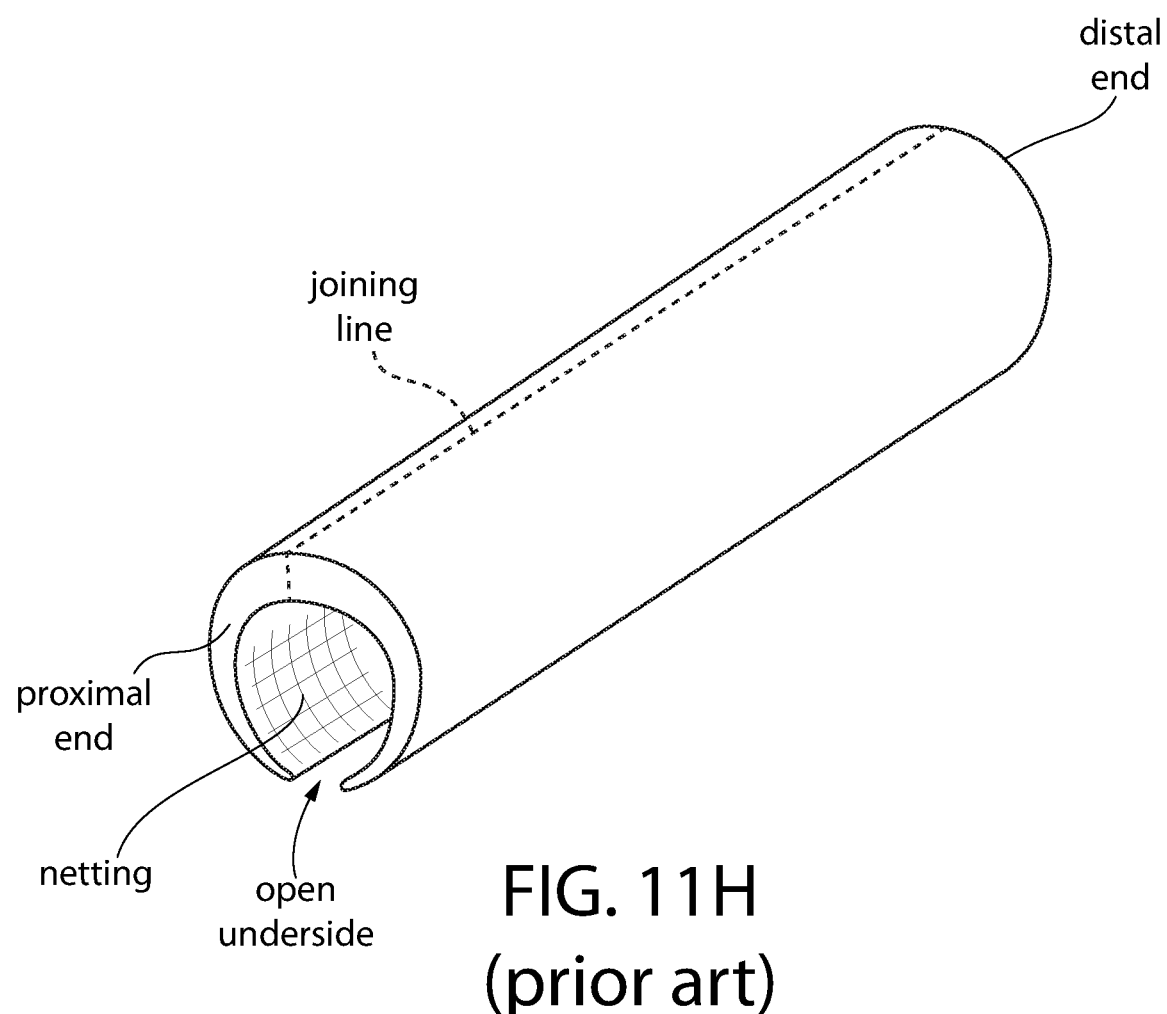
FIG. 11H shows a prior art penile implant from U.S. Pat. No. 6,537,204 (Elist).

In alternate embodiments, the body can be without suture apertures (see FIGS. 11D-11E). In this alternative embodiment, the body may be sewn or attached to the Tunica Albuginea TA or other tissue layer of the penis by wrapping or tying sutures around the edges of the insert, by stapling the body to the various tissue layers of the penis, by gluing the body to the various tissue layers of the penis, or the like.

Embodiments of the penile stocking insert 400 have been described herein for elongating the penis in its flaccid or erect state. Thus, it is a further objective of the present invention to provide for methods of implementing the insert 400. According to some embodiments, the present invention features a method of increasing a length of a penis in its flaccid or erect state. In some embodiment, the method may comprise implanting, into a shaft of the penis and underneath the penile skin, the penile stocking insert 400 according to any of the embodiments described herein, and attaching the insert 400 to a fascial tissue layer of the penis.

In some embodiments, the insert 400 is implanted into the penile shaft such that the tubular body 405 completely encloses around the penile shaft. Further still, the proximal end 412 may be disposed near a pubic bone and the distal end 414 may be disposed near a glans coronal rim of the penis. Preferably, the curvature of the body may be similar to the surface curvature of the penis. In some embodiments, the insert 400 may be attached to penis tissue via sutures. Without wishing to limit the invention to a particular theory or mechanism, the insert 400 can apply a compressive force around the penile shaft, thus elongating the appearance (i.e. length) of the penis, as well as preventing or reducing shrinkage of the penis in its flaccid state.

In one embodiment, the step of attaching the insert 400 to the fascial tissue layer of the penis may comprise suturing through the tissue layer near the glans coronal rim of the penis and through suture apertures 450 disposed at the distal end 414 of the tubular body. In some embodiments, the insert 400 may be attached to a fascial layer of the Buck's fascia and tunica albuginea.

According to some embodiments, the penile stocking insert 400 is configured to apply a constant inwardly-directed radial force on the penile shaft, which results in keeping the flaccid and possibly the erect state lengthened. The force applied by the insert is an inwardly-directed radial or a squeezing force, whereas the insert of U.S. Pat. No. 6,537,204 (Elist) shown in FIG. 32 applies a splint, or "pull and hold in place" force. In contradistinction, the penile stocking insert 400 has a complete tubular stretchy body, unlike the prior art, which shows a partial cylindrical structure.

The insert 400 can expand outwardly to allow the penis to become erect, otherwise the penis would be constricted and not expand in girth, which would be painful. The prior art teaches a C-shaped rigid insert that has an opening at a joint area to allow for the penis become erect. Even if the prior art was a tubular insert, it would not be able to expand during an erection since it is a rigid structure; instead, it would be constrictive and cause pain and tissue damage to the penis. Furthermore, the thickness of the penile stocking insert 400 of the present invention is very thin, relative to the much thicker thickness, due to its rigid nature, of the prior art.

In some embodiments, the penile stocking insert 400 can be placed on an outstretched (pulled flaccid) penis and slip over Buck's Fascia BF of the penile shaft, after the penile skin has been "de-gloved" or pulled down. The insert can remain in position and exert a mild to moderate "spandex" or "stocking" (inwardly-directed radial) type of compressive force. This is a key feature that distinguishes it from the prior art. This compressive force effect squeezes the penile shaft and provides the force not only to keep the insert in a stable position, but also to keep the penile shaft outstretched and lengthened in the flaccid and erect states. The prior art does not exert any inwardly-directed radial "squeezing type" pressure force on the penile shaft. In fact, the prior art is free floating, so it must be sutured and mounted aggressively into place. In some embodiments, the penile stocking insert 400 of the present invention may be optionally sutured to prevent the insert from potentially slipping or rolling downwards on the shaft during physical or sexual activity. The sutures, if desired, may be placed at or near the glans (or distal end) area.

Without desiring to limit the invention to a particular theory or mechanism, the penile stocking insert 400 can hold the flaccid penis in a full outstretched position and exert a force in an even cylindrical manner to aid in maintaining the penis lengthened in the flaccid and erect states. In other words, the penile stocking insert 400 can continuously squeeze the penile shaft to lengthen.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the below claims are solely for ease of examination of this patent application, and are exemplary, and are not intended in any way to limit the scope of the claims to the particular features having the corresponding reference numbers in the drawings. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement of claiming one or more embodiments of the present invention using the phrase "consisting of" is met.

REFERENCE CHARACTER AND ABBREVIATION DEFINITIONS

B bladder
BF Buck's Fascia
C-Lube Carboxymethylcellulose Gel Lubrication, CMC Gel
CC Corpus Cavernosum
COL collar on the MC-PROX and MC-DIST for coupling within receptacles in INS
CR Coronal Rim
CS Corpus Spongiosum
CT connecting tube of PSD-Volume Shift
CSASM Corpus Spongiasum
DA Deep Artery of Penis
DDV Deep Dorsal Vein of Penis
DF Dartos Fascia
DN Dorsal Nerve
DORA Dorsal Artery of Penis
DT Delivery Technique
ED Erectile Dysfunction
EGM erect girth measurement
ELDS erect length dorsal side measurement
ELVS erect length ventral side measurement
EOL erect overall length measurement
EPG enhanced penile girth
EPL enhanced penile length
ES external sutures
FBR foreign body reaction
FG flaccid girth measurement
FP Fascial Plane
$F_{RI}$ Inwardly-directed radial force
$F_{RO}$ Outwardly-directed radial force
FTZ Filler Transition Zone
G glans
HEG hyperextended girth measurement
HELDS hyperextended length dorsal side measurement
HELVS hyperextended length ventral side measurement
HEOL hyperxtended overall length measurement
IC Internal Component
INS insert portion of PSD-Insert embodiment 20E
MC Main Component
MC-DIST distal portion of the PSD-Insert embodiment 20E
MC-PROX proximal portion of the PSD-Insert embodiment 20E
MC-T1 distal telescoping portion of the PSD-Telescoping Design embodiment 20F
MC-T2 proximal telescoping portion of the PSD-Telescoping Design embodiment 20F
MS mounting sutures
P penis
PB pubic bone
PF penile fascia
PPD penis with Peyronie's Disease
PLQ plaque
PR Prostate
PS penile shaft
PSCS penile shaft cross section
PSD Penile Sleeve Device
PSK penile skin
PSK-D penile skin dermis
PSK-E penile skin epidermis
PSU penile skin underside
R external reservoir for PSD-Volume Shift
REC receptacles in INS for receiving collars COL of MC-PROX and MC-DIST
S suture
SA Sinusoidal Architecture
SCR scrotum
SDV Superficial Dorsal Vein of Penis
SGA penile skin sub-glans area
S-Lube Silicone Oil Lubrication
SPK radial spokes in PSD-Volume Shift embodiment
SS Subcutaneous Space
T testicle
TA Tunica Albuginea
TT Tubular Tunnel
U Urethra
10 area in penile shaft that may be occupied with ligament & tissues (FIG. 8E)
20 PSD (also PSD-smooth)
20A PSD-S-fold
20A1 PSD-wave-fold
20A2 PSD-Tight-S
20B PSD-Collapsible
20C PSD-Volume Shift
20D PSD-Spoke
20E PSD-Insert
20F PSD-Telescoping Design
22 MAIN COMPONENT
22A distal end
22B medial ventral area
22C medial dorsal area
22D proximal ventral end
22DT rounded edges of proximal ventral end
22E proximal end flange
22EC proximal end flange collapsed area
22ET rounded edges of proximal end flange
22E' proximal end flange of PSD-Collapsible
22E" proximal end flange of PSD-Volume Shift
22F veiny-look/texture
22G bumps
22H tear reduction
22I pocket space in Main Component between inner and outer layers
22ID pocket space distal
22IL pocket space lateral
22IP pocket space proximal
22J dorsal mid-line slit
22JG groove of slit
22JT tongue of slit
22L buckling spaces
22M suture anchor locations on the penile tissue
22N suture slits with "5-pattern box"
22O proximal lateral V-Cut
22OT proximal latera V-Cut rounded edges
22P tapered distal end
22Q proximal end flange pocket to receive IC proximal end flange
22R U-shaped portion along ventral side of Main Component (FIGS. 9B-9C)
22S bilayer (inner layer 22S1 and outer layer 22T1, FIG. 1H)
22S1 inner layer
22S2 inner layer inner surface
22S3 inner layer outer surface
22T1 outer layer
22T2 outer layer inner surface
22T3 outer layer outer surface
22W single layer
22Z distal lateral line slit
22ZG slit groove
22ZT slit tongue
24 INTERNAL COMPONENT
24A distal end 24B body portion
24C proximal ventral end
24D proximal end flange
24E proximal lateral V-Cut
24F buckle zone
24G suture slits with "5-pattern box"
24GA additional suture slit locations
24H dorsal V-cuts
24HE dorsal V-cut edge
24I ventral V-cuts
24IE ventral V-cut edge
24J second internal component
24K proximal dorsal reception slit for the working distal end of T-Device
24L inner surface
24M outer surface
24N piping
24O 1 mm port slit for erect testing injections
24' Internal Component that is initially flat (FIG. 3C)
26 new collagen layer promoted by filler treatment (FIG. 8A)
28 Glans Gripper Device
28A distal portion
28B medial portion
28C proximal portion
28D pads
30 T-Device
30A handle
30B curved working distal end
40 Pubic Fascial Plane (FIG. 8E)
50 Pubic Pocket (FIG. 8E)
80 Suture Clip
95I inner layer S-Folds of Main Component
95I' inner layer wavy-folds of Main Component
95I" inner layer Tight-S folds of Main Component
95O outer layer S-Folds of Main Component
95O' outer layer wavy-folds of Main Component
95O" outer layer Tight-S folds of Main Component
400 PENILE STOCKING INSERT
405 elongated tubular body
412 proximal end
414 distal end
414A vertical distal end
414B diagonal angle distal end
450 suture aperture
455 suture While the invention has been described in detail and with reference to specific examples thereof, it will be apparent to one skilled in the art that various changes and modifications can be made therein without departing from the spirit and scope thereof.

What is claimed is:

1. A penile sleeve device configured for implantation in a subcutaneous space of a patient's penis having a penile shaft, between the patient's pubic bone and the patient's penis glans, for enhancing or correcting penis shape and size, treating low to moderate level erectile dysfunction, or correcting penis curvature or malformation, said penile sleeve device comprising:
    an elongated tubular section comprising a flexible elastomer for maintaining the penis outstretched in a flaccid or erect state, said elongated tubular section having a proximal end flange, configured for positioning near the pubic bone, and having a tapered distal end, configured for positioning adjacent the glans of the penis, said elongated tubular section being configured to be positioned around the penile shaft in the subcutaneous space of the patient's penis; and
    wherein said elongated tubular section comprises a longitudinal pocket formed between an outer layer and an inner layer of said elongated tubular section and wherein said penile sleeve device further comprises an elongated open-tubular section comprising a high durometer silicone rubber material or a metal malleable alloy for providing hardness and structural support features to said penile sleeve device, said elongated open-tubular section being insertable through a longitudinal dorsal slit in said outer layer of said elongated tubular section and positioned within said longitudinal pocket such that said elongated open-tubular section is not in direct contact with the penile shaft.

2. The penile sleeve device of claim 1 wherein said proximal end flange comprises a pocket space therein and wherein said elongated open-tubular section comprises another proximal end flange and wherein said another proximal end flange is positioned within said proximal end flange of said elongated tubular section when said elongated open-tubular section is positioned within said longitudinal pocket, said elongated open-tubular section being concealed within said outer layer.

3. The penile sleeve device of claim 1 wherein said elongated tubular section and said elongated open-tubular section each comprise a respective buckle zone at a proximal end of respective dorsal portions of said elongated tubular section and said elongated open-tubular section, said buckle zones aligning to provide slack to said penile sleeve device when the penis is bent.

4. The penile sleeve device of claim 1 further comprising a plurality of suture slits on sides of said elongated tubular section, said plurality of suture slits being formed in said inner layer of said elongated tubular section.

5. The penile sleeve device of claim 1 wherein said outer layer of said elongated tubular section comprises vein features and bumps for simulating the appearance of a penis shaft.

6. The penile sleeve device of claim 1 wherein a ventral side of said elongated tubular section comprises a U-shaped portion along an entire length of said elongated tubular section, said U-shaped portion permitting urinary flow when the penis is in the flaccid and erect states.

7. The penile sleeve device of claim 1 wherein said outer layer comprises a closure to seal said slit.

8. The penile sleeve device of claim 7 wherein said closure comprises a tongue and a groove to seal said slit.

9. A method for forming a penile sleeve device configured for implantation in a subcutaneous space of a patient's penis, on the patient's penile shaft between the patient's pubic bone and the patient's penis glans, for enhancing or correcting penis shape and size, treating low to moderate level erectile dysfunction, or correcting penis curvature or malformation, said method comprising:
    (a) forming an elongated tubular section from a flexible elastomer for maintaining the penis outstretched in a flaccid or erect state, said forming further comprising forming a flange, configured for positioning near the pubic bone, at a proximal end of said elongated tubular section while forming a tapered portion, configured for positioning adjacent the glans of the penis, on a distal end of said elongated tubular section;
    (b) forming an elongated open-tubular section comprising a high durometer silicone rubber material or a metal malleable alloy for providing hardness and structural support features to said penile sleeve device, said elongated open-tubular section comprising a proximal end flange; and (c) inserting said elongated open-tubular section, through a dorsal mid-line slit formed in an outer layer of said elongated tubular section, within a longitudinal pocket between said outer layer and an inner layer of said elongated tubular section to prevent said elongated open-tubular section from making direct contact with the penile shaft, said proximal end flange of said elongated open-tubular section being positioned within a pocket space within said flange at said proximal end of said elongated tubular section.

10. The method of claim 9 wherein said step of forming said elongated tubular section comprises forming vein features and bumps in said outer layer for simulating the appearance of a penile shaft.

* * * * *